US012799075B2

(12) United States Patent
Overbeek et al.

(10) Patent No.: US 12,799,075 B2
(45) **Date of Patent: *Nov. 17, 2026**

(54) PARTICLES OF (AZIRIDINYL HYDROXY)-FUNCTIONAL ORGANIC COMPOUNDS

(71) Applicant: COVESTRO (NETHERLANDS) B.V., Geleen (NL)

(72) Inventors: Gerardus Cornelis Overbeek, Geleen (NL); Patrick Johannes Maria Stals, Geleen (NL); Daan Van Der Zwaag, Geleen (NL); Alfred Jean Paul Bückmann, Geleen (NL); Stella Josette Van Dijk, Geleen (NL)

(73) Assignee: Covestro (Netherlands) B.V., Geleen (NL)

( * ) Notice: Subject to any disclaimer, the term of this patent is extended or adjusted under 35 U.S.C. 154(b) by 1167 days.

This patent is subject to a terminal disclaimer.

(21) Appl. No.: 17/791,782

(22) PCT Filed: Jan. 21, 2021

(86) PCT No.: PCT/EP2021/051376

§ 371 (c)(1),
(2) Date: Jul. 8, 2022

(87) PCT Pub. No.: WO2021/148556

PCT Pub. Date: Jul. 29, 2021

(65) Prior Publication Data

US 2023/0110237 A1 Apr. 13, 2023

(30) Foreign Application Priority Data

| | | |
|---|---|---|
| Jan. 22, 2020 | (EP) | 20153154 |
| Jan. 22, 2020 | (EP) | 20153159 |
| Jan. 22, 2020 | (EP) | 20153239 |
| Jan. 22, 2020 | (EP) | 20153240 |
| Jan. 22, 2020 | (EP) | 20153242 |
| Jan. 22, 2020 | (EP) | 20153245 |
| Jan. 22, 2020 | (EP) | 20153246 |
| Jan. 22, 2020 | (EP) | 20153249 |
| Jan. 22, 2020 | (EP) | 20153250 |
| Jan. 22, 2020 | (EP) | 20153251 |
| Jan. 22, 2020 | (EP) | 20153253 |
| Jan. 24, 2020 | (EP) | 20153628 |

(Continued)

(51) Int. Cl.
*C07D 203/10* (2006.01)
*C07D 251/32* (2006.01)
(Continued)

(52) U.S. Cl.
CPC ......... *C07D 203/10* (2013.01); *C07D 251/32* (2013.01); *C07D 403/12* (2013.01);
(Continued)

(58) Field of Classification Search
CPC .................................................... C07D 203/10
See application file for complete search history.

(56) References Cited

U.S. PATENT DOCUMENTS

| | | | |
|---|---|---|---|
| 3,329,674 | A | 7/1967 | Bulbenko et al. |
| 3,337,533 | A | 8/1967 | Ham |

(Continued)

FOREIGN PATENT DOCUMENTS

| | | | |
|---|---|---|---|
| CN | 1368524 | A | 9/2002 |
| CN | 1606574 | A | 4/2005 |

(Continued)

OTHER PUBLICATIONS

Dahlquist et al., "Contact allergy to trimethylolpropane triacrylate (TMPTA) in an aziridine plastic hardener", Contact Dermatitis, 1983, pp. 122-124, vol. 9.

(Continued)

*Primary Examiner* — Matthew P Coughlin
(74) *Attorney, Agent, or Firm* — The Webb Law Firm

(57) ABSTRACT

The invention relates to particles comprising a particular (aziridinyl hydroxy)-functional organic component. The invention further relates to mixtures comprising said particles. The invention further relates to aqueous dispersions comprising said particles. The invention further relates to aqueous compositions comprising said particles. The invention further relates to coating compositions comprising said particles. The invention further relates to aqueous coating compositions comprising said particles. The invention further relates to particles obtained by a process comprising—amongst others—the steps of providing an aqueous dispersion comprising a particular (aziridinyl hydroxy)-functional organic component. The invention further relates to a kit-of-parts comprising in one of its parts an aqueous dispersion comprising a particular (aziridinyl hydroxy)-functional organic component. The invention further relates to cured forms of the various particles, mixtures, aqueous dispersions, aqueous compositions, coating compositions, and aqueous coating compositions. The invention further relates to articles comprising the particles and/or said mixtures, and/or said aqueous dispersions and/or aqueous compositions and/or said cured forms. The invention further relates to various uses of the particles and/or said mixtures, and/or said aqueous dispersions and/or aqueous compositions and/or said cured forms.

23 Claims, No Drawings

(30) Foreign Application Priority Data

Jan. 24, 2020 (EP) .................................... 20153630
Jul. 24, 2020 (EP) .................................... 20187717

(51) Int. Cl.

| | |
|---|---|
| ***C07D 403/12*** | (2006.01) |
| ***C07D 403/14*** | (2006.01) |
| ***C07D 413/14*** | (2006.01) |
| ***C07D 487/14*** | (2006.01) |
| ***C08F 220/18*** | (2006.01) |
| ***C08G 18/02*** | (2006.01) |
| ***C08G 18/08*** | (2006.01) |
| ***C08G 18/12*** | (2006.01) |
| ***C08G 18/22*** | (2006.01) |
| ***C08G 18/24*** | (2006.01) |
| ***C08G 18/28*** | (2006.01) |
| ***C08G 18/30*** | (2006.01) |
| ***C08G 18/32*** | (2006.01) |
| ***C08G 18/34*** | (2006.01) |
| ***C08G 18/38*** | (2006.01) |
| ***C08G 18/42*** | (2006.01) |
| ***C08G 18/44*** | (2006.01) |
| ***C08G 18/48*** | (2006.01) |
| ***C08G 18/66*** | (2006.01) |
| ***C08G 18/67*** | (2006.01) |
| ***C08G 18/73*** | (2006.01) |
| ***C08G 18/75*** | (2006.01) |
| ***C08G 18/76*** | (2006.01) |
| ***C08G 18/79*** | (2006.01) |
| ***C08G 18/83*** | (2006.01) |
| ***C08K 5/3412*** | (2006.01) |
| ***C08K 5/3492*** | (2006.01) |
| ***C08L 63/00*** | (2006.01) |
| ***C09D 7/20*** | (2018.01) |
| ***C09D 7/45*** | (2018.01) |
| ***C09D 7/63*** | (2018.01) |
| ***C09D 7/65*** | (2018.01) |
| ***C09D 11/101*** | (2014.01) |
| ***C09D 133/02*** | (2006.01) |
| ***C09D 133/04*** | (2006.01) |
| ***C09D 175/04*** | (2006.01) |
| ***C09D 175/08*** | (2006.01) |
| ***C09D 175/12*** | (2006.01) |

(52) U.S. Cl.

CPC ......... *C07D 403/14* (2013.01); *C07D 413/14* (2013.01); *C07D 487/14* (2013.01); *C08F 220/1804* (2020.02); *C08G 18/027* (2013.01); *C08G 18/0823* (2013.01); *C08G 18/0866* (2013.01); *C08G 18/12* (2013.01); *C08G 18/227* (2013.01); *C08G 18/246* (2013.01); *C08G 18/282* (2013.01); *C08G 18/2825* (2013.01); *C08G 18/283* (2013.01); *C08G 18/2865* (2013.01); *C08G 18/2875* (2013.01); *C08G 18/302* (2013.01); *C08G 18/3228* (2013.01); *C08G 18/3231* (2013.01); *C08G 18/3275* (2013.01); *C08G 18/348* (2013.01); *C08G 18/3842* (2013.01); *C08G 18/4291* (2013.01); *C08G 18/44* (2013.01); *C08G 18/4808* (2013.01); *C08G 18/4825* (2013.01); *C08G 18/4854* (2013.01); *C08G 18/4862* (2013.01); *C08G 18/4879* (2013.01); *C08G 18/6692* (2013.01); *C08G 18/6715* (2013.01); *C08G 18/73* (2013.01); *C08G 18/755* (2013.01); *C08G 18/758* (2013.01); *C08G 18/765* (2013.01); *C08G 18/792* (2013.01); *C08G 18/798* (2013.01); *C08G 18/833* (2013.01); *C08K 5/3412* (2013.01); *C08K 5/34924* (2013.01); *C08K 5/34926* (2013.01); *C08L 63/00* (2013.01); *C09D 7/20* (2018.01); *C09D 7/45* (2018.01); *C09D 7/63* (2018.01); *C09D 7/65* (2018.01); *C09D 11/101* (2013.01); *C09D 133/02* (2013.01); *C09D 133/04* (2013.01); *C09D 175/04* (2013.01); *C09D 175/08* (2013.01); *C09D 175/12* (2013.01); *C08G 2150/00* (2013.01)

(56) References Cited

U.S. PATENT DOCUMENTS

| | | | |
|---|---|---|---|
| 3,523,750 | A | 8/1970 | Tesoro |
| 3,560,415 | A | 2/1971 | Grögler et al. |
| 3,583,977 | A | 6/1971 | Uelzmann |
| 3,763,132 | A | 10/1973 | Meiser |
| 3,933,936 | A | 1/1976 | Smith et al. |
| 4,605,698 | A | 8/1986 | Briden |
| 5,106,993 | A | 4/1992 | Kania |
| 5,133,997 | A | 7/1992 | Maier et al. |
| 5,164,467 | A | 11/1992 | Kania |
| 5,241,001 | A | 8/1993 | Kania et al. |
| 5,258,481 | A | 11/1993 | Hesselmans et al. |
| 5,359,005 | A | 10/1994 | Kania et al. |
| 5,712,331 | A | 1/1998 | Ryang |
| 7,294,449 | B1 | 11/2007 | Guideman et al. |
| 7,396,891 | B2 | 7/2008 | Gray et al. |
| 8,318,855 | B2 | 11/2012 | Schafheutle et al. |
| 2003/0229176 | A1 | 12/2003 | Trombetta et al. |
| 2006/0117991 | A1 | 6/2006 | Mayo et al. |
| 2006/0148980 | A1 | 7/2006 | Tielemans et al. |
| 2007/0298006 | A1 | 12/2007 | Tomalia et al. |
| 2008/0114096 | A1 | 5/2008 | Qu et al. |
| 2010/0227945 | A1 | 9/2010 | Bissinger et al. |
| 2011/0086180 | A1 | 4/2011 | Tielemans |
| 2015/0118501 | A1 | 4/2015 | Lu et al. |
| 2017/0218110 | A1 | 8/2017 | Arzt et al. |
| 2023/0054196 | A1* | 2/2023 | Overbeek .......... C08G 18/4808 |

FOREIGN PATENT DOCUMENTS

| | | | |
|---|---|---|---|
| CN | 1720223 | A | 1/2006 |
| CN | 1823110 | A | 8/2006 |
| CN | 101365688 | A | 2/2009 |
| CN | 101437863 | A | 5/2009 |
| CN | 101619164 | A | 1/2010 |
| CN | 102046688 | A | 5/2011 |
| CN | 104080861 | A | 10/2014 |
| CN | 104379618 | A | 2/2015 |
| CN | 105143297 | A | 12/2015 |
| CN | 105377918 | A | 3/2016 |
| CN | 105705598 | A | 6/2016 |
| CN | 107922762 | A | 4/2018 |
| CN | 108084870 | | 5/2018 |
| CN | 110023354 | A | 7/2019 |
| CN | 110248977 | A | 9/2019 |
| CN | 110607120 | A | 12/2019 |
| CN | 112469755 | A | 3/2021 |
| CN | 117015566 | A | 11/2023 |
| CN | 117836343 | A | 4/2024 |
| EP | 0 507 407 | | 10/1992 |
| EP | 0 758 662 | | 2/1997 |
| EP | 1 865 014 | | 12/2007 |
| GB | 1344725 | | 1/1974 |
| JP | 47-027971 | | 8/1972 |
| JP | 51-141860 | | 5/1976 |
| JP | 59-128291 | | 7/1984 |
| JP | 11-500152 | | 1/1999 |
| JP | 2012-529473 | | 11/2012 |
| JP | 2015-505889 | | 2/2015 |
| KR | 1020060066442 | A | 6/2006 |
| NL | 9100578 | | 4/1992 |

(56) References Cited

FOREIGN PATENT DOCUMENTS

| | | | |
|---|---|---|---|
| WO | 2006/115547 | | 11/2006 |
| WO | 2008069298 | A1 | 6/2008 |
| WO | 2013/089927 | | 6/2013 |
| WO | 2015/066868 | | 5/2015 |
| WO | 2017216767 | A1 | 12/2017 |
| WO | 2020/020714 | | 1/2020 |

OTHER PUBLICATIONS

Fei et al., "Properties and Curing Kinetic of Acrylic Resin Cured with Aziridine Crosslinker", Chinese Journal of Synthetic Chemistry, 2002, pp. 120-125, vol. 10, Issue 2.

Haitao et al., "Synthesis and Application of Aziridine Crosslinking Agent in Waterborne Coatings", Shanghai Coatings, 2013, 7 pages, vol. 51, No. 10.

Jiao, "Preparation of Waterborne Polyurethane Based on Renewable Resources and Its Film Properties", Masteral Dissertation, Dalian University of Technology, 2010, 79 pages.

Lee et al., "Preparation and characterization of acrylic pressure-sensitive adhesives based on UV and heat curing systems", International Journal of Adhesion and Adhesives, 2017, 21 pages.

Qingfang et al., "Study on heat resistance of polyurethane-imide/organosilicon modified epoxy coatings", Synthetic Materials and Applications, 2018, 5 pages, vol. 47, No. 3.

Walsh et al., "Polyamine-Functional Sterically Stabilized Latexes for Covalently Cross-Linkable Colloidosomes", Langmuir, 2010, pp. 18039-18048, vol. 26(23).

Wang et al., "Pervaporation Properties to Aromatic/Non-Aromatic Hydrocarbon Mixtures of Cross-Linked Membranes of Copoly(methacrylates) with Pendant Phosphate and Carbamoylphosphonate Groups", Journal of Membrane Science, 2002, pp. 13-27, vol. 199.

Yoo et al., "Preparation of Acrylic Copolymers and Crosslinking Agents and Properties as a Film", Journal of Applied Polymer Science, 2009, pp. 1587-1594, vol. 112.

Zilin et al., "Effect of Crosslinking Agent on Waterborne Polyurethane Wet Friction Fixing Agent", Shandon Chemical Industry, 2019, pp. 1-4, vol. 8, Issue 14.

International Search Report for PCT/EP2021/051376, mailed Feb. 19, 2021, 4 pages.

Written Opinion of the ISA for PCT/EP2021/051376, mailed Feb. 19, 2021, 7 pages.

International Preliminary Report on Patentability for PCT/EP2021/051376, mailed Apr. 26, 2021, 67 pages.

* cited by examiner

PARTICLES OF (AZIRIDINYL HYDROXY)-FUNCTIONAL ORGANIC COMPOUNDS

This application is the U.S. national phase of International Application No. PCT/EP2021/051376 filed Jan. 21, 2021 which designated the U.S. and claims priority to EP patent application No. 20153154.8 filed Jan. 22, 2020, EP patent application No. 20153159.7 filed Jan. 22, 2020, EP patent application No. 20153239.7 filed Jan. 22, 2020, EP patent application No. 20153240.5 filed Jan. 22, 2020, EP Patent Application No. 20153242.1 filed Jan. 22, 2020, EP patent application No. 20153245.4 filed Jan. 22, 2020, EP patent application No. 20153246.2 filed Jan. 22, 2020, EP patent application No. 20153249.6 filed Jan. 22, 2020, EP patent application No. 20153250.4 filed Jan. 22, 2020, EP patent application No. 20153251.2 filed Jan. 22, 2020, EP patent application No. 20153253.8 filed Jan. 22, 2020, EP patent application No. 20153628.1 filed Jan. 24, 2020, EP patent application No. 20153630.7 filed Jan. 24, 2020, and EP patent application Ser. No. 20/187,717.2 filed Jul. 24, 2020, the entire contents of each of which are hereby incorporated by reference.

The invention relates to particles comprising a particular (aziridinyl hydroxy)-functional organic component. The invention further relates to mixtures comprising said particles. The invention further relates to aqueous dispersions comprising said particles. The invention further relates to aqueous compositions comprising said particles. The invention further relates to coating compositions comprising said particles. The invention further relates to aqueous coating compositions comprising said particles. The invention further relates to particles obtained by a process comprising—amongst others—the steps of providing an aqueous dispersion comprising a particular (aziridinyl hydroxy)-functional organic component. The invention further relates to a kit-of-parts comprising in one of its parts an aqueous dispersion comprising a particular (aziridinyl hydroxy)-functional organic component. The invention further relates to cured forms of the various particles, mixtures, aqueous dispersions, aqueous compositions, coating compositions, and aqueous coating compositions. The invention further relates to articles comprising the particles and/or said mixtures, and/or said aqueous dispersions and/or aqueous compositions and/or said cured forms. The invention further relates to various uses of the particles and/or said mixtures, and/or said aqueous dispersions and/or aqueous compositions and/or kit-of-parts and/or said cured forms.

Several organic compounds bearing aziridine ring(s) (a 3-membered ring system composed of one nitrogen and two carbon atoms) are known in the art. Aziridines—which are three-membered cyclic amines (azacyclopropanes)—are an example of organic compounds bearing the aziridine ring. The ring-strain associated with these molecules makes them extremely reactive compounds and attractive for various industrial applications, e.g. as crosslinkers in paints and coating compositions. So far though, the employment of organic compounds bearing aziridine ring(s) in paints and coating compositions is administered via solutions of said compounds in volatile organic solvents since they are unstable in an aqueous environment. For example, the trimethylolpropane tris(2-methyl-1-aziridinepropionate (CAS No.: 64265-57-2; available by DSM as 'Crosslinker CX-100') and the pentaerythritol tris[3-(1-aziridinyl)propionate (CAS No.: 57116-45-7; available by Ichemco as 'XAMA®7'), as well as the pentaerythritol tris (3-(1-aziridinyl) propionate (CAS No.: 57116-45-7, available by LLC Aziridines as PZ-33) that are used as crosslinkers for carboxylic acid functional polymers at room temperature, are unstable in water; this instability in the water of these three organic compounds bearing aziridine ring(s) is described in U.S. Pat. No. 5,133,997. Hence, their employment cannot be extended to aqueous paints and coating compositions. This instability in the water is a significant drawback for organic compounds bearing aziridine ring(s) given the global technological and regulatory trends towards safer, healthier and environmentally friendlier paints and coating compositions, wherein aqueous coating compositions are at the forefront of these trends. Unless, a technical solution that would enable organic compounds bearing aziridine ring(s) to be administered and employed in aqueous environments and at the same time maintain a good crosslinking efficiency, these compounds face elimination from future industrial applications.

The US 2007/298006 A1 (equivalent to WO 2006/115547 A2) to Dendritic Nanotechnologies, PLLC disclosed dendritic polymers with enhanced amplification and interior functionality. The example 12 of the US 2007/298006 A1 disclosed a compound bearing an aziridine ring. This compound was the only compound bearing an aziridine ring that was disclosed in the US 2007/298006 A1. The compound of Example 12 of the US 2007/298006 A1 was obtained as a clear colourless oil, had a molecular weight of 588 Da, and it was used as a synthesis intermediate (via the aziridine ring-opening reaction) in the preparation of dendritic polymers. The US 2007/298006 A1 did neither disclose any particles—let alone any particles of compounds bearing aziridine group(s), let alone that these compounds had a molecular weight of at least 600 and at most 10000 Da—, nor any compositions, e.g. aqueous dispersions, comprising particles which particles comprised an (aziridinyl hydroxy)-functional organic component. The US 2007/298006 A1 was silent as to the combination of enhanced storage stability (at elevated temperature and for a prolonged time period; 4 weeks at 50° C.) of aqueous compositions, e.g. aqueous dispersions, comprising organic compounds bearing aziridine ring(s), maintaining good, preferably very good, more preferably excellent, crosslinking efficiency.

The EP 1865014 A1 to 3M Innovative Properties Company disclosed compositions comprising a prepolymer as component (A) wherein the prepolymer comprised aziridino groups. On page 8-14 (compounds 1-10), the EP 1865014 A1 disclosed compounds bearing aziridine groups. However, these compounds did not have—at least—a hydroxyl group connected to the 8-carbon atom as to the nitrogen atom of the aziridine group. Moreover, the compounds 1, 2, 3, 4, 9, 10 had an ester group connected to the aforementioned 8-carbon atom while the compounds 5, 6, 7, 8 methyl group connected to the aforementioned 8-carbon atom. Thus, the EP 1865014 A1 disclosed very different compounds bearing aziridine groups. Therefore, the EP 1865014 A1 did not only disclose very different compounds bearing aziridinyl groups, but it also did neither disclose any particles—let alone any particles of compounds bearing aziridine group(s), let alone that these compounds had a molecular weight of at least 600 and at most 10000 Da—, nor any compositions, e.g. aqueous dispersions, comprising particles which particles comprised an (aziridinyl hydroxy)-functional organic component. The EP 1865014 A1 was silent as to the combination of enhanced storage stability (at elevated temperature and for a prolonged time period; 4 weeks at 50° C.) of aqueous compositions, e.g. aqueous dispersions, comprising organic compounds bearing aziridine ring(s), maintaining good, preferably very good, more preferably excellent, crosslinking efficiency.

The WO 2015/066868 A1 to 3M Innovative Properties Company disclosed a fluoropolymer coating composition comprising an aqueous liquid medium, fluoropolymer particles dispersed in the aqueous liquid medium, and at least one aziridine compound. However, the aziridine compounds did not have—at least—a hydroxyl group connected to the 8-carbon atom as to the nitrogen atom of the aziridine group. Thus, the WO 2015/066868 A1 disclosed very different compounds bearing aziridine groups. Therefore, the WO 2015/066868 A1 did not only disclose very different compounds bearing aziridinyl groups, but it did neither disclose any particles of compounds bearing aziridine group(s), let alone that these compounds had a molecular weight of at least 600 and at most 10000 Da—, nor any compositions, e.g. aqueous dispersions comprising particles which particles comprised an (aziridinyl hydroxy) functional organic component. The WO 2015/066868 A1 was silent as to the combination of enhanced storage stability (at elevated temperature and for a prolonged time period; 4 weeks at 50° C.) of aqueous compositions e.g. aqueous dispersions comprising organic compounds bearing aziridine ring(s), maintaining good, preferably very good, more preferably excellent, crosslinking efficiency.

The U.S. Pat. No. 3,329,674 to Thiokol Chemical Corporation disclosed low molecular weight aziridinyl compounds. The molecular weight of these aziridinyl compounds was well below 600 Da (see examples 1-7; the molecular weight of these compounds varied from 304 to 526). The U.S. Pat. No. 3,329,674 did neither disclose any particles—let alone any particles of compounds bearing aziridine group(s), let alone that these compounds had a molecular weight of at least 600 and at most 10000 Da—, nor any compositions, e.g. aqueous dispersions, comprising particles which particles comprised an (aziridinyl hydroxy)-functional organic component. The U.S. Pat. No. 3,329,674 was silent as to the combination of enhanced storage stability (at elevated temperature and for a prolonged time period; 4 weeks at 50° C.) of aqueous compositions, e.g. aqueous dispersions, comprising organic compounds bearing aziridine ring(s), maintaining good, preferably very good, more preferably excellent, crosslinking efficiency.

The EP 0758662 A2 to Rockwell International Corporation disclosed curable resin systems comprising an epoxy resin, a co-reactant selected from N-alkyl and N-aryl substituted aziridines and a catalyst to promote cure at ambient temperature. In its example 3, the EP 0758662 A2 disclosed the reaction of PY 306 epoxy resin with 2-methylaziridine to afford an aziridine-endcapped organic compound as a viscous liquid. According to the EP 0758662 A2, the PY 306 epoxy resin is a bisphenol F epoxy supplied by Ciba Geigy (cf. EP 0758662 A2, from cl. 5, I.59 to cl. 6, I.1). This aziridine-endcapped organic compound was obtained as a viscous liquid and had a molecular weight of 426.25 Da (this is worked out from the stoichiometry of the reactants disclosed in the 1$^{st}$ sentence of Example 3 of the EP 0758662 A2), and it was used as a synthesis intermediate. The EP 0758662 A2 did neither disclose any particles—let alone any particles of compounds bearing aziridine group(s), let alone that these compounds had a molecular weight of at least 600 and at most 10000 Da—, nor any compositions, e.g. aqueous dispersions, comprising particles which particles comprised an (aziridinyl hydroxy)-functional organic component. The EP 0758662 A2 was silent as to the combination of enhanced storage stability (at elevated temperature and for a prolonged time period; 4 weeks at 50° C.) of aqueous compositions, e.g. aqueous dispersions, comprising organic compounds bearing aziridine ring(s), maintaining good, preferably very good, more preferably excellent, crosslinking efficiency.

Therefore, there is the desire for employing organic compounds bearing aziridine ring(s) in aqueous compositions, e.g. aqueous dispersions, aqueous coating compositions, for a prolonged time period and at elevated temperature, e.g. 4 weeks at 50° C., thus having enhanced storage stability and at the same time the organic compounds bearing aziridine ring(s) that are employed in said aqueous environment maintain good, preferably very good, more preferably excellent, crosslinking efficiency. In other words, there is the desire for employing organic compounds bearing aziridine ring(s) in aqueous compositions, e.g. aqueous dispersions, aqueous coating compositions, for a prolonged time period and at elevated temperature, e.g. 4 weeks at 50° C., thus having enhanced storage stability and at the same time the aqueous compositions e.g. aqueous dispersions, aqueous coating compositions, comprising organic compounds bearing the aziridine ring, maintain good, preferably very good, more preferably excellent, crosslinking efficiency.

However, the above desire still represents an unmet need since the solution to such a problem involving highly reactive organic compounds such as the organic compounds bearing aziridine ring(s), is particularly challenging.

Therefore, it is the object of the invention to provide for a solution to the above-mentioned unmet need. In other words, it is the object of the invention to provide for aqueous compositions, e.g. aqueous dispersions, aqueous coating compositions, comprising organic compounds bearing aziridine ring(s) wherein the aqueous compositions have enhanced storage stability for a prolonged time period and at elevated temperature (4 weeks at 50° C.), and at the same time the organic compounds bearing aziridine ring(s) that are employed in said aqueous environment maintain good, preferably very good, more preferably excellent—crosslinking efficiency (as the crosslinking efficiency is defined and determined in the specification); or equally, it is the object of the invention to provide for aqueous compositions e.g. aqueous dispersions, aqueous coating compositions, comprising organic compounds bearing aziridine ring(s) wherein the aqueous compositions have enhanced storage stability for a prolonged time period and at elevated temperature (4 weeks at 50° C.), and at the same time the aqueous compositions comprising organic compounds bearing the aziridine ring, maintain good, preferably very good, more preferably excellent—crosslinking efficiency (as the crosslinking efficiency is defined and determined in the specification).

This object was surprisingly achieved by using particles as described in the claims and as disclosed in the specification.

This object was surprisingly achieved by using aqueous dispersions (comprising the particles of the invention) as described in the claims and as disclosed in the specification.

More particularly, it has surprisingly been found that when the particles of the invention were used in aqueous dispersions, the latter had enhanced storage stability for a prolonged time period and at elevated temperature (4 weeks at 50° C.), and at the same time the organic compounds bearing aziridine ring(s) that were employed in said aqueous environment maintained good, preferably very good, more preferably excellent—crosslinking efficiency (as the crosslinking efficiency is defined and determined in the specification); or equally, it has surprisingly been found that when aqueous dispersions comprising organic compounds bearing aziridine ring(s) in particulate form, the aqueous compositions had enhanced storage stability for a prolonged time period and at elevated temperature (4 weeks at 50° C.), and at the same time the aqueous dispersions comprising organic compounds bearing aziridine ring(s) in particulate form, maintained good, preferably very good, more preferably excellent—crosslinking efficiency (as the crosslinking efficiency is defined and determined in the specification). The aqueous dispersions (or in general the aqueous compositions) of the invention are also easy to use, its aqueous nature yielding good compatibility with waterborne binders and hence good mixing and low fouling during formulation. Furthermore, these compositions generally have workable viscosities, resulting in facile handling and accurate dosing.

The particles of the invention may also have an array of further inventive uses depending on the way and the type of compositions or processes that they may be used. Some of their additional uses are disclosed in the specification.

The particles of the invention constitute a significant technological advancement for several industries where particulate materials, powders or bulk solids are used widely since they offer a variety of inventive advantages over the state-of-the-art. Exemplary industries include but are not limited to food processing, pharmaceutical, biotechnology, oil chemical, mineral processing, metallurgical, detergent, power generation, paints, plastics, inks, and adhesives 3D-printing, household, toiletries, and cosmetics industries. Also, the aqueous dispersions of the invention also constitute a significant technological advancement for several industries (especially that of paints, coatings, adhesives and inks) where the use of highly reactive reagents such as compounds bearing aziridine ring(s), is desired or is on-going. The reason being the aqueous dispersions of the invention offers concrete opportunities for the industries not only to pursue new and innovative products and processes but also to significantly improve on the safety, health and environmental profile of their operations, products and processes; the reason being the use of volatile organic solvents may be eliminated and the aqueous dispersions of the invention may easily and safely be stored and transported. At the same time aqueous dispersions of the invention offer a plethora of options to the paint formulator to design and produce both 1K (one-component) and 2K (two-component) paint formulations thus enhancing its freedom to formulate new and environmentally friendlier products. The enablement of 1K paint formulations is of extreme interest and technological advancement since they are generally preferred over the 2K paint formulations.

Broadly in accordance with the invention, there are provided particles as described in the claims and as disclosed in the specification.

Broadly in accordance with the invention, there are provided mixtures as described in the claims and as disclosed in the specification.

Broadly in accordance with the invention, there are provided aqueous dispersions as described in the claims and as disclosed in the specification.

Broadly in accordance with the invention, there are provided particles obtained by a process as described in the claims and as disclosed in the specification.

Broadly in accordance with the invention, there are provided aqueous compositions as described in the claims and as disclosed in the specification.

Broadly in accordance with the invention, there are provided kits-of-parts as described in the claims and as disclosed in the specification.

Broadly in accordance with the invention, there are provided cured forms as described in the claims and as disclosed in the specification.

Broadly in accordance with the invention, there are provided articles as described in the claims and as disclosed in the specification.

Broadly in accordance with the invention, there is provided a use of any one or any combination of the following:

i) particles as described in the claims and as disclosed in the specification;
ii) a mixture as described in the claims and as disclosed in the specification;
iii) an aqueous dispersion as described in the claims and as disclosed in the specification:
iv) particles obtained by a process as described in the claims and as disclosed in the specification;
v) an aqueous composition as described in the claims and as disclosed in the specification; as a crosslinker.

Broadly in accordance with the invention, there is provided a use of any one or any combination of the following:

i) particles as described in the claims and as disclosed in the specification;
ii) a mixture as described in the claims and as disclosed in the specification;
iii) an aqueous dispersion as described in the claims and as disclosed in the specification:
iv) particles obtained by a process as described in the claims and as disclosed in the specification;
v) an aqueous composition as described in the claims and as disclosed in the specification;
vi) a kit-of-parts as described in the claims and as disclosed in the specification;
vii) a cured form as described in the claims and as disclosed in the specification;
viii) an article as described in the claims and as disclosed in the specification;

in coatings, paints, inks, varnishes, lubricants, adhesives, additive manufacturing, 3D-printing, textiles, waxes, fuels, photography, plastics, medical compositions, medical devices.

A1a Broadly in accordance with the invention there are provided particles according to claim 1.

The following paragraphs A1 to A55 constitute certain explicit preferments of the particles according to A1a and certain further explicit aspects of the invention of the particles according to A1a. More specifically, the particles' preferments according to A1a include but are not limited to preferments A1 to A21, while the aspects of the invention of the particles according to A1a include but are not limited to aspects A22 to A55. Many other variations, combinations or embodiments of the invention are apparent to those skilled in the art and such variations, combinations and embodiments are contemplated within the scope of the claimed invention. The antecedent basis for certain terms shown in the preferments and the aspects can be found in preceding preferments or aspects. Any reference to components includes their preferments and preferred ranges as disclosed in the entire specification, including the claims.

A1 The particles according to A1a or any combination derived from the disclosure in section 1 and the entire specification, wherein the particles—preferably organic particles—comprise an (aziridinyl hydroxy)-functional organic component (AZ-component), and wherein the particles have a scatter intensity-based average hydrodynamic diameter ($D_H$) determined via dynamic light scattering according to the description, of at least 2 and at most 3000, preferably at least 2 and at most 2500, more preferably at least 2 and at most 2000, even more preferably at least 2 and at most 1500, for example at least 2 and at most 1000, for example at least 2 and at most 900, for example at least 2 and at most 800, for example at least 2 and at most 600, for example at least 2 and at most 500, for example at least 2 and at most 400, for example at least 2 and at most 350, for example at least 2 and at most 300, for example at least 10 and at most 3000, for example at least 10 and at most 2500, for example at least 10 and at most 2000, for example at least 10 and at most 1500, for example at least 10 and at most 1000, for example at least 10 and at most 900, for example at least 10 and at most 800, for example at least 10 and at most 600, for example at least 10 and at most 500, for example at least 10 and at most 400, for example at least 10 and at most 350, for example at least 10 and at most 300, for example at least 20 and at most 3000, for example at least 20 and at most 2500, for example at least 20 and at most 2000, for example at least 20 and at most 1500, for example at least 20 and at most 1000, for example at least 20 and at most 900, for example at least 20 and at most 800, for example at least 20 and at most 600, for example at least 20 and at most 500, for example at least 20 and at most 400, for example at least 20 and at most 350, for example at least 20 and at most 300, for example at least 30 and at most 3000, for example at least 30 and at most 2500, for example at least 30 and at most 2000, for example at least 30 and at most 1500, for example at least 30 and at most 1000, for example at least 30 and at most 900, for example at least 30 and at most 800, for example at least 30 and at most 600, for example at least 30 and at most 500, for example at least 30 and at most 400, for example at least 30 and at most 350, for example at least 30 and at most 300, for example at least 40 and at most 3000, for example at least 40 and at most 2500, for example at least 40 and at most 2000, for example at least 40 and at most 1500, for example at least 40 and at most 1000, for example at least 40 and at most 900, for example at least 40 and at most 800, for example at least 40 and at most 600, for example at least 40 and at most 500, for example at least 40 and at most 400, for example at least 40 and at most 350, for example at least 40 and at most 300, for example at least 50 and at most 3000, for example at least 50 and at most 2500, for example at least 50 and at most 2000, for example at least 50 and at most 1500, for example at least 50 and at most 1000, for example at least 50 and at most 900, for example at least 50 and at most 800, for example at least 50 and at most 600, for example at least 50 and at most 500, for example at least 50 and at most 400, for example at least 50 and at most 350, for example at least 50 and at most 300, for example at least 60 and at most 3000, for example at least 60 and at most 2500, for example at least 60 and at most 2000, for example at least 60 and at most 1500, for example at least 60 and at most 1000, for example at least 60 and at most 900, for example at least 60 and at most 800, for example at least 60 and at most 600, for example at least 60 and at most 500, for example at least 60 and at most 400, for example at least 60 and at most 350, for example at least 60 and at most 300, for example at least 70 and at most 3000, for example at least 70 and at most 2500, for example at least 70 and at most 2000, for example at least 70 and at most 1500, for example at least 70 and at most 1000, for example at least 70 and at most 900, for example at least 70 and at most 800, for example at least 70 and at most 600, for example at least 70 and at most 500, for example at least 70 and at most 400, for example at least 70 and at most 350, for example at least 70 and at most 300, for example at least 80 and at most 3000, for example at least 80 and at most 2500, for example at least 80 and at most 2000, for example at least 80 and at most 1500, for example at least 80 and at most 1000, for example at least 80 and at most 900, for example at least 80 and at most 800, for example at least 80 and at most 600, for example at least 80 and at most 500, for example at least 80 and at most 400, for example at least 80 and at most 350, for example at least 80 and at most 300, for example at least 90 and at most 3000, for example at least 90 and at most 2500, for example at least 90 and at most 2000, for example at least 90 and at most 1500, for example at least 90 and at most 1000, for example at least 90 and at most 900, for example at least 90 and at most 800, for example at least 90 and at most 600, for example at least 90 and at most 500, for example at least 90 and at most 400, for example at least 90 and at most 350, for example at least 90 and at most 300, for example at least 100 and at most 3000, for example at least 100 and at most 2500, for example at least 100 and at most 2000, for example at least 100 and at most 1500, for example at least 100 and at most 1000, for example at least 100 and at most 900, for example at least 100 and at most 800, for example at least 100 and at most 600, for example at least 100 and at most 500, for example at least 100 and at most 400, for example at least 100 and at most 350, for example at least 100 and at most 300 nm, and wherein the (aziridinyl hydroxy)-functional organic component (AZ-component) is selected from the group consisting of i) to vi): i) (aziridinyl hydroxy)-functional organic compound AZ1 of Formula A1 having only two aziridine rings (AZ1-compound), ii) (aziridinyl hydroxy)-functional organic compound AZ2 of Formula A2 having only three aziridine rings (AZ2-compound), iii) (aziridinyl hydroxy)-functional organic compound AZ3 of Formula A3 having only four aziridine rings (AZ3-compound), iv) (aziridinyl hydroxy)-functional organic compound AZ4 of Formula A4 having only five aziridine rings (AZ4-compound), v) (aziridinyl hydroxy)-functional organic compound AZ5 of Formula A5 having only six aziridine rings (AZ5-compound), and vi) mixtures thereof, preferably the AZ-component is selected from the group consisting of i) to iv): i) (aziridinyl hydroxy) functional organic compound AZ1 of Formula A1 having only two aziridine rings (AZ1-compound), ii) (aziridinyl hydroxy)-functional organic compound AZ2 of Formula A2 having only three aziridine rings (AZ2-compound), iii) (aziridinyl hydroxy)-functional organic compound AZ3 of Formula A3 having only four aziridine rings (AZ3-compound), and iv) mixtures thereof, Formula A1

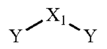

Formula A2

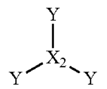

Formula A3

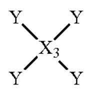

Formula A4

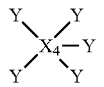

Formula A5

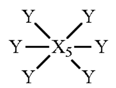

wherein $X_1$ is a bivalent aliphatic organic radical or a bivalent aromatic organic radical, preferably $X_1$ is a bivalent aliphatic organic radical;

$X_2$ is a trivalent aliphatic organic radical or a trivalent aromatic organic radical, preferably $X_2$ is a trivalent aliphatic organic radical;

$X_3$ is a quadrivalent aliphatic organic radical or a quadrivalent aromatic organic radical, preferably $X_3$ is a quadrivalent aliphatic organic radical;

$X_4$ is a pentavalent aliphatic organic radical or a pentavalent aromatic organic radical, preferably $X_4$ is a pentavalent aliphatic organic radical;

$X_5$ is a hexavalent aliphatic organic radical or a hexavalent aromatic organic radical, preferably $X_5$ is a hexavalent aliphatic organic radical;

and wherein each of the $X_1$ to $X_5$ consists of a collection of atoms covalently connected in a configuration that comprises—preferably consists of—linear and/or branched and/or ring structures, which collection of atoms is selected from the group consisting of i) to x):

i) carbon and hydrogen atoms, ii) carbon, hydrogen and oxygen atoms, iii) carbon, hydrogen and nitrogen atoms, iv) carbon, hydrogen and sulphur atoms, v) carbon, hydrogen, oxygen and nitrogen atoms, vi) carbon, hydrogen, nitrogen and sulphur atoms, vii) carbon, hydrogen, oxygen and sulphur atoms, viii) carbon, hydrogen, oxygen, nitrogen and sulphur, atoms, ix) carbon, hydrogen and silicon atoms, and x) carbon, hydrogen, oxygen and silicon atoms and xi) any combination of ix) and/or x) with any one or all of the iii) to viii), and wherein each of the $X_1$ to $X_5$ has carbon atoms and hydrogen atoms, and wherein each of the $X_1$ to $X_5$ has optionally oxygen atoms and/or nitrogen atoms and/or sulphur atoms and/or silicon atoms, and wherein the $X_1$, and/or the $X_2$ and/or the $X_3$ and/or the $X_4$ and/or the $X_5$ may optionally comprise an ionic functional group, preferably the $X_1$, and/or the $X_2$ and/or the $X_3$ and/or the $X_4$ and/or the $X_5$ does not comprise an ionic functional group, and wherein Y is a monovalent organic radical selected from the group consisting of: i) monovalent (aziridinyl hydroxyisopropyl) organic radical of Formula B1, ii) monovalent (aziridinyl hydroxycyclohexane) organic radical of Formula B2, and iii) monovalent (aziridinyl hydroxycyclohexane) organic radical of Formula B3, preferably Y is a monovalent (aziridinyl hydroxyisopropyl) organic radical of Formula B1, Formula B1

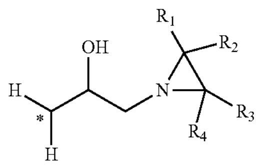

Formula B2

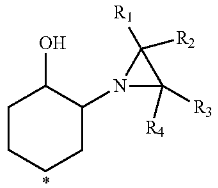

-continued

Formula B3

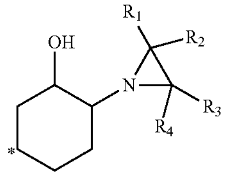

and wherein $R_1$ is selected from the group consisting of hydrogen and methyl; and $R_2$ is selected from the group consisting of hydrogen, methyl, and $C_2$-$C_5$ alkyl; and $R_3$ is selected from the group consisting of methyl, and $C_2$-$C_4$ alkyl; and $R_4$ is selected from the group consisting of hydrogen, methyl, and $C_2$-$C_4$ alkyl; and wherein the Y in each of the compounds A1 to A5 may be the same or different to each other and wherein each of the single covalent bonds between the Y and each one of the $X_1$ to $X_5$ is selected from the group consisting of carbon-carbon single bond, carbon-oxygen single bond and carbon-nitrogen single bond, preferably carbon-oxygen single bond and carbon-nitrogen single bond, more preferably carbon-oxygen single bond, and wherein each of the AZ1- to AZ5-compound has a molecular weight determined via MALDI-TOF MS according to the description, of at least 600 and at most 10000 Da.

A2 The particles according to any one of A1a or A1 or any combination derived from the disclosure in section 1 and the entire specification, wherein the particles comprise at least 20, preferably at least 40, more preferably at least 55, even more preferably at least 70, for example at least 82, for example at least 85, for example at least 89, for example at least 93, for example at least 96, for example at least 99 wt % of the (aziridinyl hydroxy)-functional organic component (AZ-component).

A3 The particles according to A1a or to any one of A1 to A2 or any combination derived from the disclosure in section 1 and the entire specification, wherein each of the AZ1- to AZ5-compound has a molecular weight of at least 600 and at most 8000, preferably at least 600 and at most 7000, more preferably at least 600 and at most 6000, for example at least 600 and at most 5500, for example at least 600 and at most 5000, for example at least 600 and at most 4000, for example at least 600 and at most 3500, for example at least 600 and at most 3200, for example at least 600 and at most 3000, for example at least 600 and at most 2500, for example at least 600 and at most 2200, for example at least 600 and at most 2000, for example at least 630 and at most 10000, preferably at least 630 and at most 8000, more preferably at least 630 and at most 7000, even more preferably at least 630 and at most 6000, for example at least 630 and at most 5500, for example at least 630 and at most 5000, for example at least 630 and at most 4000, for example at least 630 and at most 3500, for example at least 630 and at most 3200, for example at least 630 and at most 3000, for example at least 630 and at most 2500, for example at least 630 and at most 2200, for example at least 630 and at most 2000, for example at least 640 and at most 10000, for example at least 640 and at most 8000, for example at least 640 and at most 7000, for example at least 640 and at most 6000, for example at least 640 and at most 5500, for example at least 640 and at most 5000, for example at least 640 and at most 4000, for example at least 640 and at most 3500, for example at least 640 and at most 3200, for example at least 640 and at most 3000, for example at least 640 and at most 2500, for example at least 640 and at most 2200, for example at least 640 and at most 2000, for example at least 650 and at most 10000, for example at least 650 and at most 8000, for example at least 650 and at most 7000, for example at least 650 and at most 6000, for example at least 650 and at most 5500, for example at least 650 and at most 5000, for example at least 650 and at most 4000, for example at least 650 and at most 3500, for example at least 650 and at most 3200, for example at least 650 and at most 3000, for example at least 650 and at most 2500, for example at least 650 and at most 2200, for example at least 650 and at most 2000, for example at least 700 and at most 10000, for example at least 700 and at most 8000, for example at least 700 and at most 7000, for example at least 700 and at most 6000, for example at least 700 and at most 5500, for example at least 700 and at most 5000, for example at least 700 and at most 4000, for example at least 700 and at most 3500, for example at least 700 and at most 3200, for example at least 700 and at most 3000, for example at least 700 and at most 2500, for example at least 700 and at most 2200, for example at least 700 and at most 2000, for example at least 750 and at most 10000, for example at least 750 and at most 8000, for example at least 750 and at most 7000, for example at least 750 and at most 6000, for example at least 750 and at most 5500, for example at least 750 and at most 5000, for example at least 750 and at most 4000, for example at least 750 and at most 3500, for example at least 750 and at most 3200, for example at least 750 and at most 3000, for example at least 750 and at most 2500, for example at least 750 and at most 2200, for example at least 750 and at most 2000, for example at least 800 and at most 10000, for example at least 800 and at most 8000, for example at least 800 and at most 7000, for example at least 800 and at most 6000, for example at least 800 and at most 5500, for example at least 800 and at most 5000, for example at least 800 and at most 4000, for example at least 800 and at most 3500, for example at least 800 and at most 3200, for example at least 800 and at most 3000, for example at least 800 and at most 2500, for example at least 800 and at most 2200, for example at least 800 and at most 2000, for example at least 850 and at most 10000, for example at least 850 and at most 8000, for example at least 850 and at most 7000, for example at least 850 and at most 6000, for example at least 850 and at most 5500, for example at least 850 and at most 5000, for example at least 850 and at most 4000, for example at least 850 and at most 3500, for example at least 850 and at most 3200, for example at least 850 and at most 3000, for example at least 850 and at most 2500, for example at least 850 and at most 2200, for example at least 850 and at most 2000, for example at least 900 and at most 10000, for example at least 900 and at most 8000, for example at least 900 and at most 7000, for example at least 900 and at most 6000, for example at least 900 and at most 5500, for example at least 900 and at most 5000, for example at least 900 and at most 4000, for example at least 900 and at most 3500, for example at least 900 and at most 3200, for example at least 900 and at most 3000, for example at least 900 and at most 2500, for example at least 900 and at most 2200, for example at least 900 and at most 2000, for example at least 950 and at most 10000, for example at least 950 and at most 8000, for example at least 950 and at most 7000, for example at least 950 and at most 6000, for example at least 950 and at most 5500, for example at least 950 and at most 5000, for example at least 950 and at most 4000, for example at least 950 and at most 3500, for example at least 950 and at most 3200, for example at least 950 and at most 3000, for example at least 950 and at most 2500, for example at least 950 and at most 2200, for example at least 950 and at most 2000, for example at least 1000 and at most 10000, for example at least 1000 and at most 8000, for example at least 1000 and at most 7000, for example at least 1000 and at most 6000, for example at least 1000 and at most 5500, for example at least 1000 and at most 5000, for example at least 1000 and at most 4000, for example at least 1000 and at most 3500, for example at least 1000 and at most 3200, for example at least 1000 and at most 3000, for example at least 1000 and at most 2500, for example at least 1000 and at most 2200, for example at least 1000 and at most 2000, for example at least 1100 and at most 10000, for example at least 1100 and at most 8000, for example at least 1100 and at most 7000, for example at least 1100 and at most 6000, for example at least 1100 and at most 5500, for example at least 1100 and at most 5000, for example at least 1100 and at most 4000, for example at least 1100 and at most 3500, for example at least 1100 and at most 3200, for example at least 1100 and at most 3000, for example at least 1100 and at most 2500, for example at least 1100 and at most 2200, for example at least 1100 and at most 2000, for example at least 1200 and at most 10000, for example at least 1200 and at most 8000, for example at least 1200 and at most 7000, for example at least 1200 and at most 6000, for example at least 1200 and at most 5500, for example at least 1200 and at most 5000, for example at least 1200 and at most 4000, for example at least 1200 and at most 3500, for example at least 1200 and at most 3200, for example at least 1200 and at most 3000, for example at least 1200 and at most 2500, for example at least 1200 and at most 2200, for example at least 1200 and at most 2000 Da.

A4 The particles according to A1a or any one of A1 to A3 or any combination derived from the disclosure in section 1 and the entire specification, wherein the $X_1$ is a bivalent aliphatic organic radical or a bivalent aromatic organic radical other than a bivalent radical of bisphenol A.

A5 The particles according to A1a or to any one of A1 to A4 or any combination derived from the disclosure in section 1 and the entire specification, wherein the $X_1$ is a bivalent aliphatic organic radical or a bivalent aromatic organic radical other than a bivalent organic radical selected from the group consisting of bivalent radical of bisphenol A, bivalent radical of bisphenol AP, bivalent radical of bisphenol AF, bivalent radical of bisphenol B, bivalent radical of bisphenol BP, bivalent radical of bisphenol C, bivalent radical of bisphenol C2, bivalent radical of bisphenol E, bivalent radical of bisphenol F, bivalent radical of bisphenol G, bivalent radical of bisphenol M, bivalent radical of bisphenol S, bivalent radical of bisphenol P, bivalent radical of bisphenol PH, bivalent radical of bisphenol TMC, bivalent radical of bisphenol Z, bivalent radical of dinitrobisphenol A, bivalent radical of tetrabromobisphenol A, and combinations thereof, preferably $X_1$ is a bivalent aliphatic organic radical.

A6 The particles according to A1a or any one of A1 to A5 or any combination derived from the disclosure in section 1 and the entire specification, wherein the $X_1$, and/or the $X_2$ and/or the $X_3$ and/or the $X_4$ and/or the $X_5$ comprises at least one structural unit or a combination of structural units selected from the group consisting of unit 1, unit 2, unit 3, unit 4, unit 5, unit 6, unit 7, unit 8, unit 9, unit 10, and unit 11, preferably comprises at least one structural unit or a combination of structural units selected from the group consisting of unit 1, unit 4, unit 9, unit 10 and unit 11, as the units 1 to 11 are depicted below:

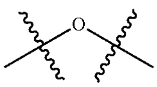
unit 1

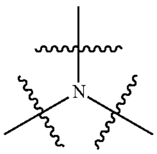
unit 2

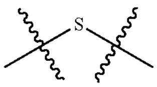
unit 3

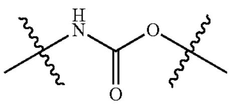
unit 4

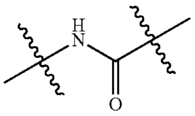
unit 5

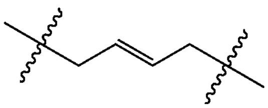
unit 6

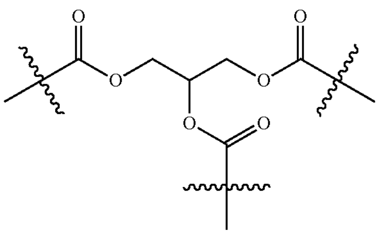
unit 7

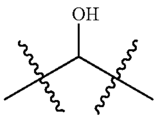
unit 8

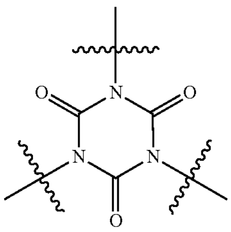
unit 9

-continued

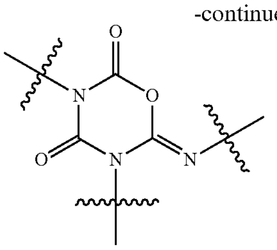
unit 10

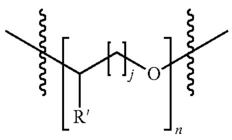
unit 11 wherein

R' is selected from the group consisting of hydrogen and methyl; and j is an integer ranging from 1 to 5, preferably from 1 to 3; and n is an integer ranging from and including 2 up to and including 50, preferably from and including 2 up to and including 40, more preferably from and including 2 up to and including 30, most preferably from and including 2 up to and including 20, for example from and including 2 up to and including 15, for example from and including 2 up to and including 10, for example from and including 2 up to and including 5, for example the n is 2, for example from and including 3 up to and including 50, for example from and including 3 up to and including 40, for example from and including 3 up to and including 30, for example from and including 3 up to and including 20, for example from and including 3 up to and including 15, for example from and including 3 up to and including 10, for example from and including 3 up to and including 5, for example the n is 3, for example from and including 4 up to and including 50, for example from and including 4 up to and including 40, for example from and including 4 up to and including 30, for example from and including 4 up to and including 20, for example from and including 4 up to and including 15, for example from and including 4 up to and including 10, for example from and including 4 up to and including 5, for example the n is 4, for example from and including 5 up to and including 50, for example from and including 5 up to and including 40, for example from and including 5 up to and including 30, for example from and including 5 up to and including 20, for example from and including 5 up to and including 15, for example from and including 5 up to and including 10, for example the n is 5, for example from and including 6 up to and including 50, for example from and including 6 up to and including 40, for example from and including 6 up to and including 30, for example from and including 6 up to and including 20, for example from and including 6 up to and including 15, for example from and including 6 up to and including 10, for example the n is 6, for example from and including 7 up to and including 50, for example from and including 7 up to and including 40, for example from and including 7 up to and including 30, for example from and including 7 up to and including 20, for example from and including 7 up to and including 15, for example from and including 7 up to and including 10, for example the n is 7, for example from and including 8 up to and including 50, for example from and including 8 up to and including 40, for example from and including 8 up to and including 30, for example from and including 8 up to and including 20, for example from and including 8 up to and including 15, for example from and including 8 up to and including 10, for example the n is 8, for example from and including 9 up to and including 50, for example from and including 9 up to and including 40, for example from and including 9 up to and including 30, for example from and including 9 up to and including 20, for example from and including 9 up to and including 15, for example from and including 9 up to and including 10, for example the n is 9, for example from and including 10 up to and including 50, for example from and including 10 up to and including 40, for example from and including 10 up to and including 30, for example from and including 10 up to and including 20, for example from and including 10 up to and including 15, for example the n is 10.

A7 The particles according to A1a or any one of A1 to A6 or any combination derived from the disclosure in section 1 and the entire specification, wherein $R_1$ is selected from the group consisting of hydrogen and methyl; and $R_2$ is selected from the group consisting of hydrogen, methyl, and ethyl; and $R_3$ is selected from the group consisting of methyl, and $C_2$-$C_4$ alkyl; and $R_4$ is selected from the group consisting of hydrogen, methyl, and ethyl.

A8 The particles according to A1a or any one of A1 to A7 or any combination derived from the disclosure in section 1 and the entire specification, wherein the aggregate number of carbon atoms in $R_1$, and $R_2$ and $R_3$ and $R_4$ is at most 9, preferably at most 4, more preferably at most 2, for example at most 1.

A9 The particles according to A1a or to any one of A1 to A8 or any combination derived from the disclosure in section 1 and the entire specification, wherein the $X_1$ and/or the $X_2$ and/or the $X_3$ and/or the $X_4$ and/or the $X_5$ does not contain one or any combination of the following structural units BP1, BP2, BP3, and BS unit BP1

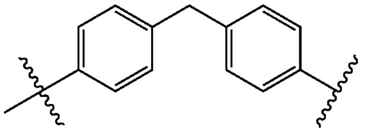

unit BP2

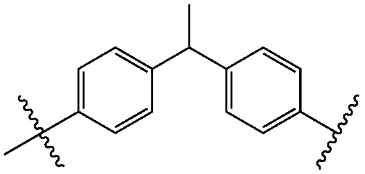

unit BP3

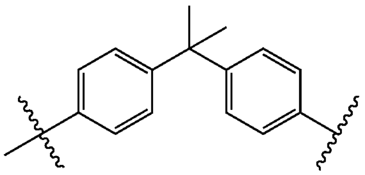

-continued unit BS

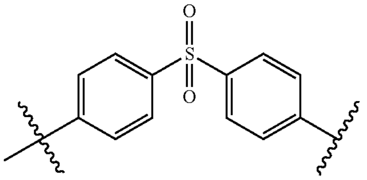

A10 The particles according to A1a or any one of A1 to A9 or any combination derived from the disclosure in section 1 and the entire specification, wherein the $X_1$, and/or the $X_2$ and/or the $X_3$ and/or the $X_4$ and/or the $X_5$ comprises at least one unit 11 as a structural unit.

A11 The particles according to A1a or to any one of A1 to A10 or any combination derived from the disclosure in section 1 and the entire specification, wherein the $X_1$ is the bivalent aliphatic organic radical of Formula A1a'

Formula A1a'

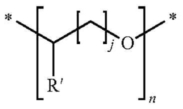

wherein

R' is selected from the group consisting of hydrogen and methyl; and j is an integer ranging from 1 to 5, preferably from 1 to 3; and n is an integer ranging from and including 2 up to and including 50, preferably from and including 2 up to and including 40, more preferably from and including 2 up to and including 30, most preferably from and including 2 up to and including 20, for example from and including 2 up to and including 15, for example from and including 2 up to and including 10, for example from and including 2 up to and including 5, for example the n is 2, for example from and including 3 up to and including 50, for example from and including 3 up to and including 40, for example from and including 3 up to and including 30, for example from and including 3 up to and including 20, for example from and including 3 up to and including 15, for example from and including 3 up to and including 10, for example from and including 3 up to and including 5, for example the n is 3, for example from and including 4 up to and including 50, for example from and including 4 up to and including 40, for example from and including 4 up to and including 30, for example from and including 4 up to and including 20, for example from and including 4 up to and including 15, for example from and including 4 up to and including 10, for example from and including 4 up to and including 5, for example the n is 4, for example from and including 5 up to and including 50, for example from and including 5 up to and including 40, for example from and including 5 up to and including 30, for example from and including 5 up to and including 20, for example from and including 5 up to and including 15, for example from and including 5 up to and including 10, for example the n is 5, for example from and including 6 up to and including 50, for example from and including 6 up to and including 40, for example from and including 6 up to and including 30, for example from and including 6 up to and including 20, for example from and including 6 up to and including 15, for example from and including 6 up to and including 10, for example the n is 6, for example from and including 7 up to and including 50, for example from and including 7 up to and including 40, for example from and including 7 up to and including 30, for example from and including 7 up to and including 20, for example from and including 7 up to and including 15, for example from and including 7 up to and including 10, for example the n is 7, for example from and including 8 up to and including 50, for example from and including 8 up to and including 40, for example from and including 8 up to and including 30, for example from and including 8 up to and including 20, for example from and including 8 up to and including 15, for example from and including 8 up to and including 10, for example the n is 8, for example from and including 9 up to and including 50, for example from and including 9 up to and including 40, for example from and including 9 up to and including 30, for example from and including 9 up to and including 20, for example from and including 9 up to and including 15, for example from and including 9 up to and including 10, for example the n is 9, for example from and including 10 up to and including 50, for example from and including 10 up to and including 40, for example from and including 10 up to and including 30, for example from and including 10 up to and including 20, for example from and including 10 up to and including 15, for example the n is 10.

A12 The particles according to A1a or to any one of A1 to A11 or any combination derived from the disclosure in section 1 and the entire specification, wherein each of the $X_1$ to $X_5$ contains only single covalent bonds, or both single and double covalent bonds, and wherein the single covalent bonds are selected from the group consisting of carbon-carbon single bond, carbon-hydrogen single bond, carbon-nitrogen single bond, carbon-sulphur single bond, carbon-silicon single bond, silicon-oxygen single bond, nitrogen-hydrogen single bond, sulphur-oxygen single bond, carbon-oxygen single bond wherein the oxygen is bonded to a hydrogen forming a hydroxyl group, silicon-oxygen-silicon single bonds, and wherein the double covalent bonds are selected from the group consisting of carbon-carbon double bond, carbon-nitrogen double bond, sulphur-oxygen double bond, carbon-oxygen double bond.

A13 The particles according to A1a or to any one of A1 to A12 or any combination derived from the disclosure in section 1 and the entire specification, wherein each of the $X_1$ to $X_5$ contains only single covalent bonds, or both single and double covalent bonds, and wherein the single covalent bonds are selected from the group consisting of carbon-carbon single bond, carbon-hydrogen single bond, carbon-nitrogen single bond, carbon-sulphur single bond, carbon-silicon single bond, silicon-oxygen single bond, nitrogen-hydrogen single bond, sulphur-oxygen single bond, carbon-oxygen single bond wherein the oxygen is bonded to a hydrogen forming a hydroxyl group, silicon-oxygen-silicon single bonds, and wherein the double covalent bonds are selected from the group consisting of carbon-carbon double bond, carbon-nitrogen double bond, sulphur-oxygen double bond, carbon-oxygen double bond wherein the carbon is a member of a ring structure, and carbon-oxygen double bond wherein the carbon is bonded to another two carbons via carbon-carbon single bonds, carbon-oxygen double bond wherein the carbon is bonded to another oxygen via single bond and to a nitrogen via a single bond, carbon-oxygen double bond wherein the carbon is bonded to two nitrogens via carbon-nitrogen single bonds, carbon-oxygen double bond wherein the carbon is bonded to another two oxygens via single bonds.

A14 The particles according to A1a or to any one of A1 to A13 or any combination derived from the disclosure in section 1 and the entire specification, wherein the aggregate number of carbon and hydrogen atoms in $X_1$ and/or $X_2$ and/or $X_3$ and/or $X_4$ and/or $X_5$ is at least 5, preferably at least 10, more preferably at least 15, most preferably at least 20, for example at least 25, for example at least 30, for example at least 35, for example at least 40, for example at least 45, for example at least 50, for example at least 55, for example at least 60, for example at least 65, for example at least 70, for example at least 75, for example at least 80, for example at least 85, for example at least 90, for example at least 95, for example at least 97, for example at least 98, for example at least 99, for example 100% as to the aggregate number of all the atoms present in $X_1$ and/or $X_2$ and/or $X_3$ and/or $X_4$ and/or $X_5$ respectively.

A15 The particles according to A1a or to any one of A1 to A14 or any combination derived from the disclosure in section 1 and the entire specification, wherein the aggregate number of all the atoms present in $X_1$ and/or $X_2$ and/or $X_3$ and/or $X_4$ and/or $X_5$ is at most 600, preferably at most 550, more preferably at most 500, most preferably at most 450, for examples at most 400, for example at most 350, for example at most 300, for example at most 250, for example at most 200.

A16 The particles according to A1a or to any one of A1 to A15 or any combination derived from the disclosure in section 1 and the entire specification, wherein the AZ-component is selected from the group consisting of i) to v): i) (aziridinyl hydroxy) functional organic compound AZ1 of Formula A1 (AZ1-compound), ii) (aziridinyl hydroxy)-functional organic compound AZ2 of Formula A2 (AZ2-compound), iii) (aziridinyl hydroxy)-functional organic compound AZ3 of Formula A3 (AZ3-compound), iv) (aziridinyl hydroxy)-functional organic compound AZ5 of Formula A5 (AZ5-compound), and vi) mixtures thereof, and wherein the AZ1-compound is selected from the group consisting of compounds having the Formula A1a, and compounds having the Formula A1 b, as each of these Formulae A1a-A1 d is described below Formula A1a

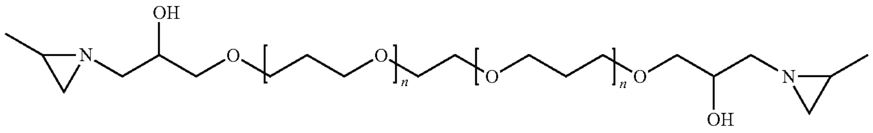

wherein each of the n in Formula A1a is independently selected, and each of the n in Formula A1a is an integer ranging from and including 2 up to and including 20, preferably from and including 2 up to and including 10, more preferably from and including 2 up to and including 7, most preferably from and including 2 up to and including 5, for example from and including 2 up to and including 4, for example from and including 3 up to and including 20, for example from and including 3 up to and including 10, for example from and including 3 up to and including 7, for example from and including 3 up to and including 5, for example from and including 3 up to and including 4, for example n is equal to 4; and Formula A1b

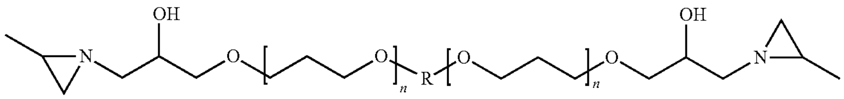

wherein the R in Formula A1 b is a $C_3$-$C_{10}$ saturated hydrocarbylene, and wherein each of the n in Formula Alb is independently selected and each of the n in Formula A1a is an integer ranging from and including 2 up to and including 20, preferably from and including 2 up to and including 10, more preferably from and including 2 up to and including 7, most preferably from and including 2 up to and including 5, for example from and including 2 up to and including 4, for example from and including 3 up to and including 20, for example from and including 3 up to and including 10, for example from and including 3 up to and including 7, for example from and including 3 up to and including 5, for example from and including 3 up to and including 4, for example n is equal to 4; and Formula A1c

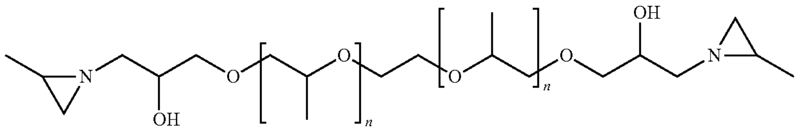

wherein each of the n in Formula A1c is independently selected, and each of the n in Formula A1 b is an integer ranging from and including 2 up to and including 20, preferably from and including 2 up to and including 10, more preferably from and including 2 up to and including 7, most preferably from and including 2 up to and including 5, for example from and including 2 up to and including 4, for example from and including 3 up to and including 20, for example from and including 3 up to and including 10, for example from and including 3 up to and including 7, for example from and including 3 up to and including 5, for example from and including 3 up to and including 4, for example n is equal to 4, and Formula A1d

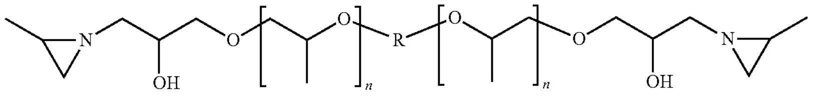

wherein the R in Formula A1 d is a $C_3$-$C_{10}$ saturated hydrocarbylene, and wherein each of the n in Formula A1 d is independently selected and each of the n in Formula Alb is an integer ranging from and including 2 up to and including 20, preferably from and including 2 up to and including 10, more preferably from and including 2 up to and including 7, most preferably from and including 2 up to and including 5, for example from and including 2 up to and including 4, for example from and including 3 up to and including 20, for example from and including 3 up to and including 10, for example from and including 3 up to and including 7, for example from and including 3 up to and including 5, for example from and including 3 up to and including 4, for example n is equal to 4, and wherein the AZ2-compound is selected from the group consisting of compounds having the Formula A2a, compounds having the Formula A2b, compounds having the Formula A2c, compounds having the Formula A2d, compounds having the Formula A2e, as each of these Formulae A2a-A2e is described below Formula A2a

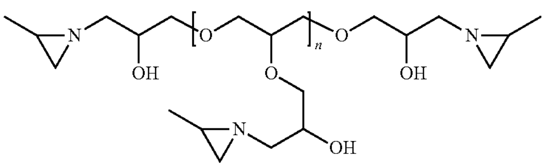

wherein the n in Formula A2a is an integer ranging from and including 2 up to and including 20, for example from and including 2 up to and including 10, for example from and including 2 up to and including 8, for example from and including 3 up to and including 20, for example from and including 3 up to and including 10, for example from and including 3 up to and including 8, for example from and including 4 up to and including 20, for example from and including 4 up to and including 10, for example from and including 4 up to and including 8, for example from and including 5 up to and including 20, for example from and including 5 up to and including 10, for example from and including 5 up to and including 8, for example from and including 6 up to and including 20, for example from and including 6 up to and including 10, for example from and including 6 up to and including 8, for example n is equal to 7; and Formula A2b

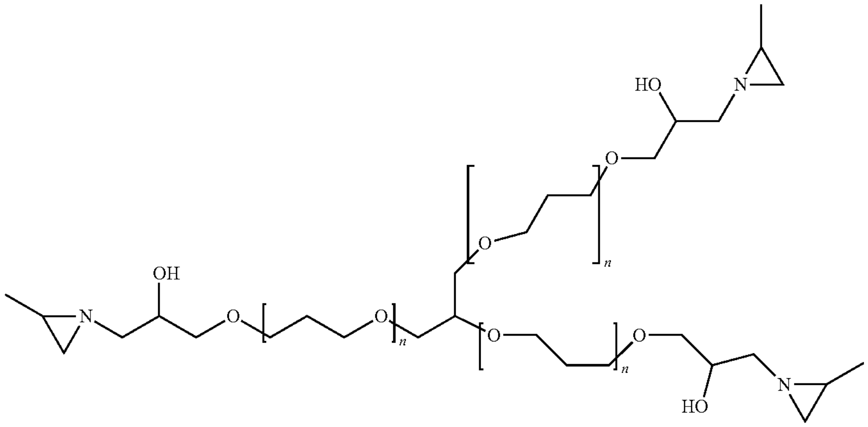

wherein each of the n in Formula A2b is independently selected and each of the n in Formula A2b is an integer ranging from and including 2 up to and including 20, preferably from and including 2 up to and including 15, more preferably from and including 2 up to and including 12, most preferably from and including 2 up to and including 11, for example from and including 3 up to and including 20, for example from and including 3 up to and including 15 for example from and including 3 up to and including 12 for example from and including 3 up to and including 11, for example from and including 4 up to and including 20, for example from and including 4 up to and including 15 for example from and including 4 up to and including 12 for example from and including 4 up to and including 11, for example from and including 5 up to and including 20, for example from and including 5 up to and including 15 for example from and including 5 up to and including 12 for example from and including 5 up to and including 11, for example from and including 6 up to and including 20, for example from and including 6 up to and including 15 for example from and including 6 up to and including 12 for example from and including 6 up to and including 11, for example from and including 7 up to and including 20, for example from and including 7 up to and including 15 for example from and including 7 up to and including 12 for example from and including 7 up to and including 11, for example from and including 8 up to and including 20, for example from and including 8 up to and including 15 for example from and including 8 up to and including 12 for example from and including 8 up to and including 11, for example from and including 9 up to and including 20, for example from and including 9 up to and including 15 for example from and including 9 up to and including 12 for example from and including 9 up to and including 11, for example from and including 10 up to and including 20, for example from and including 10 up to and including 15 for example from and including 10 up to and including 12 for example from and including 10 up to and including 11, for example n is equal to 11;

Formula A2c

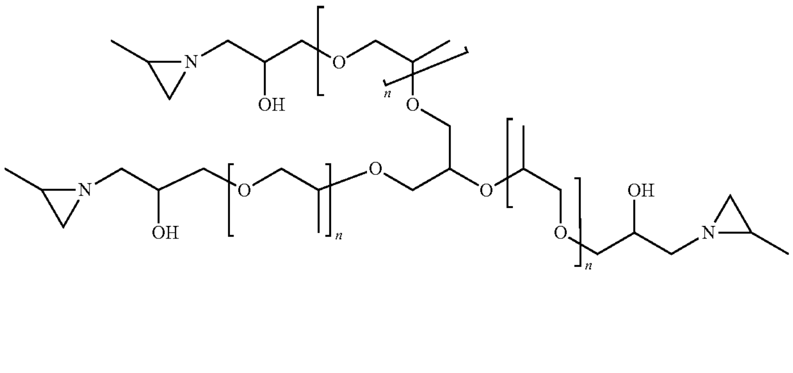

wherein each of the n in Formula A2c is independently selected and each of the n in Formula A2c is an integer ranging from and including 2 up to and including 20, preferably from and including 2 up to and including 15, more preferably from and including 2 up to and including 12, most preferably from and including 2 up to and including 11, for example from and including 3 up to and including 20, for example from and including 3 up to and including 15 for example from and including 3 up to and including 12 for example from and including 3 up to and including 11, for example from and including 4 up to and including 20, for example from and including 4 up to and including 15 for example from and including 4 up to and including 12 for example from and including 4 up to and including 11, for example from and including 5 up to and including 20, for example from and including 5 up to and including 15 for example from and including 5 up to and including 12 for example from and including 5 up to and including 11, for example from and including 6 up to and including 20, for example from and including 6 up to and including 15 for example from and including 6 up to and including 12 for example from and including 6 up to and including 11, for example from and including 7 up to and including 20, for example from and including 7 up to and including 15 for example from and including 7 up to and including 12 for example from and including 7 up to and including 11, for example from and including 8 up to and including 20, for example from and including 8 up to and including 15 for example from and including 8 up to and including 12 for example from and including 8 up to and including 11, for example from and including 9 up to and including 20, for example from and including 9 up to and including 15 for example from and including 9 up to and including 12 for example from and including 9 up to and including 11, for example from and including 10 up to and including 20, for example from and including 10 up to and including 15 for example from and including 10 up to and including 12 for example from and including 10 up to and including 11, for example n is equal to 11; and Formula A2d

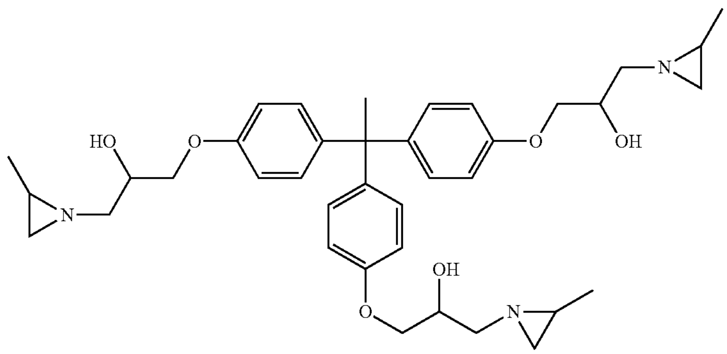

and

Formula A2e

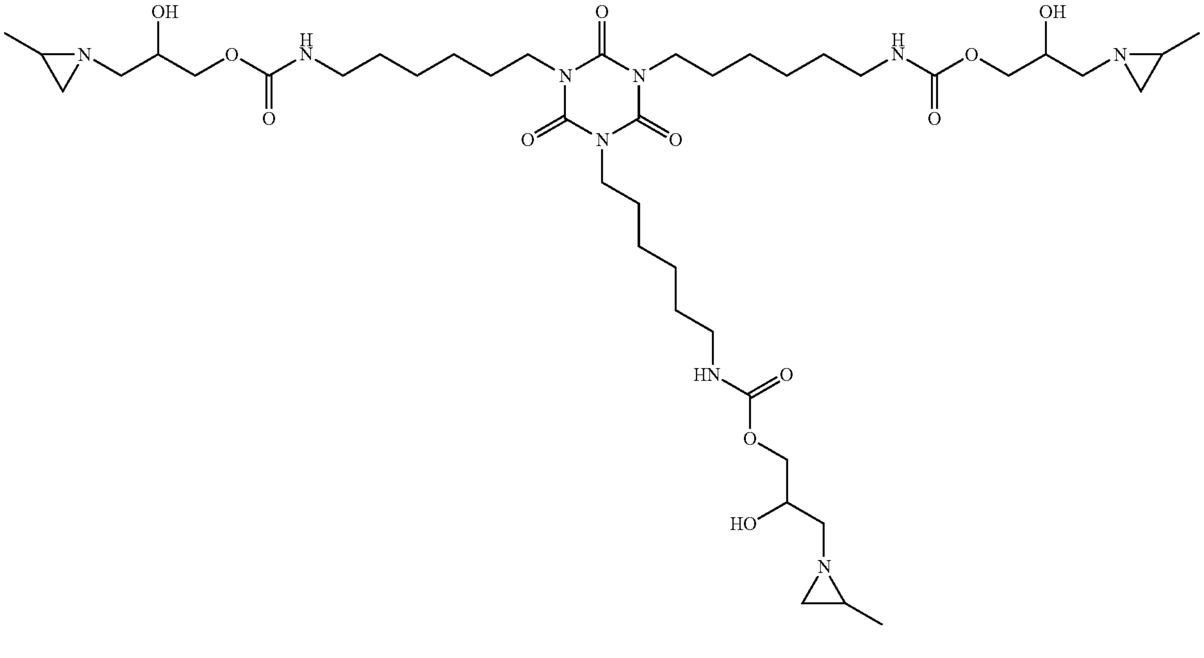

and wherein the AZ3-compound is selected from the group consisting of compounds having the Formula A3a Formula A3a

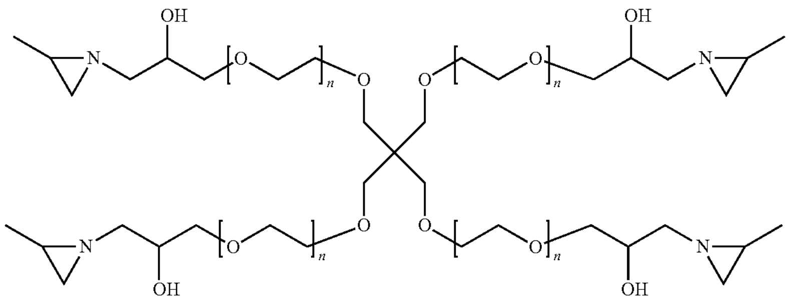

wherein each of the n in Formula A3a is independently selected, and each of the n in Formula A3a is an integer ranging from and including 2 up to and including 20, preferably from and including 2 up to and including 15, more preferably from and including 2 up to and including 10, most preferably from and including 2 up to and including 9, for example from and including 2 up to and including 8, for example from and including 2 up to and including 7, for example from and including 2 up to and including 6, for example from and including 2 up to and including 5, for example from and including 2 up to and including 4, for example from and including 2 up to and including 3, for example n is equal to 3, for example n is equal to 2;

and wherein the AZ5-compound is selected from the group consisting of compounds having the Formula A5a Formula A5a

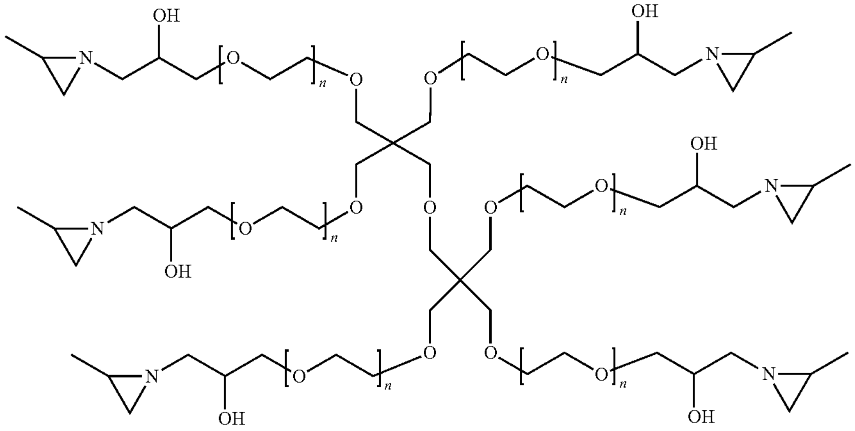

wherein each of the n in Formula A5a is independently selected and each of the n in Formula A5a is an integer ranging from and including 2 up to and including 40, preferably from and including 2 up to and including 30, more preferably from and including 2 up to and including 20, most preferably from and including 2 up to and including 10, for example from and including 2 up to and including 9, for example from and including 2 up to and including 8, for example from and including 2 up to and including 7, for example from and including 2 up to and including 6, for example from and including 2 up to and including 5, for example from and including 2 up to and including 4, for example from and including 3 up to and including 40, for example from and including 3 up to and including 30, for example from and including 3 up to and including 20, for example from and including 3 up to and including 10, for example from and including 3 up to and including 9, for example from and including 3 up to and including 8, for example from and including 3 up to and including 7, for example from and including 3 up to and including 6, for example from and including 3 up to and including 5, for example from and including 3 up to and including 4, for example n is equal to 4, for example n is equal to 3.

A17 The particles according to A1a or to any one of A1 to A16 or any combination derived from the disclosure in section 1 and the entire specification, wherein the $X_1$ and/or the $X_2$ and/or the $X_3$ and/or the $X_4$ and/or the $X_5$ does not contain any structural unit of (or equally derived from) phenol formaldehyde resins (also known as phenolic resins); examples of phenol-formaldehyde (PF) resins include novolacs (acid-catalyzed PF resins with a formaldehyde to phenol ratio of equal to or lower than one), and resols (base-catalyzed PF resins with a formaldehyde to phenol ratio of greater than one, usually equal to 1.5).

A18 The particles according to A1a or to any one of A1 to A17 or any combination derived from the disclosure in section 1 and the entire specification, wherein the AZ-component is selected from the group consisting of AZ1-compound and wherein the AZ1-compound is the compound of the following formula,

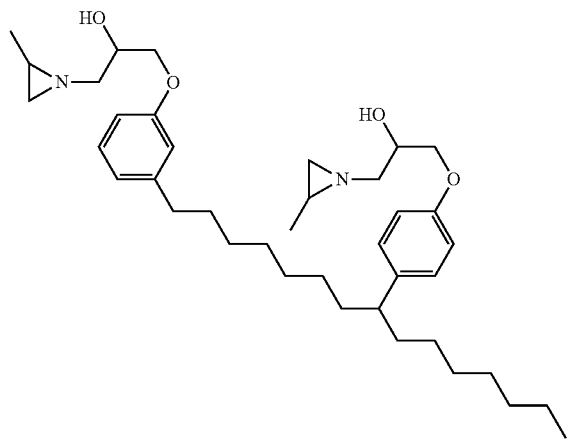 [SMILES: CCCCCCCC(CCCCCCCc1cccc(OCC(O)CN2CC2C)c1)c1ccc(OCC(O)CN2CC2C)cc1]

A19 The particles according to A1a or to any one of A1 to A18 or any combination derived from the disclosure in section 1 and the entire specification, wherein the AZ-component is selected from the group consisting of AZ2-compound and wherein the AZ2-compound is the compound of the following formula,

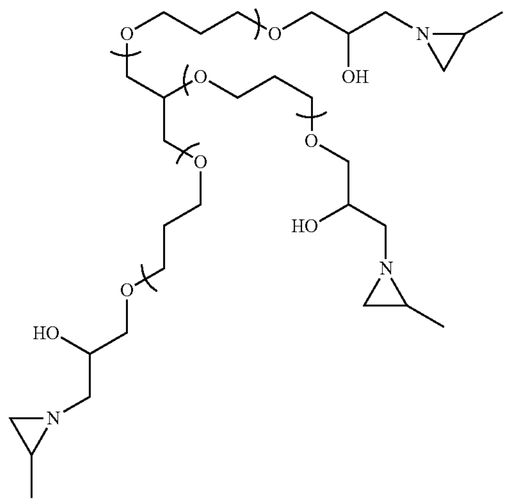

A20 The particles according to A1a or to any one of A1 to A19 or any combination derived from the disclosure in section 1 and the entire specification, wherein the AZ-component is selected from the group consisting of AZ2-compound and wherein the AZ2-compound is the compound of the following formula,

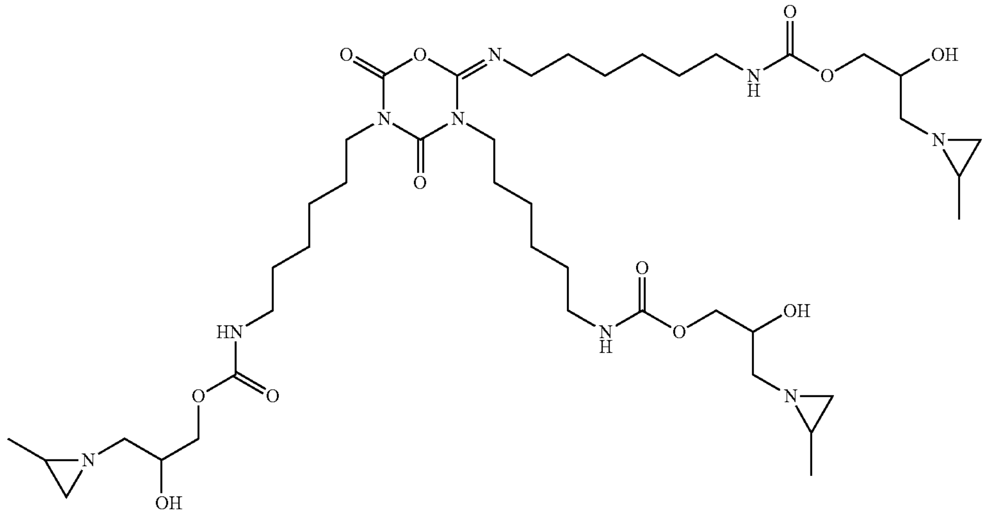 [SMILES: CC1CN1CC(O)COC(=O)NCCCCCC/N=c1/oc(=O)n(CCCCCCNC(=O)OCC(O)CN2CC2C)c(=O)n1CCCCCCNC(=O)OCC(O)CN1CC1C]

A21 The particles according to A1a or to any one of A1 to A20 or any combination derived from the disclosure in section 1 and the entire specification, wherein the AZ-component is selected from the group consisting of AZ2-compound and wherein the AZ2-compound is the compound of the following formula,

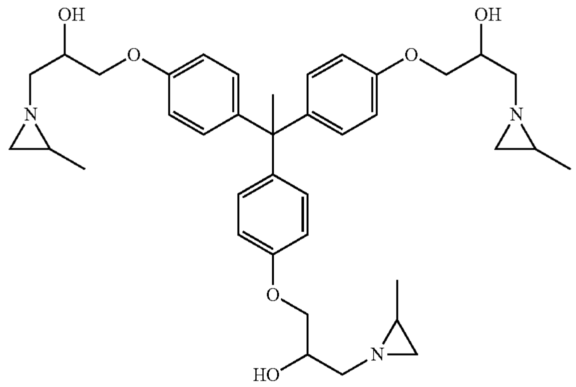 [SMILES: CC1CN1CC(O)COc1ccc(C(C)(c2ccc(OCC(O)CN3CC3C)cc2)c2ccc(OCC(O)CN3CC3C)cc2)cc1]

A22 A mixture according to any combination derived from the disclosure in sections 1 and 3 and the entire specification, comprising:

i) particles of an (aziridinyl hydroxy)-functional organic component according to A1a or to any one of A1 to A21 or any combination derived from the disclosure in sections 1 and 3 and the entire specification, and ii) a polymer which has an acid value determined according to the ASTM D1639-90(1996)e1 of at least 5 and at most 300, preferably at least 8 and at most 200, more preferably at least 10 and at most 150 mg KOH/g and wherein the polymer may optionally comprise ionic functional groups.

A23 The mixture according to 22 or any combination derived from the disclosure in sections 1 and 3 and the entire specification, wherein the polymer is selected from the group consisting of polyesters, polyamides, polycarbonates, polyimides, alkyds, uralkyds, polyacrylics, polyurethanes, poly(urethane-acrylic)s, and mixtures thereof, preferably the polymer is selected from the group consisting of polyamides, polyacrylics, polyurethanes, poly(urethane-acrylic)s, and mixtures thereof, most preferably the polymer is selected from the group consisting of polyacrylics, polyurethanes, poly(urethane-acrylic)s, and mixtures thereof.

A24 The mixture according to any one of A22 to A23 or any combination derived from the disclosure in sections 1 and 3 and the entire specification, wherein the particles are present in an amount of at least 10 and at most 100, preferably at least 15 and at most 95, more preferably at least 20 and at most 90, for example at least 25 and at most 85, for examples at least 30 and at most 80, for example at least 35 and at most 75, for example at least 40 and at most 70, for example at least 40 and at most 65, for example at least 40 and at most 60, and wherein the total amount of all the components that make up the mixture totals 100 wt %.

A25 The mixture according to any one of A22 to A24 or any combination derived from the disclosure in sections 1 and 3 and the entire specification, wherein the polymer is present in an amount of at least 5 and at most 65, preferably at least 10 and at most 60, more preferably at least 20 and at most 55, for example at least 30 and at most 50 wt % on the total weight of the aqueous composition, and wherein the total amount of all the components that make up the mixture totals 100 wt %.

A26 An aqueous dispersion according to any combination derived from the disclosure in sections 3 and 1 and the entire specification, having a pH determined according to the ISO 976:2013 and according to the description, of at least 7.5 and at most 14.0, preferably at least 8.0 and at most 14.0, for example at least 8.5 and at most 13.5, for example at least 9.0 and at most 13.0, for example at least 9.2 and at most 12.5, for example at least 9.4 and at most 12.0, for example at least 9.6 and at most 11.6, for example at least 10.5 and at most 11.5, and wherein the aqueous dispersion comprises:

i) water, and
ii) particles according to A1a or to any one of A1 to A21 or any combination derived from the disclosure in sections 1 and 3 and the entire specification, which particles are dispersed in the water.

A27 The aqueous dispersion according to A26 or any combination derived from the disclosure in sections 3 and 1 and the entire specification, wherein the water is present in an amount of at least 30 and at most 95, preferably at least 45 and at most 85, for example at least 50 and at most 70, for example at least 55 and at most 65 wt % on the total weight of the aqueous dispersion, and wherein the total amount of all the components that make up the aqueous dispersion totals 100 wt %.

A28 The aqueous dispersion according to any one of A26-27 or any combination derived from the disclosure in sections 3 and 1 and the entire specification, further comprising an organic solvent in an amount of at most 40, preferably at most 30, for example at most 25, for example at most 20, for example at most 12, for example at most 10, for example at most 8, for example at most 5, for example at most 4, for example at most 3, for example at most 2, for example at most 1, for example at most 0.5, for example at most 0.2, for example at most 0.1 wt % on the total weight of the aqueous dispersion.

A29 The aqueous dispersion according to any one of A26-A28 or any combination derived from the disclosure in sections 3 and 1 and the entire specification, wherein the aqueous dispersion is free of an organic solvent.

A30 The aqueous dispersion according to any one of A26-A29 or any combination derived from the disclosure in sections 3 and 1 and the entire specification, wherein the particles are present in an amount of at least 5 and at most 70, preferably at least 10 and at most 60, more preferably at least 20 and at most 55, for example at least 25 and at most 55, for example at least 30 and at most 55, for example at least 35 and at most 55, for example at least 35 and at most 50, for example at least 35 and at most 45 wt % on the total weight of the aqueous dispersion, and wherein the total amount of all the components that make up the aqueous dispersion totals 100 wt %.

A31 The aqueous dispersion according to any one of A26-A30 or any combination derived from the disclosure in sections 3 and 1 and the entire specification, wherein the aqueous dispersion comprises a component T selected from the group consisting of: i) organic compounds having a molecular weight determined via MALDI-TOF MS according to the description, lower than 600 Da and comprising at least one aziridine ring, and ii) mixtures thereof, in an amount, determined via LC-MS according to the description, of at most 5, preferably at most 4, more preferably at most 3, for example at most 2, for example at most 1, for example at most 0.5, for example at most 0.1, for example at most 0.05 wt % on the total weight of the AZ-compound.

A32 The aqueous dispersion according to any one of A26-31 or any combination derived from the disclosure in sections 3 and 1 and the entire specification, wherein the aqueous dispersion is free of component T.

A33 The aqueous dispersion according to any one of A26-A32 or any combination derived from the disclosure in sections 3 and 1 and the entire specification, wherein the amount of chloride determined according to the ASTM D1726-11(2019), is at most 0.3, preferably at most 0.2, more preferably at most 0.1, for example at most 0.05, for example at most 0.03 wt % on the total weight of the aqueous dispersion.

A34 The aqueous dispersion according to any one of A26-A33 or any combination derived from the disclosure in sections 3 and 1 and the entire specification, wherein the aqueous dispersion is an aqueous coating dispersion.

A35 Particles obtained by a process comprising the steps of:
i) providing an aqueous dispersion according to any one of A26-A34 or any combination derived from the disclosure in sections 3 and 1 and the entire specification; and
ii) removing the water—and any organic solvent if present—from the aqueous dispersion, preferably by spray-drying or freeze-drying or distillation under vacuum to obtain the particles; and
iii) collecting the particles, and
iv) optionally further drying the particles; and
v) optionally applying means, e.g. grinding, that transform the collected particles into any form that a solid material may exist at standard conditions.

A36 The particles according to A35 or any combination derived from the disclosure in sections 3 and 1 and the entire specification, wherein the particles have a scatter intensity-based average hydrodynamic diameter ($D_H$) determined via dynamic light scattering according to the description, of at least 2 and at most 3000, preferably at least 2 and at most 2500, more preferably at least 2 and at most 2000, even more preferably at least 2 and at most 1500, for example at least 2 and at most 1000, for example at least 2 and at most 900, for example at least 2 and at most 800, for example at least 2 and at most 600, for example at least 2 and at most 500, for example at least 2 and at most 400, for example at least 2 and at most 350, for example at least 2 and at most 300, for example at least 10 and at most 3000, for example at least 10 and at most 2500, for example at least 10 and at most 2000, for example at least 10 and at most 1500, for example at least 10 and at most 1000, for example at least 10 and at most 900, for example at least 10 and at most 800, for example at least 10 and at most 600, for example at least 10 and at most 500, for example at least 10 and at most 400, for example at least 10 and at most 350, for example at least 10 and at most 300, for example at least 20 and at most 3000, for example at least 20 and at most 2500, for example at least 20 and at most 2000, for example at least 20 and at most 1500, for example at least 20 and at most 1000, for example at least 20 and at most 900, for example at least 20 and at most 800, for example at least 20 and at most 600, for example at least 20 and at most 500, for example at least 20 and at most 400, for example at least 20 and at most 350, for example at least 20 and at most 300, for example at least 30 and at most 3000, for example at least 30 and at most 2500, for example at least 30 and at most 2000, for example at least 30 and at most 1500, for example at least 30 and at most 1000, for example at least 30 and at most 900, for example at least 30 and at most 800, for example at least 30 and at most 600, for example at least 30 and at most 500, for example at least 30 and at most 400, for example at least 30 and at most 350, for example at least 30 and at most 300, for example at least 40 and at most 3000, for example at least 40 and at most 2500, for example at least 40 and at most 2000, for example at least 40 and at most 1500, for example at least 40 and at most 1000, for example at least 40 and at most 900, for example at least 40 and at most 800, for example at least 40 and at most 600, for example at least 40 and at most 500, for example at least 40 and at most 400, for example at least 40 and at most 350, for example at least 40 and at most 300, for example at least 50 and at most 3000, for example at least 50 and at most 2500, for example at least 50 and at most 2000, for example at least 50 and at most 1500, for example at least 50 and at most 1000, for example at least 50 and at most 900, for example at least 50 and at most 800, for example at least 50 and at most 600, for example at least 50 and at most 500, for example at least 50 and at most 400, for example at least 50 and at most 350, for example at least 50 and at most 300, for example at least 60 and at most 3000, for example at least 60 and at most 2500, for example at least 60 and at most 2000, for example at least 60 and at most 1500, for example at least 60 and at most 1000, for example at least 60 and at most 900, for example at least 60 and at most 800, for example at least 60 and at most 600, for example at least 60 and at most 500, for example at least 60 and at most 400, for example at least 60 and at most 350, for example at least 60 and at most 300, for example at least 70 and at most 3000, for example at least 70 and at most 2500, for example at least 70 and at most 2000, for example at least 70 and at most 1500, for example at least 70 and at most 1000, for example at least 70 and at most 900, for example at least 70 and at most 800, for example at least 70 and at most 600, for example at least 70 and at most 500, for example at least 70 and at most 400, for example at least 70 and at most 350, for example at least 70 and at most 300, for example at least 80 and at most 3000, for example at least 80 and at most 2500, for example at least 80 and at most 2000, for example at least 80 and at most 1500, for example at least 80 and at most 1000, for example at least 80 and at most 900, for example at least 80 and at most 800, for example at least 80 and at most 600, for example at least 80 and at most 500, for example at least 80 and at most 400, for example at least 80 and at most 350, for example at least 80 and at most 300, for example at least 90 and at most 3000, for example at least 90 and at most 2500, for example at least 90 and at most 2000, for example at least 90 and at most 1500, for example at least 90 and at most 1000, for example at least 90 and at most 900, for example at least 90 and at most 800, for example at least 90 and at most 600, for example at least 90 and at most 500, for example at least 90 and at most 400, for example at least 90 and at most 350, for example at least 90 and at most 300, for example at least 100 and at most 3000, for example at least 100 and at most 2500, for example at least 100 and at most 2000, for example at least 100 and at most 1500, for example at least 100 and at most 1000, for example at least 100 and at most 900, for example at least 100 and at most 800, for example at least 100 and at most 600, for example at least 100 and at most 500, for example at least 100 and at most 400, for example at least 100 and at most 350, for example at least 100 and at most 300 nm.

A37 An aqueous composition according to any combination derived from the disclosure in sections 3 and 1 and the entire specification, comprising:

i) an aqueous dispersion according to any one of A26 to A34 or any combination derived from the disclosure in sections 3 and 1, and ii) a polymer which has an acid value determined according to the ASTM D1639-90(1996)e1 in the range from 5 to 300, preferably from 8 to 200, more preferably from 10 to 150 mg KOH/g and wherein the polymer may optionally comprise ionic functional groups.

A38 The aqueous composition according to A37 or any combination derived from the disclosure in sections 3 and 1 and the entire specification, wherein the aqueous composition has a pH determined according to the ISO 976:2013 and according to the description, of at least 7.5 and at most 14.0, preferably at least 8.0 and at most 14.0, for example at least 8.5 and at most 13.5, for example at least 9.0 and at most 13.0, for example at least 9.2 and at most 12.5, for example at least 9.4 and at most 12.0, for example at least 9.6 and at most 11.6.

A39 The aqueous composition according to any one of A37-A38 or any combination derived from the disclosure in sections 3 and 1 and the entire specification, wherein the polymer is selected from the group consisting of polyesters, polyamides, polycarbonates, polyimides, alkyds, uralkyds, polyacrylics, polyurethanes, poly(urethane-acrylic)s, and mixtures thereof, preferably the polymer is selected from the group consisting of polyamides, polyacrylics, polyurethanes, poly(urethane-acrylic)s, and mixtures thereof, most preferably the polymer is selected from the group consisting of polyacrylics, polyurethanes, poly(urethane-acrylic)s, and mixtures thereof. A40 The aqueous composition according to any one of A37-A39 or any combination derived from the disclosure in sections 3 and 1 and the entire specification, further comprising an organic solvent in an amount of at most 35, preferably at most 30, for example at most 25, for example at most 20, for example at most 15, for example at most 12, for example at most 10, for example at most 8, for example at most 5, for example at most 4, for example at most 3, for example at most 2, for example at most 1, for example at most 0.5, for example at most 0.2, for example at most 0.1 wt % on the total weight of the aqueous composition.

A41 The aqueous composition according to any one of A37-A40 or any combination derived from the disclosure in sections 3 and 1 and the entire specification, wherein the aqueous dispersion is present in the aqueous composition in an amount of at least 0.1 and at most 50, preferably at least 0.2 and at most 45, more preferably at least 0.3 and at most 40, for example at least 0.4 and at most 35, for example at least 0.5 and at most 30, for example at least 0.6 and at most 25, for example at least 0.7 and at most 20, for example at least 0.8 and at most 15, for example at least 0.9 and at most 12, for example at least 1 and at most 10 for example at least 1.2 and at most 8, for example at least 0.3 and at most 25, for example at least 0.8 and at most 15, for example at least 1.5 and at most 12, for example at least 2.5 and at most 10, for example at least 3 and at most 8 wt % on the total weight of the aqueous composition, and wherein the total amount of all the components that make up the aqueous composition totals 100 wt %.

A42 The aqueous composition according to any one of A37-A41 or any combination derived from the disclosure in sections 3 and 1 and the entire specification, wherein the polymer is present in the aqueous composition in an amount of at least 5 and at most 65, preferably at least 10 and at most 60, more preferably at least 20 and at most 55, for example at least 30 and at most 50 wt % on the total weight of the aqueous composition, and wherein the total amount of all the components that make up the aqueous composition totals 100 wt %.

A43 The aqueous composition according to any one of A37-A42 or any combination derived from the disclosure in sections 3 and 1 and the entire specification, wherein the aqueous composition is free of an organic solvent.

A44 The aqueous composition according to any one of A37-A43 or any combination derived from the disclosure in sections 3 and 1 and the entire specification, wherein the aqueous composition is a coating composition preferably an aqueous coating composition.

A45 A kit-of-parts according to any combination derived from the disclosure in sections 4, 3 and 1 and the entire specification, comprising parts A and B which are physically separated from each other, wherein:

i) the part A comprises an aqueous dispersion according to any one of A26-A34 or any combination derived from the disclosure in sections 3 and 1 and the entire specification, and ii) the part B comprises a polymer which has an acid value determined according to the ASTM D1639-90(1996)e1 in the range from 5 to 300, preferably from 8 to 200, more preferably from 10 to 150 mg KOH/g and wherein the polymer may optionally comprise ionic functional groups, and wherein the polymer is preferably selected from the group consisting of polyesters, polyamides, polycarbonates, polyimides, alkyds, uralkyds, polyacrylics, polyurethanes, poly(urethane-acrylic)s, and mixtures thereof, more preferably the polymer is selected from the group consisting of polyamides, polyacrylics, polyurethanes, poly(urethane-acrylic)s, and mixtures thereof, most preferably the polymer is selected from the group consisting of polyacrylics, polyurethanes, poly(urethane-acrylic)s, and mixtures thereof, wherein the part A does not comprise the polymer of the part B, and the part B does not comprise the aqueous dispersion of the part A.

A46 A cured form of particles according to any one of A1a, or A1-A21 or any combination derived from the disclosure in sections 4, 3 and 1 and the entire specification.

A47 A cured form of a mixture according to any one of A22-A25 or any combination derived from the disclosure in sections 4, 3 and 1 and the entire specification.

A48 A cured form of an aqueous dispersion according to any one of A26-A34 or any combination derived from the disclosure in sections 4, 3 and 1 and the entire specification.

A49 A cured form of particles according to any one of A35-A36 or any combination derived from the disclosure in sections 4, 3 and 1 and the entire specification.

A50 A cured form of an aqueous composition according to any one of A37-A45 or any combination derived from the disclosure in sections 4, 3 and 1 and the entire specification.

A51 The cured form according to any one of A46-A50 or any combination derived from the disclosure in sections 4, 3 and 1 and the entire specification, wherein the cured form is a film.

A52 An article comprising: i) particles according to any one of A1a, and A1-A21 or any combination derived from the disclosure in sections 4, 3 and 1 and the entire specification, and/or ii) a mixture according to any one of A22 to A25 any combination derived from the disclosure in sections 4, 3 and 1 and the entire specification, and/or iii) an aqueous dispersion according to any one of A26 to A34 any combination derived from the disclosure in sections 4, 3 and 1 and the entire specification, and/or iv) particles according to any one of A35-A36 any combination derived from the disclosure in sections 4, 3 and 1 and the entire specification, and/or v) an aqueous composition according to any one of A37-A45 any combination derived from the disclosure in sections 4, 3 and 1 and the entire specification, and/or vi) a cured form according to the any one of A46-A51 any combination derived from the disclosure in sections 4, 3 and 1 and the entire specification.

A53 The article according to A52 or any combination derived from the disclosure in sections 4, 3 and 1 and the entire specification, wherein the article is selected from the group consisting of textile, glass, metal, composite, plastic, wood, engineered wood, wood-like, leather, artificial leather, paper, fibers.

A54 Use of any one or any combination of the following:

i) particles according to any one of A1a, and A1-A21 or any combination derived from the disclosure in sections 4, 3 and 1 and the entire specification;

ii) a mixture according to any one of A22-A25 or any combination derived from the disclosure in sections 4, 3 and 1 and the entire specification;

iii) an aqueous dispersion according to any one of A26-A34;

iv) particles according to any one of A35 to A36 or any combination derived from the disclosure in sections 4, 3 and 1 and the entire specification;

v) an aqueous composition according to any one of A37-A44 any combination derived from the disclosure in sections 4, 3 and 1 and the entire specification; as a crosslinker.

A55 Use of any one or any combination of the following:

i) particles according to any one of A1a, and A1-A21 or any combination derived from the disclosure in sections 4, 3 and 1 and the entire specification;

ii) a mixture according to any one of A22-A25 or any combination derived from the disclosure in sections 4, 3 and 1 and the entire specification;

iii) an aqueous dispersion according to any one of A26-A34 or any combination derived from the disclosure in sections 4, 3 and 1 and the entire specification;

iv) particles according to any one of A35-A36 or any combination derived from the disclosure in sections 4, 3 and 1 and the entire specification;

v) an aqueous composition according to any one of A37 to A44 or any combination derived from the disclosure in sections 4, 3 and 1 and the entire specification;

vi) a kit-of-parts according to A45 or any combination derived from the disclosure in sections 4, 3 and 1 and the entire specification;

vii) a cured form according to any of A46 to A51 or any combination derived from the disclosure in sections 4, 3 and 1 and the entire specification;

viii) an article according to any one of A52 to A53 or any combination derived from the disclosure in sections 4, 3 and 1 and the entire specification;

in coatings, paints, inks, varnishes, lubricants, adhesives, additive manufacturing, 3D-printing, textiles, waxes, fuels, photography, plastics, medical compositions, medical devices.

All combinations of minimum and maximum values of the parameters disclosed in the specification may be used to define the parameter ranges for various preferments or embodiments of the invention.

Unless otherwise explicitly stated, any feature, element, component, embodiment, aspect, range and especially any preferred feature, preferred element, preferred embodiment, preferred aspect, preferred range, preferred combination of ranges, preferments, embodiments and aspects in connection with any piece of the disclosure disclosed in any one of A1a or A1 to A55, shown above can be combined with each other and with any other feature, element, component, embodiment, aspect, range and especially any preferred feature, preferred element, preferred embodiment, preferred aspect, preferred range, preferred combination of ranges, preferments, embodiments and aspects of the invention as these are disclosed in the entire specification including the claims.

Unless otherwise explicitly stated, any feature, element, component, embodiment, aspect, range and especially any preferred feature, preferred element, preferred embodiment, preferred aspect, preferred range, preferred combination of ranges, preferments, embodiments and aspects of the invention as these are disclosed in the entire specification including the claims can be combined with each other.

Definitions

By 'aziridine ring' is meant in the specification a 3-membered ring system composed of one nitrogen and two carbon atoms.

By 'organic particles' is meant that the particles do not comprise any inorganic component. In other words, said particles are free of any inorganic component.

By the term 'saturated hydrocarbylene' is meant a bivalent organic group formed by removing two hydrogen atoms from a saturated hydrocarbon, the free valences of which are not engaged in a double bond. Exemplary hydrocarbylenes include but are not limited to methylene.

By the term 'saturated' is meant that the relevant entity does not contain any unsaturation.

By the term 'ionic functional group' is meant herein a functional group that comprises one or both of a cation and an anion and said functional group is covalently bonded to the entity to which it relates to.

By 'poor chemical resistance'—referring to a cured coating (film)—is meant in the specification that the chemical resistance of a film measured as described in the specification is at most 1 [rating scale 0-5, wherein 5 represents the best performance and 0 represents the worst performance, as the rating scale is disclosed in the specification].

By 'reasonable chemical resistance'—referring to a cured coating (film) is meant in the specification that the chemical resistance of a film measured as described in the specification is 2 [rating scale 0-5, wherein 5 represents the best performance and 0 represents the worst performance, as the rating scale is disclosed in the specification].

By 'good chemical resistance'—referring to a cured coating (film)—is meant in the specification that the chemical resistance of a film measured as described in the specification is 3 [rating scale 0-5, wherein 5 represents the best performance and 0 represents the worst performance, as the rating scale is disclosed in the specification].

By 'very good chemical resistance'—referring to a cured coating (film) is meant in the specification that the chemical resistance of a film measured as described in the specification is 4 [rating scale 0-5, wherein 5 represents the best performance and 0 represents the worst performance, as the rating scale is disclosed in the specification].

By 'excellent chemical resistance'—referring to a cured coating (film) is meant in the specification that the chemical resistance of a film measured as described in the specification is 5 [rating scale 0-5, wherein 5 represents the best performance and 0 represents the worst performance, as the rating scale is disclosed in the specification].

By 'starting chemical resistance' referring to an entity—is meant in the specification the chemical resistance—as this is defined and determined in the specification—of the entity determined upon its preparation and just before the entity is stored for 4 weeks at 50° C. (see step 1 of the method entitled 'Assessment of the storage stability and crosslinking efficiency' in view of the method entitled 'Assessment of the chemical resistance' both described in the Examples).

By 'end chemical resistance' referring to an entity—is meant in the specification the chemical resistance—as this is defined and determined in the specification—of the entity after the entity was stored for 4 weeks at 50° C. (see step 2 of the method entitled 'Assessment of the storage stability and crosslinking efficiency' in view of the method entitled 'Assessment of the chemical resistance' both described in the Examples). The end chemical resistance may be equal to or lower than the starting chemical resistance.

By 'poor crosslinking efficiency'—referring to an entity—is meant in the specification that the entity has an end chemical resistance which is poor, or equally that the end chemical resistance of the entity is poor.

By 'reasonable crosslinking efficiency'—referring to an entity—is meant in the specification that the entity has an end chemical resistance which is reasonable, or equally that the end chemical resistance of the entity is reasonable.

By 'good crosslinking efficiency'—referring to an entity—is meant in the specification that the entity has an end chemical resistance which is good, or equally that the end chemical resistance of the entity is good.

By 'very good crosslinking efficiency'—referring to an entity—is meant in the specification that the entity has an end chemical resistance which is very good, or equally that the end chemical resistance of the entity is very good.

By 'excellent crosslinking efficiency'—referring to an entity—is meant in the specification that the entity has an end chemical resistance which is excellent, or equally that the end chemical resistance of the entity is excellent.

By 'starting viscosity' (or equally 'starting apparent viscosity') referring to an entity—is meant in the specification the viscosity—as this is defined and determined in the specification—of the entity determined upon its preparation and just before the entity is stored for 4 weeks at 50° C. (see step 1 of the method entitled 'Assessment of the storage stability and crosslinking efficiency' in view of the method entitled 'Assessment of the viscosity' both described in the Examples).

By 'end viscosity' (or equally 'end apparent viscosity') referring to an entity—is meant in the specification the viscosity—as this is defined and determined in the specification—of the entity after the entity was stored for 4 weeks at 50° C. (see step 2 of the method entitled 'Assessment of the storage stability and crosslinking efficiency' in view of the method entitled 'Assessment of the viscosity' both described in the Examples). The end viscosity may be equal to or higher than the starting viscosity.

By 'workable viscosity'—referring to an entity—is meant in the specification that the end viscosity (as this is defined and determined in the specification) is at most 20 times higher than the starting viscosity (as this is defined and determined in the specification) (or equally the ratio end viscosity/starting viscosity is at most 20), preferably at most 19 times higher than the starting viscosity (or equally the ratio end viscosity/starting viscosity is at most 19), more preferably at most 18 times higher than the starting viscosity (or equally the ratio end viscosity/starting viscosity is at most 18), for example at most 17 times higher than the starting viscosity (or equally the ratio end viscosity/starting viscosity is at most 17), for example at most 16 times higher than the starting viscosity (or equally the ratio end viscosity/starting viscosity is at most 16), for example at most 15 times higher than the starting viscosity (or equally the ratio end viscosity/starting viscosity is at most 15), for example at most 14 times higher than the starting viscosity (or equally the ratio end viscosity/starting viscosity is at most 14), for example at most 13 times higher than the starting viscosity (or equally the ratio end viscosity/starting viscosity is at most 13), for example at most 12 times higher than the starting viscosity (or equally the ratio end viscosity/starting viscosity is at most 12), for example at most 11 times higher than the starting viscosity (or equally the ratio end viscosity/starting viscosity is at most 11), for example at most 10 times higher than the starting viscosity (or equally the ratio end viscosity/starting viscosity is at most 10), for example at most 9 times higher than the starting viscosity (or equally the ratio end viscosity/starting viscosity is at most 9), for example at most 8 times higher than the starting viscosity (or equally the ratio end viscosity/starting viscosity is at most 8), for example at most 7 times higher than the starting viscosity (or equally the ratio end viscosity/starting viscosity is at most 7), for example at most 6 times higher than the starting viscosity (or equally the ratio end viscosity/starting viscosity is at most 6), for example at most 5 times higher than the starting viscosity (or equally the ratio end viscosity/starting viscosity is at most 5), for example at most 4 times higher than the starting viscosity (or equally the ratio end viscosity/starting viscosity is at most 4), for example at most 3 times higher than the starting viscosity (or equally the ratio end viscosity/starting viscosity is at most 3), for example at most 2 times higher than the starting viscosity (or equally the ratio end viscosity/starting viscosity is at most 2). By 'enhanced storage stability' (or equally 'enhanced storage stability for a prolonged time period and at elevated temperature')—referring to an entity—is meant in the specification that the entity has:
i) a workable viscosity (as the latter is defined in the specification), and ii) the end chemical resistance is at most 3 ranking points lower than the starting chemical resistance, preferably at most 2 ranking point lower than the starting chemical resistance, more preferably at most 1 ranking point lower than the starting chemical resistance, most preferably the end chemical resistance is equal to the starting chemical resistance.

By 'prolonged time period and at elevated temperature' is meant a time period of 4 weeks at a temperature of 50° C.

By 'room temperature' is meant herein 23±1° C.

By 'atmospheric pressure' is meant in the specification pressure of 1 atm.

By 'standard conditions' is meant in the specification room temperature and atmospheric pressure, collectively.

By 'lower than' is meant in the specification that the relevant maximum boundary value is not included in the range.

By 'higher than' is meant in the specification that the relevant minimum boundary value is not included in the range.

By 'rpm' is meant revolutions per minute.

By 'polyacrylics' is meant in the specification any polymer comprising of reacted residues of acrylic acid and/or methacrylic acid and/or an ester of acrylic acid and/or an ester of methacrylic acid, and/or styrene, and/or acrylonitrile, and/or acrylamide, and/or esters of itaconic acid, and/or itaconic acid, and/or divinyl benzene, and/or methacrylonitrile, and/or vinyl esters and/or vinyl halides, and/or esters of fumaric acid, and/or fumaric acid; preferably by 'polyacrylics' is meant in the specification any polymer consisting of reacted residues of acrylic acid and/or methacrylic acid and/or an ester of acrylic acid and/or an ester of methacrylic acid, and/or styrene, and/or acrylonitrile, and/or acrylamide, and/or esters of itaconic acid, and/or itaconic acid, and/or divinyl benzene, and/or methacrylonitrile, and/or vinyl esters and/or vinyl halides, and/or esters of fumaric acid, and/or fumaric acid.

By 'epoxide protons' is meant in the specification the two protons of the methylene group ($—CH_2—$) of an oxirane (also known as epoxy) group which group has the following formula

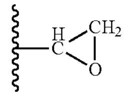

By 'curing' or 'cure' is meant in the specification the process of becoming 'set' that is to form an irreversibly crosslinked network (the so-called 'cured form' or 'cured composition'), a material that can no longer flow, be melted or dissolved. Herein, the terms 'curing' 'cure' and 'crosslinking' are used interchangeably. the curing may take place either at standard conditions (as these are defined in the specification), or by using heat, or by using pressure, or by applying vacuum, or by irradiation e.g. UV-radiation, or by any combination thereof.

The decimal separator in numbers (also known as the radix character) is indicated with a period ('.').

1. The Particles of the Invention

The particles of the invention are as disclosed in the entire specification, including the claims. The terms 'particles of the invention' (or alternatively 'inventive particles') as used in the specification includes any and all of its preferments, combinations of its features and ranges as well as combinations of any and all of its preferments with any and all of the combinations of its features and ranges. Thus, any and all of the inventive particles disclosed in this section 1—and its subsections—includes any and all of their preferments, combinations of their features and ranges as well as combinations of any and all of their preferments with any and all of the combinations of their features and ranges, are collectively referred to—in the entire specification including the claims—as the inventive particles (or equally the particles of the invention). Every and all components of the inventive particles are described in detail in section 1.

The inventive particles are according to any one of A1a or A1 to A21 or any combination disclosed in the entire specification including the claims. More specifically, said particles—preferably are organic particles—comprise an (aziridinyl hydroxy)-functional organic component (AZ-component), and wherein the particles have a scatter intensity-based average hydrodynamic diameter ($D_H$) determined via dynamic light scattering according to the description, of at least 2 and at most 3000, preferably at least 2 and at most 2500, more preferably at least 2 and at most 2000, even more preferably at least 2 and at most 1500, for example at least 2 and at most 1000, for example at least 2 and at most 900, for example at least 2 and at most 800, for example at least 2 and at most 600, for example at least 2 and at most 500, for example at least 2 and at most 400, for example at least 2 and at most 350, for example at least 2 and at most 300, for example at least 10 and at most 3000, for example at least 10 and at most 2500, for example at least 10 and at most 2000, for example at least 10 and at most 1500, for example at least 10 and at most 1000, for example at least 10 and at most 900, for example at least 10 and at most 800, for example at least 10 and at most 600, for example at least 10 and at most 500, for example at least 10 and at most 400, for example at least 10 and at most 350, for example at least 10 and at most 300, for example at least 20 and at most 3000, for example at least 20 and at most 2500, for example at least 20 and at most 2000, for example at least 20 and at most 1500, for example at least 20 and at most 1000, for example at least 20 and at most 900, for example at least 20 and at most 800, for example at least 20 and at most 600, for example at least 20 and at most 500, for example at least 20 and at most 400, for example at least 20 and at most 350, for example at least 20 and at most 300, for example at least 30 and at most 3000, for example at least 30 and at most 2500, for example at least 30 and at most 2000, for example at least 30 and at most 1500, for example at least 30 and at most 1000, for example at least 30 and at most 900, for example at least 30 and at most 800, for example at least 30 and at most 600, for example at least 30 and at most 500, for example at least 30 and at most 400, for example at least 30 and at most 350, for example at least 30 and at most 300, for example at least 40 and at most 3000, for example at least 40 and at most 2500, for example at least 40 and at most 2000, for example at least 40 and at most 1500, for example at least 40 and at most 1000, for example at least 40 and at most 900, for example at least 40 and at most 800, for example at least 40 and at most 600, for example at least 40 and at most 500, for example at least 40 and at most 400, for example at least 40 and at most 350, for example at least 40 and at most 300, for example at least 50 and at most 3000, for example at least 50 and at most 2500, for example at least 50 and at most 2000, for example at least 50 and at most 1500, for example at least 50 and at most 1000, for example at least 50 and at most 900, for example at least 50 and at most 800, for example at least 50 and at most 600, for example at least 50 and at most 500, for example at least 50 and at most 400, for example at least 50 and at most 350, for example at least 50 and at most 300, for example at least 60 and at most 3000, for example at least 60 and at most 2500, for example at least 60 and at most 2000, for example at least 60 and at most 1500, for example at least 60 and at most 1000, for example at least 60 and at most 900, for example at least 60 and at most 800, for example at least 60 and at most 600, for example at least 60 and at most 500, for example at least 60 and at most 400, for example at least 60 and at most 350, for example at least 60 and at most 300, for example at least 70 and at most 3000, for example at least 70 and at most 2500, for example at least 70 and at most 2000, for example at least 70 and at most 1500, for example at least 70 and at most 1000, for example at least 70 and at most 900, for example at least 70 and at most 800, for example at least 70 and at most 600, for example at least 70 and at most 500, for example at least 70 and at most 400, for example at least 70 and at most 350, for example at least 70 and at most 300, for example at least 80 and at most 3000, for example at least 80 and at most 2500, for example at least 80 and at most 2000, for example at least 80 and at most 1500, for example at least 80 and at most 1000, for example at least 80 and at most 900, for example at least 80 and at most 800, for example at least 80 and at most 600, for example at least 80 and at most 500, for example at least 80 and at most 400, for example at least 80 and at most 350, for example at least 80 and at most 300, for example at least 90 and at most 3000, for example at least 90 and at most 2500, for example at least 90 and at most 2000, for example at least 90 and at most 1500, for example at least 90 and at most 1000, for example at least 90 and at most 900, for example at least 90 and at most 800, for example at least 90 and at most 600, for example at least 90 and at most 500, for example at least 90 and at most 400, for example at least 90 and at most 350, for example at least 90 and at most 300, for example at least 100 and at most 3000, for example at least 100 and at most 2500, for example at least 100 and at most 2000, for example at least 100 and at most 1500, for example at least 100 and at most 1000, for example at least 100 and at most 900, for example at least 100 and at most 800, for example at least 100 and at most 600, for example at least 100 and at most 500, for example at least 100 and at most 400, for example at least 100 and at most 350, for example at least 100 and at most 300 nm, and wherein the (aziridinyl hydroxy)-functional organic component (AZ-component) is selected from the group consisting of i) to vi): i) (aziridinyl hydroxy)-functional organic compound AZ1 of Formula A1 having only two aziridine rings (AZ1-compound), ii) (aziridinyl hydroxy)-functional organic compound AZ2 of Formula A2 having only three aziridine rings (AZ2-compound), iii) (aziridinyl hydroxy)-functional organic compound AZ3 of Formula A3 having only four aziridine rings (AZ3-compound), iv) (aziridinyl hydroxy)-functional organic compound AZ4 of Formula A4 having only five aziridine rings (AZ4-compound), v) (aziridinyl hydroxy)-functional organic compound AZ5 of Formula A5 having only six aziridine rings (AZ5-compound), and vi) mixtures thereof, preferably the AZ-component is selected from the group consisting of i) to iv): i) (aziridinyl hydroxy)functional organic compound AZ1 of Formula A1 having only two aziridine rings (AZ1-compound), ii) (aziridinyl hydroxy)-functional organic compound AZ2 of Formula A2 having only three aziridine rings (AZ2-compound), iii) (aziridinyl hydroxy)-functional organic compound AZ3 of Formula A3 having only four aziridine rings (AZ3-compound), and iv) mixtures thereof, Formula A1

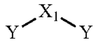

Formula A2

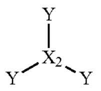

Formula A3

Formula A4

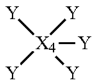

Formula A5

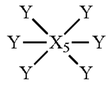

wherein $X_1$ is a bivalent aliphatic organic radical or a bivalent aromatic organic radical, preferably $X_1$ is a bivalent aliphatic organic radical;

$X_2$ is a trivalent aliphatic organic radical or a trivalent aromatic organic radical, preferably $X_2$ is a trivalent aliphatic organic radical;

$X_3$ is a quadrivalent aliphatic organic radical or a quadrivalent aromatic organic radical, preferably $X_3$ is a quadrivalent aliphatic organic radical;

$X_4$ is a pentavalent aliphatic organic radical or a pentavalent aromatic organic radical, preferably $X_4$ is a pentavalent aliphatic organic radical;

$X_5$ is a hexavalent aliphatic organic radical or a hexavalent aromatic organic radical, preferably $X_5$ is a hexavalent aliphatic organic radical;

and wherein each of the $X_1$ to $X_5$ consists of a collection of atoms covalently connected in a configuration that comprises—preferably consists of—linear and/or branched and/or ring structures, which collection of atoms is selected from the group consisting of i) to x): i) carbon and hydrogen atoms, ii) carbon, hydrogen and oxygen atoms, iii) carbon, hydrogen and nitrogen atoms, iv) carbon, hydrogen and sulphur atoms, v) carbon, hydrogen, oxygen and nitrogen atoms, vi) carbon, hydrogen, nitrogen and sulphur atoms, vii) carbon, hydrogen, oxygen and sulphur atoms, viii) carbon, hydrogen, oxygen, nitrogen and sulphur, atoms, ix) carbon, hydrogen and silicon atoms, and x) carbon, hydrogen, oxygen and silicon atoms and xi) any combination of ix) and/or x) with any one or all of the iii) to viii), and wherein each of the $X_1$ to $X_5$ has carbon atoms and hydrogen atoms, and wherein each of the $X_1$ to $X_5$ has optionally oxygen atoms and/or nitrogen atoms and/or sulphur atoms and/or silicon atoms, and wherein the $X_1$, and/or the $X_2$ and/or the $X_3$ and/or the $X_4$ and/or the $X_5$ may optionally comprise an ionic functional group, preferably the $X_1$, and/or the $X_2$ and/or the $X_3$ and/or the $X_4$ and/or the $X_5$ does not comprise an ionic functional group, and wherein Y is a monovalent organic radical selected from the group consisting of: i) monovalent (aziridinyl hydroxyisopropyl) organic radical of Formula B1, ii) monovalent (aziridinyl hydroxycyclohexane) organic radical of Formula B2, and iii) monovalent (aziridinyl hydroxycyclohexane) organic radical of Formula B3, preferably Y is a monovalent (aziridinyl hydroxyisopropyl) organic radical of Formula B1, Formula B1

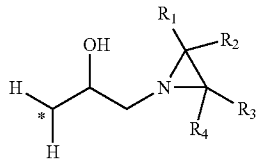

Formula B2

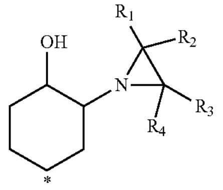

Formula B3

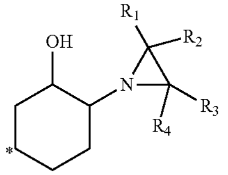

and wherein $R_1$ is selected from the group consisting of hydrogen and methyl; and $R_2$ is selected from the group consisting of hydrogen, methyl, and $C_2$-$C_5$ alkyl; and $R_3$ is selected from the group consisting of methyl, and $C_2$-$C_4$ alkyl; and $R_4$ is selected from the group consisting of hydrogen, methyl, and $C_2$-$C_4$ alkyl;

and wherein the Y in each of the compounds A1 to A5 may be the same or different to each other and wherein each of the single covalent bonds between the Y and each one of the $X_1$ to $X_5$ is selected from the group consisting of carbon-carbon single bond, carbon-oxygen single bond and carbon-nitrogen single bond, preferably carbon-oxygen single bond and carbon-nitrogen single bond, more preferably carbon-oxygen single bond, and wherein each of the AZ1- to AZ5-compound has a molecular weight determined via MALDI-TOF MS according to the description, of at least 600 and at most 10000 Da.

Preferably, the inventive particles comprise at least 20, preferably at least 40, more preferably at least 55, even more preferably at least 70, for example at least 82, for example at least 85, for example at least 89, for example at least 93, for example at least 96, for example at least 99 wt % of the (aziridinyl hydroxy)-functional organic component (AZ-component).

Preferably, each of the AZ1- to AZ5-compound has a molecular weight of at least 600 and at most 8000, preferably at least 600 and at most 7000, more preferably at least 600 and at most 6000, for example at least 600 and at most 5500, for example at least 600 and at most 5000, for example at least 600 and at most 4000, for example at least 600 and at most 3500, for example at least 600 and at most 3200, for example at least 600 and at most 3000, for example at least 600 and at most 2500, for example at least 600 and at most 2200, for example at least 600 and at most 2000, for example at least 630 and at most 10000, preferably at least 630 and at most 8000, more preferably at least 630 and at most 7000, even more preferably at least 630 and at most 6000, for example at least 630 and at most 5500, for example at least 630 and at most 5000, for example at least 630 and at most 4000, for example at least 630 and at most 3500, for example at least 630 and at most 3200, for example at least 630 and at most 3000, for example at least 630 and at most 2500, for example at least 630 and at most 2200, for example at least 630 and at most 2000, for example at least 640 and at most 10000, for example at least 640 and at most 8000, for example at least 640 and at most 7000, for example at least 640 and at most 6000, for example at least 640 and at most 5500, for example at least 640 and at most 5000, for example at least 640 and at most 4000, for example at least 640 and at most 3500, for example at least 640 and at most 3200, for example at least 640 and at most 3000, for example at least 640 and at most 2500, for example at least 640 and at most 2200, for example at least 640 and at most 2000, for example at least 650 and at most 10000, for example at least 650 and at most 8000, for example at least 650 and at most 7000, for example at least 650 and at most 6000, for example at least 650 and at most 5500, for example at least 650 and at most 5000, for example at least 650 and at most 4000, for example at least 650 and at most 3500, for example at least 650 and at most 3200, for example at least 650 and at most 3000, for example at least 650 and at most 2500, for example at least 650 and at most 2200, for example at least 650 and at most 2000, for example at least 700 and at most 10000, for example at least 700 and at most 8000, for example at least 700 and at most 7000, for example at least 700 and at most 6000, for example at least 700 and at most 5500, for example at least 700 and at most 5000, for example at least 700 and at most 4000, for example at least 700 and at most 3500, for example at least 700 and at most 3200, for example at least 700 and at most 3000, for example at least 700 and at most 2500, for example at least 700 and at most 2200, for example at least 700 and at most 2000, for example at least 750 and at most 10000, for example at least 750 and at most 8000, for example at least 750 and at most 7000, for example at least 750 and at most 6000, for example at least 750 and at most 5500, for example at least 750 and at most 5000, for example at least 750 and at most 4000, for example at least 750 and at most 3500, for example at least 750 and at most 3200, for example at least 750 and at most 3000, for example at least 750 and at most 2500, for example at least 750 and at most 2200, for example at least 750 and at most 2000, for example at least 800 and at most 10000, for example at least 800 and at most 8000, for example at least 800 and at most 7000, for example at least 800 and at most 6000, for example at least 800 and at most 5500, for example at least 800 and at most 5000, for example at least 800 and at most 4000, for example at least 800 and at most 3500, for example at least 800 and at most 3200, for example at least 800 and at most 3000, for example at least 800 and at most 2500, for example at least 800 and at most 2200, for example at least 800 and at most 2000, for example at least 850 and at most 10000, for example at least 850 and at most 8000, for example at least 850 and at most 7000, for example at least 850 and at most 6000, for example at least 850 and at most 5500, for example at least 850 and at most 5000, for example at least 850 and at most 4000, for example at least 850 and at most 3500, for example at least 850 and at most 3200, for example at least 850 and at most 3000, for example at least 850 and at most 2500, for example at least 850 and at most 2200, for example at least 850 and at most 2000, for example at least 900 and at most 10000, for example at least 900 and at most 8000, for example at least 900 and at most 7000, for example at least 900 and at most 6000, for example at least 900 and at most 5500, for example at least 900 and at most 5000, for example at least 900 and at most 4000, for example at least 900 and at most 3500, for example at least 900 and at most 3200, for example at least 900 and at most 3000, for example at least 900 and at most 2500, for example at least 900 and at most 2200, for example at least 900 and at most 2000, for example at least 950 and at most 10000, for example at least 950 and at most 8000, for example at least 950 and at most 7000, for example at least 950 and at most 6000, for example at least 950 and at most 5500, for example at least 950 and at most 5000, for example at least 950 and at most 4000, for example at least 950 and at most 3500, for example at least 950 and at most 3200, for example at least 950 and at most 3000, for example at least 950 and at most 2500, for example at least 950 and at most 2200, for example at least 950 and at most 2000, for example at least 1000 and at most 10000, for example at least 1000 and at most 8000, for example at least 1000 and at most 7000, for example at least 1000 and at most 6000, for example at least 1000 and at most 5500, for example at least 1000 and at most 5000, for example at least 1000 and at most 4000, for example at least 1000 and at most 3500, for example at least 1000 and at most 3200, for example at least 1000 and at most 3000, for example at least 1000 and at most 2500, for example at least 1000 and at most 2200, for example at least 1000 and at most 2000, for example at least 1100 and at most 10000, for example at least 1100 and at most 8000, for example at least 1100 and at most 7000, for example at least 1100 and at most 6000, for example at least 1100 and at most 5500, for example at least 1100 and at most 5000, for example at least 1100 and at most 4000, for example at least 1100 and at most 3500, for example at least 1100 and at most 3200, for example at least 1100 and at most 3000, for example at least 1100 and at most 2500, for example at least 1100 and at most 2200, for example at least 1100 and at most 2000, for example at least 1200 and at most 10000, for example at least 1200 and at most 8000, for example at least 1200 and at most 7000, for example at least 1200 and at most 6000, for example at least 1200 and at most 5500, for example at least 1200 and at most 5000, for example at least 1200 and at most 4000, for example at least 1200 and at most 3500, for example at least 1200 and at most 3200, for example at least 1200 and at most 3000, for example at least 1200 and at most 2500, for example at least 1200 and at most 2200, for example at least 1200 and at most 2000 Da.

Preferably, the $X_1$ is a bivalent aliphatic organic radical or a bivalent aromatic organic radical other than a bivalent radical of bisphenol A.

Preferably, the $X_1$ is a bivalent aliphatic organic radical or a bivalent aromatic organic radical other than a bivalent organic radical selected from the group consisting of bivalent radical of bisphenol A, bivalent radical of bisphenol AP, bivalent radical of bisphenol AF, bivalent radical of bisphenol B, bivalent radical of bisphenol BP, bivalent radical of bisphenol C, bivalent radical of bisphenol $C_2$, bivalent radical of bisphenol E, bivalent radical of bisphenol F, bivalent radical of bisphenol G, bivalent radical of bisphenol M, bivalent radical of bisphenol S, bivalent radical of bisphenol P, bivalent radical of bisphenol PH, bivalent radical of bisphenol TMC, bivalent radical of bisphenol Z, bivalent radical of dinitrobisphenol A, bivalent radical of tetrabromobisphenol A, and combinations thereof, preferably $X_1$ is a bivalent aliphatic organic radical.

Preferably, the $X_1$, and/or the $X_2$ and/or the $X_3$ and/or the $X_4$ and/or the $X_5$ comprises at least one structural unit or a combination of structural units selected from the group consisting of unit 1, unit 2, unit 3, unit 4, unit 5, unit 6, unit 7, unit 8, unit 9, unit 10, and unit 11, preferably comprises at least one structural unit or a combination of structural units selected from the group consisting of unit 1, unit 4, unit 9, unit 10 and unit 11, as the units 1 to 11 are depicted below:

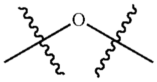

unit 1

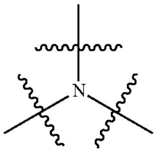

unit 2

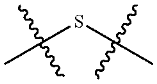

unit 3

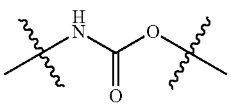

unit 4

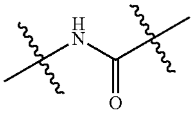

unit 5

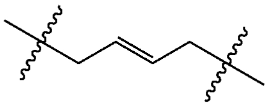

unit 6

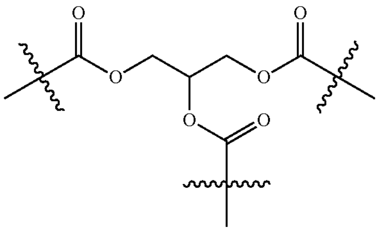

unit 7

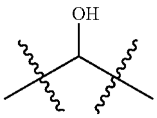

unit 8

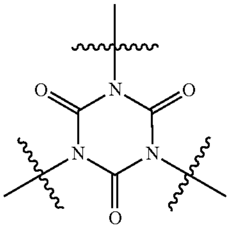

unit 9

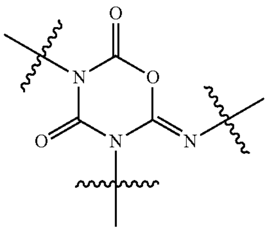

unit 10

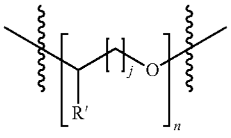

unit 11 wherein

R' is selected from the group consisting of hydrogen and methyl; and j is an integer ranging from 1 to 5, preferably from 1 to 3; and n is an integer ranging from and including 2 up to and including 50, preferably from and including 2 up to and including 40, more preferably from and including 2 up to and including 30, most preferably from and including 2 up to and including 20, for example from and including 2 up to and including 15, for example from and including 2 up to and including 10, for example from and including 2 up to and including 5, for example the n is 2, for example from and including 3 up to and including 50, for example from and including 3 up to and including 40, for example from and including 3 up to and including 30, for example from and including 3 up to and including 20, for example from and including 3 up to and including 15, for example from and including 3 up to and including 10, for example from and including 3 up to and including 5, for example the n is 3, for example from and including 4 up to and including 50, for example from and including 4 up to and including 40, for example from and including 4 up to and including 30, for example from and including 4 up to and including 20, for example from and including 4 up to and including 15, for example from and including 4 up to and including 10, for example from and including 4 up to and including 5, for example the n is 4, for example from and including 5 up to and including 50, for example from and including 5 up to and including 40, for example from and including 5 up to and including 30, for example from and including 5 up to and including 20, for example from and including 5 up to and including 15, for example from and including 5 up to and including 10, for example the n is 5, for example from and including 6 up to and including 50, for example from and including 6 up to and including 40, for example from and including 6 up to and including 30, for example from and including 6 up to and including 20, for example from and including 6 up to and including 15, for example from and including 6 up to and including 10, for example the n is 6, for example from and including 7 up to and including 50, for example from and including 7 up to and including 40, for example from and including 7 up to and including 30, for example from and including 7 up to and including 20, for example from and including 7 up to and including 15, for example from and including 7 up to and including 10, for example the n is 7, for example from and including 8 up to and including 50, for example from and including 8 up to and including 40, for example from and including 8 up to and including 30, for example from and including 8 up to and including 20, for example from and including 8 up to and including 15, for example from and including 8 up to and including 10, for example the n is 8, for example from and including 9 up to and including 50, for example from and including 9 up to and including 40, for example from and including 9 up to and including 30, for example from and including 9 up to and including 20, for example from and including 9 up to and including 15, for example from and including 9 up to and including 10, for example the n is 9, for example from and including 10 up to and including 50, for example from and including 10 up to and including 40, for example from and including 10 up to and including 30, for example from and including 10 up to and including 20, for example from and including 10 up to and including 15, for example the n is 10.

Preferably, the $R_1$ is selected from the group consisting of hydrogen and methyl; and $R_2$ is selected from the group consisting of hydrogen, methyl, and ethyl; and $R_3$ is selected from the group consisting of methyl, and $C_2$-$C_4$ alkyl; and $R_4$ is selected from the group consisting of hydrogen, methyl, and ethyl.

Preferably, the aggregate number of carbon atoms in $R_1$, and $R_2$ and $R_3$ and $R_4$ is at most 9, preferably at most 4, more preferably at most 2, for example at most 1.

Preferably, the $X_1$ and/or the $X_2$ and/or the $X_3$ and/or the $X_4$ and/or the $X_5$ does not contain one or any combination of the following structural units BP1, BP2, BP3, and BS unit BP1

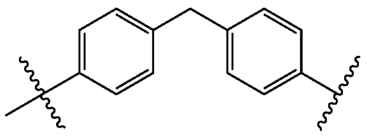

unit BP2

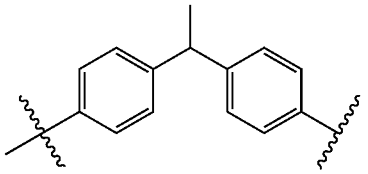

unit BP3

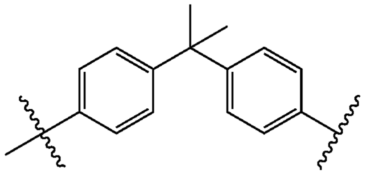

unit BS

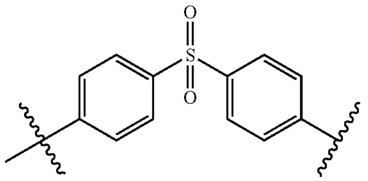

Preferably, the $X_1$, and/or the $X_2$ and/or the $X_3$ and/or the $X_4$ and/or the $X_5$ comprises at least one unit 11 as a structural unit.

Preferably, $X_1$ is the bivalent aliphatic organic radical of Formula A1a'

Formula A1a'

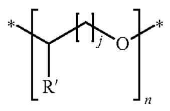

wherein

R' is selected from the group consisting of hydrogen and methyl; and j is an integer ranging from 1 to 5, preferably from 1 to 3; and n is an integer ranging from and including 2 up to and including 50, preferably from and including 2 up to and including 40, more preferably from and including 2 up to and including 30, most preferably from and including 2 up to and including 20, for example from and including 2 up to and including 15, for example from and including 2 up to and including 10, for example from and including 2 up to and including 5, for example the n is 2, for example from and including 3 up to and including 50, for example from and including 3 up to and including 40, for example from and including 3 up to and including 30, for example from and including 3 up to and including 20, for example from and including 3 up to and including 15, for example from and including 3 up to and including 10, for example from and including 3 up to and including 5, for example the n is 3, for example from and including 4 up to and including 50, for example from and including 4 up to and including 40, for example from and including 4 up to and including 30, for example from and including 4 up to and including 20, for example from and including 4 up to and including 15, for example from and including 4 up to and including 10, for example from and including 4 up to and including 5, for example the n is 4, for example from and including 5 up to and including 50, for example from and including 5 up to and including 40, for example from and including 5 up to and including 30, for example from and including 5 up to and including 20, for example from and including 5 up to and including 15, for example from and including 5 up to and including 10, for example the n is 5, for example from and including 6 up to and including 50, for example from and including 6 up to and including 40, for example from and including 6 up to and including 30, for example from and including 6 up to and including 20, for example from and including 6 up to and including 15, for example from and including 6 up to and including 10, for example the n is 6, for example from and including 7 up to and including 50, for example from and including 7 up to and including 40, for example from and including 7 up to and including 30, for example from and including 7 up to and including 20, for example from and including 7 up to and including 15, for example from and including 7 up to and including 10, for example the n is 7, for example from and including 8 up to and including 50, for example from and including 8 up to and including 40, for example from and including 8 up to and including 30, for example from and including 8 up to and including 20, for example from and including 8 up to and including 15, for example from and including 8 up to and including 10, for example the n is 8, for example from and including 9 up to and including 50, for example from and including 9 up to and including 40, for example from and including 9 up to and including 30, for example from and including 9 up to and including 20, for example from and including 9 up to and including 15, for example from and including 9 up to and including 10, for example the n is 9, for example from and including 10 up to and including 50, for example from and including 10 up to and including 40, for example from and including 10 up to and including 30, for example from and including 10 up to and including 20, for example from and including 10 up to and including 15, for example the n is 10.

Preferably, each of the $X_1$ to $X_5$ contains only single covalent bonds, or both single and double covalent bonds, and wherein the single covalent bonds are selected from the group consisting of carbon-carbon single bond, carbon-hydrogen single bond, carbon-nitrogen single bond, carbon-sulphur single bond, carbon-silicon single bond, silicon-oxygen single bond, nitrogen-hydrogen single bond, sulphur-oxygen single bond, carbon-oxygen single bond wherein the oxygen is bonded to a hydrogen forming a hydroxyl group, silicon-oxygen-silicon single bonds, and wherein the double covalent bonds are selected from the group consisting of carbon-carbon double bond, carbon-nitrogen double bond, sulphur-oxygen double bond, carbon-oxygen double bond.

Preferably, each of the $X_1$ to $X_5$ contains only single covalent bonds, or both single and double covalent bonds, and wherein the single covalent bonds are selected from the group consisting of carbon-carbon single bond, carbon-hydrogen single bond, carbon-nitrogen single bond, carbon-sulphur single bond, carbon-silicon single bond, silicon-oxygen single bond, nitrogen-hydrogen single bond, sulphur-oxygen single bond, carbon-oxygen single bond wherein the oxygen is bonded to a hydrogen forming a hydroxyl group, silicon-oxygen-silicon single bonds, and wherein the double covalent bonds are selected from the group consisting of carbon-carbon double bond, carbon-nitrogen double bond, sulphur-oxygen double bond, carbon-oxygen double bond wherein the carbon is a member of a ring structure, and carbon-oxygen double bond wherein the carbon is bonded to another two carbons via carbon-carbon single bonds, carbon-oxygen double bond wherein the carbon is bonded to another oxygen via single bond and to a nitrogen via a single bond, carbon-oxygen double bond wherein the carbon is bonded to two nitrogens via carbon-nitrogen single bonds, carbon-oxygen double bond wherein the carbon is bonded to another two oxygens via single bonds.

Preferably, the aggregate number of carbon and hydrogen atoms in $X_1$ and/or $X_2$ and/or $X_3$ and/or $X_4$ and/or $X_5$ is at least 5, preferably at least 10, more preferably at least 15, most preferably at least 20, for example at least 25, for example at least 30, for example at least 35, for example at least 40, for example at least 45, for example at least 50, for example at least 55, for example at least 60, for example at least 65, for example at least 70, for example at least 75, for example at least 80, for example at least 85, for example at least 90, for example at least 95, for example at least 97, for example at least 98, for example at least 99, for example 100% as to the aggregate number of all the atoms present in $X_1$ and/or $X_2$ and/or $X_3$ and/or $X_4$ and/or $X_5$, respectively.

Preferably, the aggregate number of all the atoms present in $X_1$ and/or $X_2$ and/or $X_3$ and/or $X_4$ and/or $X_5$ is at most 600, preferably at most 550, more preferably at most 500, most preferably at most 450, for examples at most 400, for example at most 350, for example at most 300, for example at most 250, for example at most 200.

Preferably, the AZ-component is selected from the group consisting of i) to v): i) (aziridinyl hydroxy)-functional organic compound AZ1 of Formula A1 (AZ1-compound), ii) (aziridinyl hydroxy)-functional organic compound AZ2 of Formula A2 (AZ2-compound), iii) (aziridinyl hydroxy)-functional organic compound AZ3 of Formula A3 (AZ3-compound), iv) (aziridinyl hydroxy)-functional organic compound AZ5 of Formula A5 (AZ5-compound), and vi) mixtures thereof, and wherein the AZ1-compound is selected from the group consisting of compounds having the Formula A1a, and compounds having the Formula A1 b, as each of these Formulae A1a-A1 d is described below Formula A1a

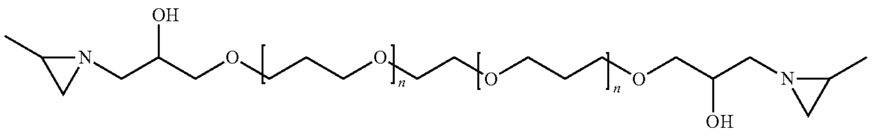

wherein each of the n in Formula A1a is independently selected, and each of the n in Formula A1a is an integer ranging from and including 2 up to and including 20, preferably from and including 2 up to and including 10, more preferably from and including 2 up to and including 7, most preferably from and including 2 up to and including 5, for example from and including 2 up to and including 4, for example from and including 3 up to and including 20, for example from and including 3 up to and including 10, for example from and including 3 up to and including 7, for example from and including 3 up to and including 5, for example from and including 3 up to and including 4, for example n is equal to 4; and Formula A1b

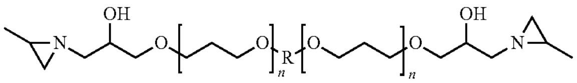

wherein the R in Formula A1 b is a $C_3$-$C_{10}$ saturated hydrocarbylene, and wherein each of the n in Formula Alb is independently selected and each of the n in Formula A1a is an integer ranging from and including 2 up to and including 20, preferably from and including 2 up to and including 10, more preferably from and including 2 up to and including 7, most preferably from and including 2 up to and including 5, for example from and including 2 up to and including 4, for example from and including 3 up to and including 20, for example from and including 3 up to and including 10, for example from and including 3 up to and including 7, for example from and including 3 up to and including 5, for example from and including 3 up to and including 4, for example n is equal to 4; and Formula A1c

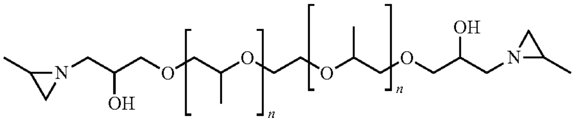

wherein each of the n in Formula A1c is independently selected and each of the n in Formula A1 b is an integer ranging from and including 2 up to and including 20, preferably from and including 2 up to and including 10, more preferably from and including 2 up to and including 7, most preferably from and including 2 up to and including 5, for example from and including 2 up to and including 4, for example from and including 3 up to and including 20, for example from and including 3 up to and including 10, for example from and including 3 up to and including 7, for example from and including 3 up to and including 5, for example from and including 3 up to and including 4, for example n is equal to 4, and Formula A1d

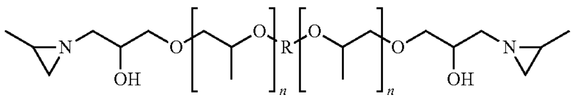

wherein the R in Formula A1 d is a $C_3$-$C_{10}$ saturated hydrocarbylene, and wherein each of the n in Formula A1 d is independently selected and each of the n in Formula Alb is an integer ranging from and including 2 up to and including 20, preferably from and including 2 up to and including 10, more preferably from and including 2 up to and including 7, most preferably from and including 2 up to and including 5, for example from and including 2 up to and including 4, for example from and including 3 up to and including 20, for example from and including 3 up to and including 10, for example from and including 3 up to and including 7, for example from and including 3 up to and including 5, for example from and including 3 up to and including 4, for example n is equal to 4, and wherein the AZ2-compound is selected from the group consisting of compounds having the Formula A2a, compounds having the Formula A2b, compounds having the Formula A2c, compounds having the Formula A2d, compounds having the Formula A2e, as each of these Formulae A2a-A2e is described below Formula A2a

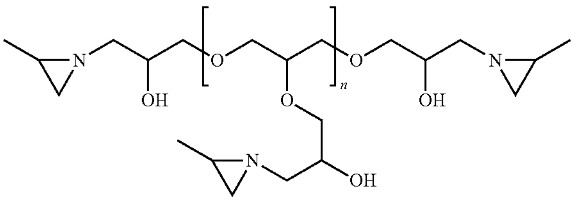

wherein the n in Formula A2a is an integer ranging from and including 2 up to and including 20, for example from and including 2 up to and including 10, for example from and including 2 up to and including 8, for example from and including 3 up to and including 20, for example from and including 3 up to and including 10, for example from and including 3 up to and including 8, for example from and including 4 up to and including 20, for example from and including 4 up to and including 10, for example from and including 4 up to and including 8, for example from and including 5 up to and including 20, for example from and including 5 up to and including 10, for example from and including 5 up to and including 8, for example from and including 6 up to and including 20, for example from and including 6 up to and including 10, for example from and including 6 up to and including 8, for example n is equal to 7;

and

Formula A2b

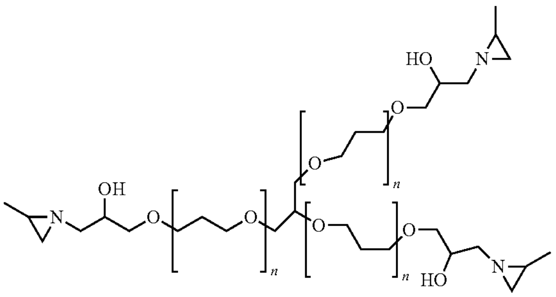

wherein each of the n in Formula A2b is independently selected and each of the n in Formula A2b is an integer ranging from and including 2 up to and including 20, preferably from and including 2 up to and including 15, more preferably from and including 2 up to and including 12, most preferably from and including 2 up to and including 11, for example from and including 3 up to and including 20, for example from and including 3 up to and including 15 for example from and including 3 up to and including 12 for example from and including 3 up to and including 11, for example from and including 4 up to and including 20, for example from and including 4 up to and including 15 for example from and including 4 up to and including 12 for example from and including 4 up to and including 11, for example from and including 5 up to and including 20, for example from and including 5 up to and including 15 for example from and including 5 up to and including 12 for example from and including 5 up to and including 11, for example from and including 6 up to and including 20, for example from and including 6 up to and including 15 for example from and including 6 up to and including 12 for example from and including 6 up to and including 11, for example from and including 7 up to and including 20, for example from and including 7 up to and including 15 for example from and including 7 up to and including 12 for example from and including 7 up to and including 11, for example from and including 8 up to and including 20, for example from and including 8 up to and including 15 for example from and including 8 up to and including 12 for example from and including 8 up to and including 11, for example from and including 9 up to and including 20, for example from and including 9 up to and including 15 for example from and including 9 up to and including 12 for example from and including 9 up to and including 11, for example from and including 10 up to and including 20, for example from and including 10 up to and including 15 for example from and including 10 up to and including 12 for example from and including 10 up to and including 11, for example n is equal to 11;

and

Formula A2c

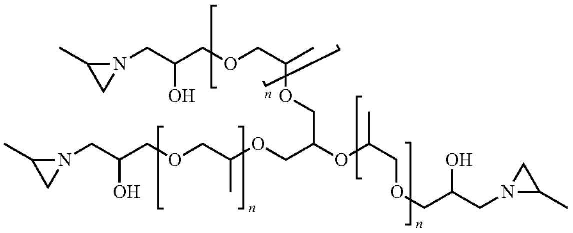

wherein each of the n in Formula A2c is independently selected and each of the n in Formula A2c is an integer ranging from and including 2 up to and including 20, preferably from and including 2 up to and including 15, more preferably from and including 2 up to and including 12, most preferably from and including 2 up to and including 11, for example from and including 3 up to and including 20, for example from and including 3 up to and including 15 for example from and including 3 up to and including 12 for example from and including 3 up to and including 11, for example from and including 4 up to and including 20, for example from and including 4 up to and including 15 for example from and including 4 up to and including 12 for example from and including 4 up to and including 11, for example from and including 5 up to and including 20, for example from and including 5 up to and including 15 for example from and including 5 up to and including 12 for example from and including 5 up to and including 11, for example from and including 6 up to and including 20, for example from and including 6 up to and including 15 for example from and including 6 up to and including 12 for example from and including 6 up to and including 11, for example from and including 7 up to and including 20, for example from and including 7 up to and including 15 for example from and including 7 up to and including 12 for example from and including 7 up to and including 11, for example from and including 8 up to and including 20, for example from and including 8 up to and including 15 for example from and including 8 up to and including 12 for example from and including 8 up to and including 11, for example from and including 9 up to and including 20, for example from and including 9 up to and including 15 for example from and including 9 up to and including 12 for example from and including 9 up to and including 11, for example from and including 10 up to and including 20, for example from and including 10 up to and including 15 for example from and including 10 up to and including 12 for example from and including 10 up to and including 11, for example n is equal to 11;

and

Formula A2d

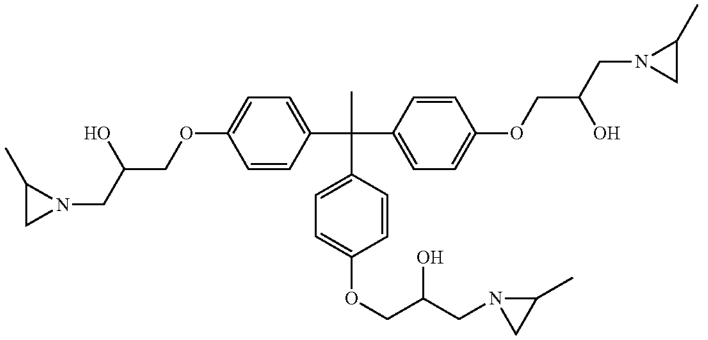

and

-continued

Formula A2e

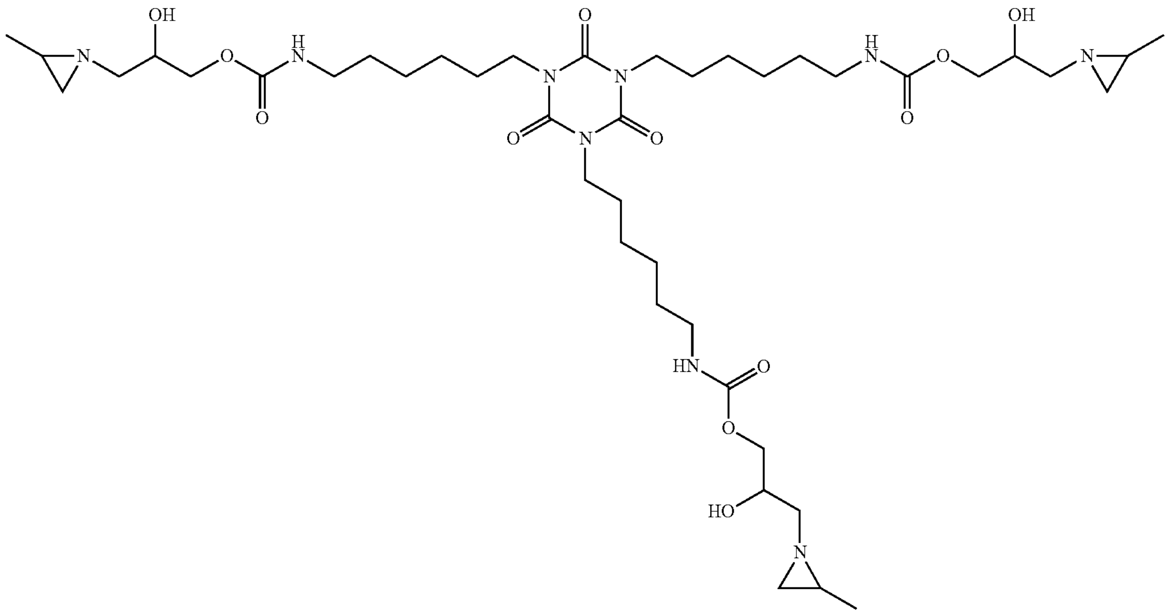

and wherein the AZ3-compound is selected from the group consisting of compounds having the Formula A3a Formula A3a

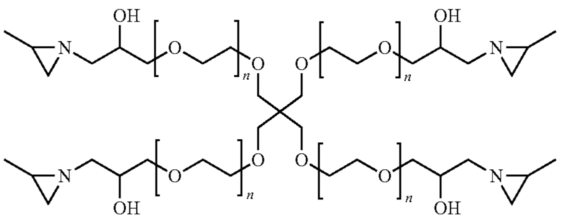

wherein each of the n in Formula A3a is independently selected, and each of the n in Formula A3a is an integer ranging from and including 2 up to and including 20, preferably from and including 2 up to and including 15, more preferably from and including 2 up to and including 10, most preferably from and including 2 up to and including 9, for example from and including 2 up to and including 8, for example from and including 2 up to and including 7, for example from and including 2 up to and including 6, for example from and including 2 up to and including 5, for example from and including 2 up to and including 4, for example from and including 2 up to and including 3, for example n is equal to 3, for example n is equal to 2;

and wherein the AZ5-compound is selected from the group consisting of compounds having the Formula A5a Formula A5a

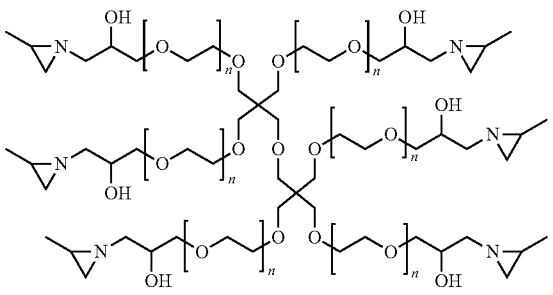

wherein each of the n in Formula A5a is independently selected and each of the n in Formula A5a is an integer ranging from and including 2 up to and including 40, preferably from and including 2 up to and including 30, more preferably from and including 2 up to and including 20, most preferably from and including 2 up to and including 10, for example from and including 2 up to and including 9, for example from and including 2 up to and including 8, for example from and including 2 up to and including 7, for example from and including 2 up to and including 6, for example from and including 2 up to and including 5, for example from and including 2 up to and including 4, for example from and including 3 up to and including 40, for example from and including 3 up to and including 30, for example from and including 3 up to and including 20, for example from and including 3 up to and including 10, for example from and including 3 up to and including 9, for example from and including 3 up to and including 8, for example from and including 3 up to and including 7, for example from and including 3 up to and including 6, for example from and including 3 up to and including 5, for example from and including 3 up to and including 4, for example n is equal to 4, for example n is equal to 3.

Preferably, the $X_1$ and/or the $X_2$ and/or the $X_3$ and/or the $X_4$ and/or the $X_5$ does not contain any structural unit of (or equally derived from) phenol formaldehyde resins (also known as phenolic resins); examples of phenol-formaldehyde (PF) resins include novolacs (acid-catalyzed PF resins with a formaldehyde to phenol ratio of equal to or lower than one), and resols (base-catalyzed PF resins with a formaldehyde to phenol ratio of greater than one, usually equal to 1.5).

Preferably, the AZ-component is selected from the group consisting of AZ1-compound and wherein the AZ1-compound is the compound of the following formula,

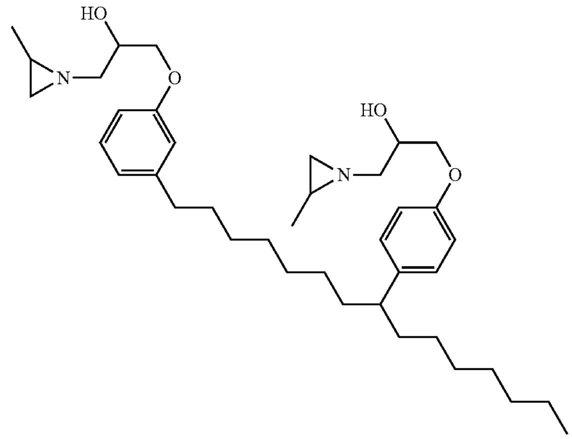 [SMILES: CCCCCCCC(CCCCCCCc1cccc(OCC(O)CN2CC2C)c1)c1ccc(OCC(O)CN2CC2C)cc1]

Preferably, the AZ-component is selected from the group consisting of AZ2-compound and wherein the AZ2-compound is the compound of the following formula,

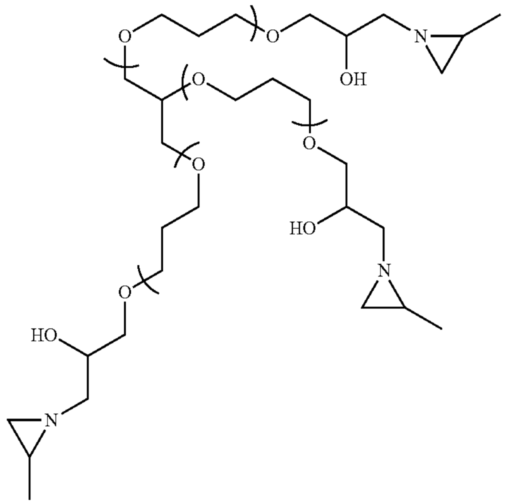

Preferably, the AZ-component is selected from the group consisting of AZ2-compound and wherein the AZ2-compound is the compound of the following formula,

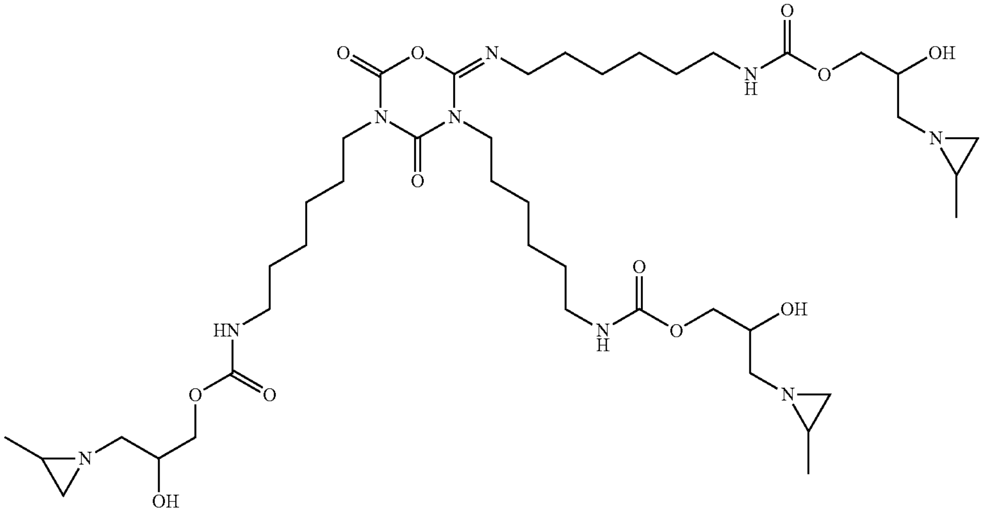 [SMILES: CC1CN1CC(O)COC(=O)NCCCCCC/N=c1/oc(=O)n(CCCCCCNC(=O)OCC(O)CN2CC2C)c(=O)n1CCCCCCNC(=O)OCC(O)CN1CC1C]

Preferably, the AZ-component is selected from the group consisting of AZ2-compound and wherein the AZ2-compound is the compound of the following formula,

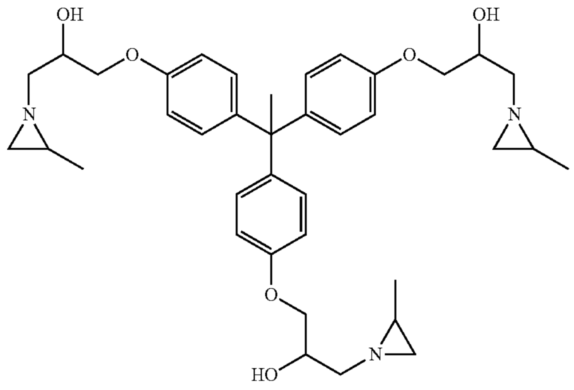 [SMILES: CC1CN1CC(O)COc1ccc(C(C)(c2ccc(OCC(O)CN3CC3C)cc2)c2ccc(OCC(O)CN3CC3C)cc2)cc1]

Preferably, the AZ1-compound and/or the AZ2-compound and/or the

AZ3-compound and/or the AZ4-compound and/or the AZ5-compound comprises polyoxyethylene (—O—$CH_2$—$CH_2$—)x group(s), and/or polyoxypropylene (—O—$CHCH_3$—$CH_2$—$)_x$ group(s) and/or polytetrahydrofurane (—O—$CH_2$—$CH_2$—$CH_2$—$CH_2)_x$ groups, preferably in an amount of at least 10 and at most 92, more preferably at least 15 and at most 85, even more preferably at least 25 and at most 75, for example at least 30 and at most 65, for example at least 35 and at most 55 mol % relative to the corresponding AZ1-compound and/or the AZ2-compound and/or the AZ3-compound and/or the AZ4-compound and/or the AZ5-compound to which these mol % refer to.

Preferably, the AZ1-compound and/or the AZ2-compound and/or the AZ3-compound and/or the AZ4-compound and/or the AZ5-compound comprises methoxy poly(ethylene glycol) (MPEG) and/or poly(ethylene glycol) (PEG) groups (each of these groups with a calculated number average molecular weight ($M_n$) higher than 1600, preferably 2200 Da), preferably in an amount of at least 1 and at most 35, more preferably at least 3 and at most 30, even more preferably at least 5 and at most 27, for example at least 7 and at most 20, for example at least 8 and at most 17, for example at least 9 and at most 15, for example at least 10 and at most 13 mol % relative to the corresponding AZ1-compound and/or the AZ2-compound and/or the AZ3-compound and/or the AZ4-compound and/or the AZ5-compound to which these mol % refer to.

The inventive particles may optionally (further) comprise other components, such as pigments and/or waxes, and/or the usual (processing) additives, for example degassing agents—if the particles are used in powder coatings-, smoothness, appearance enhancing agents or (light) stabilizers. Suitable stabilizers include for example primary and/or secondary antioxidants and UV stabilizers, for example quinones, (sterically hindered) phenolic compounds, phosphonites, phosphites, thioethers and HALS (hindered amine light stabilizers). Examples of suitable degassing agents include cyclohexane dimethanol bisbenzoate, benzoin and benzoin derivatives such as for example those described in WO 02/50194.

In yet another aspect, the invention provides for a cured form (crosslinked inventive particles) obtained by curing the inventive particles as disclosed in the specification. The curing of the inventive particles may take place either by chemical reaction (resulting in the formation of irreversible covalent chemical bonds) or a combination of physical drying and chemical reaction. The curing of the inventive particles may take place either at standard conditions (as these are defined in the specification), or by using heat, or by using pressure, or by applying vacuum, or by irradiation, e.g. UV-radiation, or by any combination thereof. Preferably the particles are cured at a temperature of at least 0 and at most 85, preferably at least 15 and at most 80, more preferably at least 23 and at most 70, most preferably at least 30 and at most 85, for example at least 15 and at most 30° C., for time periods that may vary and are preferably of at most 60, more preferably at most 30, even more preferably at most 15 minutes.

The particles of the invention may be cured in the presence of a cationic initiator.

Alternatively, the particles of the invention may be cured in the presence of a polymer such as for example a polymer which has an acid value determined according to the ASTM D1639-90(1996)e1 in the range from 5 to 300, preferably from 8 to 200, more preferably from 10 to 150 mg KOH/g and wherein the polymer may optionally comprise ionic functional groups, at standard conditions for example 12-48 h (preferably 24-48 h), and/or by heat-curing at elevated temperatures and at atmospheric pressure for example 70-80° C. for 10-60 minutes (preferably 15-30 minutes, more preferably 20 minutes), and/or any combination of curing at room temperature and curing at elevated temperatures; annealing steps (e.g. 50° C. for 16 h) may also be included especially in between curing at elevated temperatures and at atmospheric pressure and curing at standard conditions, wherein the annealing step follows the curing at elevated temperatures and at atmospheric pressure. Such inventive mixtures may preferably be cured at a temperature of at least 0 and at most 85, preferably at least 15 and at most 80, more preferably at least 23 and at most 70, most preferably at least 30 and at most 85, for example at least 15 and at most 30° C., for time periods that may vary and are preferably of at most 60, more preferably at most 30, even more preferably at most 15 minutes.

Obviously, curing at elevated temperatures and at atmospheric pressure requires shorter curing time; curing may also be effected by using pressure or by applying vacuum, or by irradiation, e.g. UV-radiation, or by any combination thereof. Such polymers may be selected from the group consisting of polyesters, polyamides, polycarbonates, polyimides, alkyds, uralkyds, polyacrylics, polyurethanes, poly(urethane-acrylic)s, and mixtures thereof, preferably the polymer is selected from the group consisting of polyamides, polyacrylics, polyurethanes, poly(urethane-acrylic)s, and mixtures thereof, most preferably the polymer is selected from the group consisting of polyacrylics, polyurethanes, poly(urethane-acrylic)s, and mixtures thereof.

2. Processes for Making the Inventive Particles

In order to prepare the particles of the invention, one has to first prepare the AZ-component.

In principle, the (aziridinyl hydroxy)-functional organic component (AZ-component) as this is described in the specification, is preferably obtained by reacting an aziridine of Formula AZIR (abbreviated as 'aziridine-AZIR') with at least a polyepoxide having at least two and at most six epoxy groups.

Formula AZIR

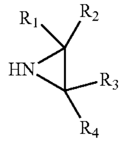

wherein $R_1$ is selected from the group consisting of hydrogen and methyl; and $R_2$ is selected from the group consisting of hydrogen, methyl, and $C_2$-$C_5$ alkyl; and $R_3$ is selected from the group consisting of methyl, and $C_2$-$C_4$ alkyl; and $R_4$ is selected from the group consisting of hydrogen, methyl, and $C_2$-$C_4$ alkyl.

Exemplary aziridines of Formula AZIR include but are not limited to propylene imine, 1,2-dimethyl aziridine, 2,2-dimethyl aziridine, 2-ethyl aziridine, butyl aziridine.

More particularly, the AZ1-compound (as this is described in the specification) is preferably obtained by reacting an aziridine of Formula AZIR with at least a polyepoxide having two epoxy groups. Exemplary polyepoxides having two epoxy groups include but are not limited to any glycidyl ether of a dihydroxy compound with a molecular weight of at least 374 Da, for instance, a polypropylene glycol diglycidyl ether like the ERISYS® GE-24 available by CVC Thermoset Specialties.

More particularly, the AZ2-compound (as this is described in the specification) is preferably obtained by reacting an aziridine of Formula AZIR with at least a polyepoxide having at three epoxy groups. Exemplary polyepoxides having three epoxy groups include but are not limited to any glycidyl ether of a trifunctional hydroxy compound with a molecular weight of at least 261 Da and the ERISYS® GE-36, and EPALLOY® 9000 both available by CVC Thermoset Specialties.

More particularly, the AZ3-compound (as this is described in the specification) is preferably obtained by reacting an aziridine of Formula AZIR with at least a polyepoxide having at four epoxy groups. Exemplary polyepoxides having four epoxy groups include but are not limited to any glycidyl ether of a tetra hydroxy compound with a molecular weight of at least 148 Da, like for instance the glycidyl ether of ethoxylated penta like Polyol R4410, available from Perstop.

More particularly, the AZ4-compound (as this is described in the specification) is preferably obtained by reacting an aziridine of Formula AZIR with at least a polyepoxide having at five epoxy groups. Exemplary polyepoxides having five epoxy groups include but are not limited to any glycidyl ether of a penta hydroxy compound.

More particularly, the AZ5-compound (as this is described in the specification) is preferably obtained by reacting an aziridine of Formula AZIR with at least a polyepoxide having at six epoxy groups. Exemplary polyepoxides having six epoxy groups include but are not limited to any glycidyl ether of an hexa hydroxy compound, for instance, the hexaglycidyl ether of dipentaerythritol.

The reaction (the terms refers to and encompasses any and all of the reactions mentioned just above in this section) takes places at any temperature from 20 to 110° C., more preferably from 50 to 95° C., and most preferably from 70 to 90° C. and its progress can be monitored via $^1$H-NMR spectroscopy. The reaction is carried out for as long as the epoxy groups are reacted; this is monitored and verified by $^1$H-NMR spectroscopy where the characteristic $^1$H-NMR chemical shift of the epoxy protons (2.5-3 ppm) is disappeared. Preferably the reaction is carried out without solvent. However, if desired (for instance to reduce the viscosity), one or more solvents, e.g. methanol, ethanol, toluene, can be used during or after the reaction. If a solvent is used, it is often convenient to first dissolve the polyepoxide in the solvent (or mixture of solvents) before adding the aziridine-AZIR to the reaction mixture. The molar ratio of the mol of the aziridine groups of the aziridine-AZIR to the mol of the epoxy groups of the polyepoxide is at least 1 and at most 8, more preferably at least 1 and at most 4, even more preferably at least 1.1 and at most 3 and most preferably at least 1.2 and at most 2.2. Once the reaction is completed, the residual aziridine-AZIR is distilled off, preferably at a temperature from 60 to 90° C., more preferably from 65 to 80° C., and at reduced pressure, for example from 20 to 50 mbar, preferably from 30-45 mbar. Preferably once the reaction is completed, the residual aziridine-AZIR is distilled off at reduced pressure from 20 to 50 mbar at 70° C., more preferably from 30 to 45 mbar at 70° C. Subsequently, a further distillation step for the removal of any unreacted aziridine-AZIR and any other volatiles is carried out at 25 to 40° C. at 2 to 4 mbar, until no aziridine-AZIR could be detected by $^1$H-NMR spectroscopy. It is often useful to add an additional solvent to the reaction mixture prior to or during distillation, to facilitate the removal of the excess of the aziridine-AZIR. If desired, a base can be used during the reaction, to reduce possible sources of acid. Bases include both organic bases, like tertiary amines or inorganic bases like sodium or potassium carbonate or for instance calcium hydroxide. The inorganic bases can be filtered off after the reaction is completed.

For example, an AZ2-compound of Formula A2d

Formula A2d

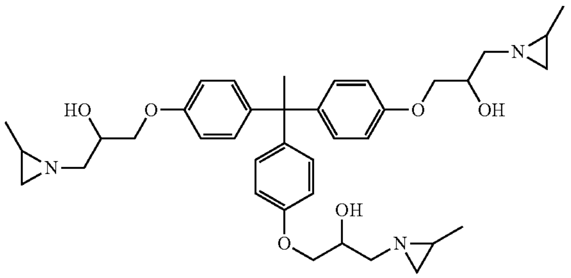

may be prepared by reacting EPALLOY® 9000 (6.26 mmol) (available by CVC Thermoset Specialties) with propylene imine (70.22 mmol) at 80° C. for 3 h in the presence of potassium carbonate (250 mg).

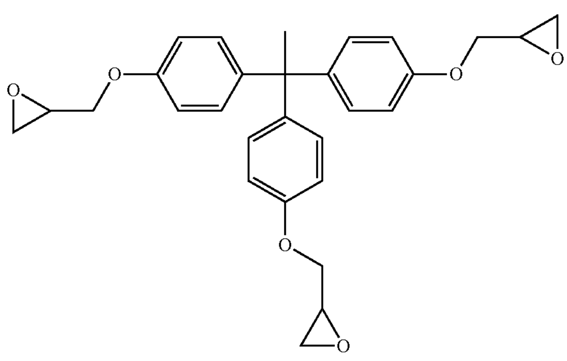

EPALLOY®9000

A high excess of propylene imine is typically used to dissolve EPALLOY® 9000 (the molar ratio of the mol of aziridine-AZIR to the mol of the epoxy groups. The reaction may be monitored via $^1$H-NMR. After 3 h at 80° C., the chemical shifts of the epoxide protons were not visible in the $^1$H-NMR; only some small peaks due to impurities. There has been no change in the $^1$H-NMR spectrum once the reaction mixture was left at 80° C. from 3 to 22 h. The reaction mixture was cooled down to room temperature; it was diluted with toluene. The potassium carbonate was filtered off, and the excess of propylene imine was distilled off with toluene at 70° C. and 40 mbar. The residue was held at 90-95° C. and at a reduced pressure of 3-4 mbar (oil pump) for 2 h, to remove any residual propylene imine and the toluene. The reaction product solidified quickly after cooling. The $^1$H-NMR did not show any peaks attributed to any residual propylene imine.

In principle, a process for making an AZ-compound wherein the Y is a monovalent (aziridinyl hydroxycyclohexane) organic radical of Formula B2, or a monovalent (aziridinyl hydroxycyclohexane) organic radical of Formula B3, is preferably obtained by reacting a hydroxy cyclohexene oxide with an isocyanurate of a diisocyanate, followed by a reaction with an aziridine-AZIR, e.g. propylene imine. For example, an AZ-component wherein the Y is a monovalent (aziridinyl hydroxycyclohexane) organic radical of Formula B2, monovalent (aziridinyl hydroxycyclohexane) organic radical of Formula B3, may be prepared by 1-hydroxy cyclohexene oxide (see Formula below)

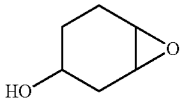

1-hydroxy cyclohexene oxide which is obtained by reacting peracetic acid epoxidation of 1-hydroxy cyclohexene. The 1-hydroxy cyclohexene oxide is reacted with the isocyanurate of hexamethylene diisocyanate and subsequently reacted with a 3-fold excess of propylene imine, at 80° C. for 24 h. Afterwards, the excess of propylene imine is distilled off at a temperature of 50° C. and at reduced pressure. The resulting AZ-compound has a molecular weight of 1018 Da.

Alternatively, a polyoxyalkylene which comprises either at least one amino-functional group (preferably a secondary amino-functional group) or at least one carboxylic acid functional group, is reacted with some epoxy groups of a polyepoxide, prior to the reaction of the polyepoxide with the aziridine-AZIR, as this was described above. This may be a reaction scheme that may introduce polyether groups in any one of the $X_1$ to $X_5$.

Alternatively, an aziridine-AZIR may be partly reacted with a polyoxyalkylene which comprises at least one carboxylic acid functional group, before the reaction of the aziridine-AZIR with the polyepoxide, as this was described above. This may be a reaction scheme that may introduce polyether groups in any one of the $X_1$ to $X_5$.

Preferably, a mono-hydroxy or mono-amine functional polyether can be reacted in a 1:1 molar ratio with 2,4-toluene diisocyanate, and the reaction of which can be subsequently reacted with some of the hydroxyl groups which are formed after the reaction of the imine with the epoxy compound.

Particles may be obtained by a process comprising the steps of:

i) providing an aqueous dispersion of the invention; and
ii) removing the water—and any organic solvent if present—from the aqueous dispersion, preferably by spray-drying or freeze-drying or distillation under vacuum in order to obtain the particles; and
iii) collecting the particles, and
iv) optionally further drying the particles; and
v) optionally applying means, e.g. grinding, that transform the collected particles into any form that a solid material may exist at standard conditions.

(in the context of this specification this process is mentioned for brevity as 'Process A').

The particles obtained by the Process A may have a scatter intensity-based average hydrodynamic diameter ($D_H$) determined via dynamic light scattering according to the description, of at least 2 and at most 3000, preferably at least 2 and at most 2500, more preferably at least 2 and at most 2000, even more preferably at least 2 and at most 1500, for example at least 2 and at most 1000, for example at least 2 and at most 900, for example at least 2 and at most 800, for example at least 2 and at most 600, for example at least 2 and at most 500, for example at least 2 and at most 400, for example at least 2 and at most 350, for example at least 2 and at most 300, for example at least 10 and at most 3000, for example at least 10 and at most 2500, for example at least 10 and at most 2000, for example at least 10 and at most 1500, for example at least 10 and at most 1000, for example at least 10 and at most 900, for example at least 10 and at most 800, for example at least 10 and at most 600, for example at least 10 and at most 500, for example at least 10 and at most 400, for example at least 10 and at most 350, for example at least 10 and at most 300, for example at least 20 and at most 3000, for example at least 20 and at most 2500, for example at least 20 and at most 2000, for example at least 20 and at most 1500, for example at least 20 and at most 1000, for example at least 20 and at most 900, for example at least 20 and at most 800, for example at least 20 and at most 600, for example at least 20 and at most 500, for example at least 20 and at most 400, for example at least 20 and at most 350, for example at least 20 and at most 300, for example at least 30 and at most 3000, for example at least 30 and at most 2500, for example at least 30 and at most 2000, for example at least 30 and at most 1500, for example at least 30 and at most 1000, for example at least 30 and at most 900, for example at least 30 and at most 800, for example at least 30 and at most 600, for example at least 30 and at most 500, for example at least 30 and at most 400, for example at least 30 and at most 350, for example at least 30 and at most 300, for example at least 40 and at most 3000, for example at least 40 and at most 2500, for example at least 40 and at most 2000, for example at least 40 and at most 1500, for example at least 40 and at most 1000, for example at least 40 and at most 900, for example at least 40 and at most 800, for example at least 40 and at most 600, for example at least 40 and at most 500, for example at least 40 and at most 400, for example at least 40 and at most 350, for example at least 40 and at most 300, for example at least 50 and at most 3000, for example at least 50 and at most 2500, for example at least 50 and at most 2000, for example at least 50 and at most 1500, for example at least 50 and at most 1000, for example at least 50 and at most 900, for example at least 50 and at most 800, for example at least 50 and at most 600, for example at least 50 and at most 500, for example at least 50 and at most 400, for example at least 50 and at most 350, for example at least 50 and at most 300, for example at least 60 and at most 3000, for example at least 60 and at most 2500, for example at least 60 and at most 2000, for example at least 60 and at most 1500, for example at least 60 and at most 1000, for example at least 60 and at most 900, for example at least 60 and at most 800, for example at least 60 and at most 600, for example at least 60 and at most 500, for example at least 60 and at most 400, for example at least 60 and at most 350, for example at least 60 and at most 300, for example at least 70 and at most 3000, for example at least 70 and at most 2500, for example at least 70 and at most 2000, for example at least 70 and at most 1500, for example at least 70 and at most 1000, for example at least 70 and at most 900, for example at least 70 and at most 800, for example at least 70 and at most 600, for example at least 70 and at most 500, for example at least 70 and at most 400, for example at least 70 and at most 350, for example at least 70 and at most 300, for example at least 80 and at most 3000, for example at least 80 and at most 2500, for example at least 80 and at most 2000, for example at least 80 and at most 1500, for example at least 80 and at most 1000, for example at least 80 and at most 900, for example at least 80 and at most 800, for example at least 80 and at most 600, for example at least 80 and at most 500, for example at least 80 and at most 400, for example at least 80 and at most 350, for example at least 80 and at most 300, for example at least 90 and at most 3000, for example at least 90 and at most 2500, for example at least 90 and at most 2000, for example at least 90 and at most 1500, for example at least 90 and at most 1000, for example at least 90 and at most 900, for example at least 90 and at most 800, for example at least 90 and at most 600, for example at least 90 and at most 500, for example at least 90 and at most 400, for example at least 90 and at most 350, for example at least 90 and at most 300, for example at least 100 and at most 3000, for example at least 100 and at most 2500, for example at least 100 and at most 2000, for example at least 100 and at most 1500, for example at least 100 and at most 1000, for example at least 100 and at most 900, for example at least 100 and at most 800, for example at least 100 and at most 600, for example at least 100 and at most 500, for example at least 100 and at most 400, for example at least 100 and at most 350, for example at least 100 and at most 300 nm.

The scatter intensity-based average hydrodynamic diameter ($D_H$) of the particles may be controlled via a number of ways. For example, the $D_H$ of the particles may be controlled during the preparation of an aqueous dispersion of the invention (see section 3, 'inventive aqueous dispersions') by using different types of dispersants, and/or different amounts of dispersant(s), and/or by applying different shear stress, and/or by applying different temperature. For example, the $D_H$ of the particles is inversely dependent to the amount of the dispersant used in the preparation of an aqueous dispersion of the invention; for example, the $D_H$ of the particles decreases by increasing the amount of a dispersant. For example, the $D_H$ of the particles is inversely dependent to the shear stress applied during the preparation of an aqueous dispersion of the invention; for example, the $D_H$ of the particles decreases by increasing the shear stress. Exemplary dispersants include but are not limited to ATLAS™ G-5000, ATLAS™ G5002L-LQ supplied by Croda.

The particles of the invention may be prepared by the Process A.

The particles of the invention may be cured in the presence of a cationic initiator.

Alternatively, the particles of the invention may be cured in the presence of a polymer such as for example a polymer which has an acid value determined according to the ASTM D1639-90(1996)e1 in the range from 5 to 300, preferably from 8 to 200, more preferably from 10 to 150 mg KOH/g and wherein the polymer may optionally comprise ionic functional groups, at standard conditions for example 12-48 h (preferably 24-48 h), and/or by heat-curing at elevated temperatures and at atmospheric pressure for example 70-80° C. for 10-60 minutes (preferably 15-30 minutes, more preferably 20 minutes), and/or any combination of curing at room temperature and curing at elevated temperatures; annealing steps (e.g. 50° C. for 16 h) may also be included especially in between curing at elevated temperatures and at atmospheric pressure and curing at standard conditions, wherein the annealing step follows the curing at elevated temperatures and at atmospheric pressure. Such inventive mixtures may preferably be cured at a temperature of at least 0 and at most 85, preferably at least 15 and at most 80, more preferably at least 23 and at most 70, most preferably at least 30 and at most 85, for example at least 15 and at most 30° C., for time periods that may vary and are preferably of at most 60, more preferably at most 30, even more preferably at most 15 minutes.

Obviously, curing at elevated temperatures and at atmospheric pressure requires shorter curing time; curing may also be effected by using pressure or by applying vacuum, or by irradiation, e.g. UV-radiation, or by any combination thereof. Such polymers may be selected from the group consisting of polyesters, polyamides, polycarbonates, polyimides, alkyds, uralkyds, polyacrylics, polyurethanes, poly(urethane-acrylic)s, and mixtures thereof, preferably the polymer is selected from the group consisting of polyamides, polyacrylics, polyurethanes, poly(urethane-acrylic)s, and mixtures thereof, most preferably the polymer is selected from the group consisting of polyacrylics, polyurethanes, poly(urethane-acrylic)s, and mixtures thereof.

3. The Mixtures, the Aqueous Dispersions and the Aqueous Compositions of the Invention The mixtures, the aqueous dispersions and the aqueous compositions of the invention are as disclosed in the entire specification including the claims. The term 'mixtures of the invention' (or alternatively 'inventive mixtures') as used in the specification includes any and all of its preferments, combinations of its features and ranges as well as combinations of any and all of its preferments with any and all of the combinations of its features and ranges. The term 'aqueous dispersions of the invention' (or alternatively 'inventive aqueous dispersions') as used in the specification includes any and all of its preferments, combinations of its features and ranges as well as combinations of any and all of its preferments with any and all of the combinations of its features and ranges. The terms 'aqueous compositions of the invention' (or alternatively 'inventive aqueous compositions') as used in the specification includes any and all of its preferments, combinations of its features and ranges as well as combinations of any and all of its preferments with any and all of the combinations of its features and ranges.

Thus, any and all of the inventive mixtures, inventive aqueous dispersions, aqueous compositions disclosed in this section 3 includes any and all of their preferments, combinations of their features and ranges as well as combinations of any and all of their preferments with any and all of the combinations of their features and ranges, are collectively referred to—in the entire specification including the claims—as the inventive mixtures, inventive aqueous dispersions, aqueous compositions.

The Inventive Mixtures

The inventive mixtures are according to any one of A22 to A25 and as disclosed in the entire specification including the claims. More specifically, the inventive mixture comprises:

i) particles of an (aziridinyl hydroxy)-functional organic component according to A1a or to any one of A1 to A21 or any combination derived from the disclosure in sections 1 and/or 3, and ii) a polymer which has an acid value determined according to the ASTM D1639-90(1996)e1 of at least 5 and at most 300, preferably at least 8 and at most 200, more preferably at least 10, and at most 150 mg KOH/g and wherein the polymer may optionally comprise ionic functional groups.

The mixtures of the invention may be solid, semi-solid or liquid at standard conditions. The mixtures of the invention may be prepared by mixing:

i) the particles of the invention, and ii) a polymer which has an acid value determined according to the ASTM D1639-90(1996)e1 in the range from 5 to 300, preferably from 8 to 200, more preferably from 10 to 150 mg KOH/g and wherein the polymer may optionally comprise ionic functional groups.

The mixing of the components i) and ii) may be carried out in the presence of water and/or an organic solvent at standard conditions, in order to obtain a liquid mixture. Alternatively, the mixing may be carried out by direct mixing of the components i) and ii) at standard conditions.

Preferably, the polymer is selected from the group consisting of polyesters, polyamides, polycarbonates, polyimides, alkyds, uralkyds, polyacrylics, polyurethanes, poly(urethane-acrylic)s, and mixtures thereof, preferably the polymer is selected from the group consisting of polyamides, polyacrylics, polyurethanes, poly(urethane-acrylic)s, and mixtures thereof, most preferably the polymer is selected from the group consisting of polyacrylics, polyurethanes, poly(urethane-acrylic)s, and mixtures thereof.

Preferably, the polymer is present in an amount of at least 5 and at most 65, preferably at least 10 and at most 60, more preferably at least 20, and at most 55, for example at least 30 and at most 50 wt % on the total weight of the aqueous composition, and wherein the total amount of all the components that make up the mixture totals 100 wt %.

Preferably, the particles are present in an amount of at least 10 and at most 100, preferably at least 15 and at most 95, more preferably at least 20 and at most 90, for example at least 25 and at most 85, for examples at least 30 and at most 80, for example at least 35 and at most 75, for example at least 40 and at most 70, for example at least 40 and at most 65, for example at least 40 and at most 60, and wherein the total amount of all the components that make up the mixture totals 100 wt %.

The mixtures of the invention may be cured at standard conditions for example 12-48 h (preferably 24-48 h), and/or by heat-curing at elevated temperatures and at atmospheric pressure for example 70-80° C. for 10-60 minutes (preferably 15-30 minutes, more preferably 20 minutes), and/or any combination of curing at room temperature and curing at elevated temperatures; annealing steps (e.g. 50° C. for 16 h) may also be included especially in between curing at elevated temperatures and at atmospheric pressure and curing at standard conditions, wherein the annealing step follows the curing at elevated temperatures and at atmospheric pressure. Such inventive mixtures may preferably be cured at a temperature of at least 0 and at most 85, preferably at least 15 and at most 80, more preferably at least 23 and at most 70, most preferably at least 30 and at most 85, for example at least 15 and at most 30° C., for time periods that may vary and are preferably of at most 60, more preferably at most 30, even more preferably at most 15 minutes.

Obviously, curing at elevated temperatures and at atmospheric pressure requires shorter curing time; curing may also be effected by using pressure or by applying vacuum, or by irradiation, e.g. UV-radiation, or by any combination thereof.

The inventive mixtures may optionally (further) comprise other components, such as pigments and/or waxes, and/or the usual (processing) additives, for example degassing agents—if the particles are used in powder coatings—, smoothness, appearance enhancing agents or (light) stabilizers. Suitable stabilizers include for example primary and/or secondary antioxidants and UV stabilizers, for example quinones, (sterically hindered) phenolic compounds, phosphonites, phosphites, thioethers and HALS (hindered amine light stabilizers). Examples of suitable degassing agents include cyclohexane dimethanol bisbenzoate, benzoin.

The Inventive Aqueous Dispersions

The inventive aqueous dispersions are according to any one of A26 to A34 and as disclosed in the entire specification including the claims. More specifically, the inventive aqueous dispersions have a pH determined according to the ISO 976:2013 and according to the description, of at least 7.5 and at most 14.0, preferably at least 8.0 and at most 14.0, for example at least 8.5 and at most 13.5, for example at least 9.0 and at most 13.0, for example at least 9.2 and at most 12.5, for example at least 9.4 and at most 12.0, for example at least 9.6 and at most 11.6, for example at least 10.5, and at most 11.5, and wherein the aqueous dispersion comprises:

i) water, and ii) particles according to any one of the claims 1-21, which particles are dispersed in the water.

Preferably, the water is present in an amount of at least 30 and at most 95, preferably at least 45 and at most 85, for example at least 50, and at most 70, for example at least 55 and at most 65 wt % on the total weight of the aqueous dispersion, and wherein the total amount of all the components that make up the aqueous dispersion totals 100 wt %.

Preferably, the inventive aqueous dispersions, further comprise an organic solvent in an amount of at most 40, preferably at most 30, for example at most 25, for example at most 20, for example at most 12, for example at most 10, for example at most 8, for example at most 5, for example at most 4, for example at most 3, for example at most 2, for example at most 1, for example at most 0.5, for example at most 0.2, for example at most 0.1 wt % on the total weight of the aqueous dispersion.

Preferably, the inventive aqueous dispersion is free of an organic solvent.

Preferably, the particles are present in an amount of at least 5 and at most 70, preferably at least 10 and at most 60, more preferably at least 20 and at most 55, for example at least 25 and at most 55, for example at least 30 and at most 55, for example at least 35 and at most 55, for example at least 35 and at most 50, for example at least 35 and at most 45 wt % on the total weight of the aqueous dispersion, and wherein the total amount of all the components that make up the aqueous dispersion totals 100 wt %.

Preferably, the inventive aqueous dispersions comprise a component T selected from the group consisting of: i) organic compounds having a molecular weight determined via MALDI-TOF MS according to the description, lower than 600 Da and comprising at least one aziridine ring, and ii) mixtures thereof, in an amount, determined via LC-MS according to the description, of at most 5, preferably at most 4, more preferably at most 3, for example at most 2, for example at most 1, for example at most 0.5, for example at most 0.1, for example at most 0.05 wt % on the total weight of the AZ-compound.

Preferably, the inventive aqueous dispersions are free of component T.

Preferably, the amount of chloride determined according to the ASTM D1726-11(2019), in the inventive aqueous dispersions is at most 0.3, preferably at most 0.2, more preferably at most 0.1, for example at most 0.05, for example at most 0.03 wt % on the total weight of the aqueous dispersion.

Preferably, the inventive aqueous dispersions are aqueous coating dispersions.

The inventive aqueous dispersions may be prepared by several ways. For example, one approach involves the preparation of the AZ-component in solvent and after purification (for instance by distilling off the excess of aziridine-AZIR), the AZ-component is being introduced into water wherein optionally surfactants/dispersants, surface tension modifiers, defoamers, solvents, thickeners and/or any other additives may also be present. The introduction of the AZ-component into the water can be done by using at least one surfactant (preferably at least one non-ionic surfactant) and adding the AZ-component to water with good mixing. Usually, a high shear mixer is most suitable for this process to ensure thorough mixing. If desired and if present, the solvent can be partly or completely distilled off. It is preferred to use a base during this process to ensure good retention of the aziridine groups. Preferably, part or all of the base (intended to be used) is added to the AZ-component prior to dispersing into water. Preferably, a volatile organic base is added to the AZ-component, and an inorganic base is added to the water prior to the AZ-component is being introduced into the water. Alternatively, and often preferred, the water wherein optionally surfactants/dispersants, surface tension modifiers, defoamers, solvents, thickeners and/or any other additives may also be present, is slowly added to the AZ-component, and after phase inversion, the mixture is further diluted with water to obtain the aqueous dispersions of the invention. Preferably, the pH of the thus prepared aqueous compositions of the invention should be at least 7.5 and at most 14.0, preferably at least 8.0 and at most 14.0, for example at least 8.5 and at most 13.5, for example at least 9.0 and at most 13.0, for example at least 9.2 and at most 12.5, for example at least 9.4 and at most 12.0, for example at least 9.6 and at most 11.6. In order to achieve that, it is preferred that the pH can be adjusted with base, preferably inorganic or organic base. The inventive aqueous dispersions preferably comprise ammonia, and/or a secondary amine, and/or a tertiary amine, and/or LiOH, and/or NaOH and/or KOH to adjust the pH to the desired value. Preferred amines are ammonia, dimethyl ethanolamine, diisopropylamine, isopropanol amine, diethyl ethanolamine, N,N dimethyl isopropanol amine, 3-dimethylamino-1-propanol, 2-[2-(dimethylamino)ethoxy} ethanol, N-ethyl morpholine and dimethyl benzylamine and triethylamine. An example of a preparation of an aqueous dispersion of the invention is shown in the Examples.

The inventive aqueous dispersions may be obtained by a process comprising the steps of:

a) mixing the AZ-component—as this is disclosed in the entire specification including the claims, with an organic solvent to obtain a mixture A; and b) mixing either the AZ-component component—as this is disclosed in the entire specification including the claims-, or the mixture A, with a dispersant to obtain a mixture B; and c) mixing either water and a base, or basic aqueous medium with the mixture B to obtain a mixture C; and d) optionally, (though preferably), removing the organic solvent from the mixture C to obtain a mixture D, and optionally mixing either additional water or a basic aqueous medium into the mixture D, to obtain the aqueous dispersion of the AZ-component.

Obviously, the particles of the invention (which form part of an aqueous dispersion of the invention) may be prepared by the process mentioned above.

The aqueous dispersions of the invention may be cured in the presence of a suitable polymer such as for example a polymer which has an acid value determined according to the ASTM D1639-90(1996)e1 in the range from 5 to 300, preferably from 8 to 200, more preferably from 10 to 150 mg KOH/g and wherein the polymer may optionally comprise ionic functional groups, at standard conditions for example 12-48 h (preferably 24-48 h), and/or by heat-curing at elevated temperatures and at atmospheric pressure for example 70-80° C. for 10-60 minutes (preferably 15-30 minutes, more preferably 20 minutes), and/or any combination of curing at room temperature and curing at elevated temperatures; annealing steps (e.g. 50° C. for 16 h) may also be included especially in between curing at elevated temperatures and at atmospheric pressure and curing at standard conditions, wherein the annealing step follows the curing at elevated temperatures and at atmospheric pressure. Such inventive mixtures may preferably be cured at a temperature of at least 0 and at most 85, preferably at least 15 and at most 80, more preferably at least 23 and at most 70, most preferably at least 30 and at most 85, for example at least 15 and at most 30° C., for time periods that may vary and are preferably of at most 60, more preferably at most 30, even more preferably at most 15 minutes.

Obviously, curing at elevated temperatures and at atmospheric pressure requires shorter curing time; curing may also be effected by using pressure or by applying vacuum, or by irradiation, e.g. UV-radiation, or by any combination thereof.

Such polymers may be selected from the group consisting of polyesters, polyamides, polycarbonates, polyimides, alkyds, uralkyds, polyacrylics, polyurethanes, poly(urethane-acrylic)s, and mixtures thereof, preferably the polymer is selected from the group consisting of polyamides, polyacrylics, polyurethanes, poly(urethane-acrylic)s, and mixtures thereof, most preferably the polymer is selected from the group consisting of polyacrylics, polyurethanes, poly(urethane-acrylic)s, and mixtures thereof.

The inventive aqueous dispersions may optionally (further) comprise other components, such as pigments and/or waxes, and/or the usual (processing) additives, for example degassing agents—if the particles are used in powder coatings—, smoothness, appearance enhancing agents or (light) stabilizers. Suitable stabilizers include for example primary and/or secondary antioxidants and UV stabilizers, for example quinones, (sterically hindered) phenolic compounds, phosphonites, phosphites, thioethers and HALS (hindered amine light stabilizers). Examples of suitable degassing agents include cyclohexane dimethanol bisbenzoate, benzoin.

The Inventive Aqueous Compositions

The inventive aqueous compositions are according to any one of A37 to A44 and as disclosed in the entire specification including the claims. More specifically, the inventive aqueous compositions comprise:

i) an aqueous dispersion according to any one of A26 to A34, and ii) a polymer which has an acid value determined according to the ASTM D1639-90(1996)e1 in the range from 5 to 300, preferably from 8 to 200, more preferably from 10 to 150 mg KOH/g and wherein the polymer may optionally comprise ionic functional groups.

Preferably, the aqueous composition has a pH of at least 7.5 and at most 14.0, preferably at least 8.0 and at most 14.0, for example at least 8.5 and at most 13.5, for example at least 9.0 and at most 13.0, for example at least 9.2 and at most 12.5, for example at least 9.4 and at most 12.0, for example at least 9.6 and at most 11.6.

Preferably, the polymer is selected from the group consisting of polyesters, polyamides, polycarbonates, polyimides, alkyds, uralkyds, polyacrylics, polyurethanes, poly(urethane-acrylic)s, and mixtures thereof, preferably the polymer is selected from the group consisting of polyamides, polyacrylics, polyurethanes, poly(urethane-acrylic)s, and mixtures thereof, most preferably the polymer is selected from the group consisting of polyacrylics, polyurethanes, poly(urethane-acrylic)s, and mixtures thereof.

Preferably, the inventive aqueous compositions further comprise an organic solvent in an amount of at most 35, preferably at most 30, for example at most 25, for example at most 20, for example at most 15, for example at most 12, for example at most 10, for example at most 8, for example at most 5, for example at most 4, for example at most 3, for example at most 2, for example at most 1, for example at most 0.5, for example at most 0.2, for example at most 0.1 wt % on the total weight of the aqueous composition.

Preferably, the aqueous dispersion is present in the inventive aqueous compositions in an amount of at least 0.1 and at most 50, preferably at least 0.2 and at most 45, more preferably at least 0.3 and at most 40, for example at least 0.4 and at most 35, for example at least 0.5 and at most 30, for example at least 0.6 and at most 25, for example at least 0.7 and at most 20, for example at least 0.8 and at most 15, for example at least 0.9 and at most 12, for example at least 1 and at most 10 for example at least 1.2 and at most 8, for example at least 0.3 and at most 25, for example at least 0.8 and at most 15, for example at least 1.5 and at most 12, for example at least 2.5 and at most 10, for example at least 3 and at most 8 wt % on the total weight of the aqueous composition, and wherein the total amount of all the components that make up the aqueous composition totals 100 wt %.

Preferably, the polymer is present in the inventive aqueous compositions in an amount of at least 5 and at most 65, preferably at least 10 and at most 60, more preferably at least 20 and at most 55, for example at least 30 and at most 50 wt % on the total weight of the aqueous composition, and wherein the total amount of all the components that make up the aqueous composition totals 100 wt %.

Preferably, the inventive aqueous compositions are free of an organic solvent.

Preferably, the inventive aqueous composition is a coating composition, more preferably an aqueous coating composition.

The aqueous compositions of the invention may be prepared by mixing the aqueous dispersions of the invention with aqueous dispersions of polymers. Preferably, this can be done by slowly adding and mixing an aqueous dispersion of the invention into an aqueous dispersion of a polymer. Alternatively, an aqueous dispersion of a polymer may be slowly added and mixed into an aqueous dispersion of the invention, or they may be mixed using an inline mixing device. Preferably, the aqueous dispersions of the invention comprise a surfactant (preferably a non-ionic surfactant) in order to facilitate and enable thorough mixing with the aqueous dispersion of the polymer. Preferably, the pH of the thus prepared aqueous compositions of the invention should be at least 7.5 and at most 14.0, preferably at least 8.0 and at most 14.0, for example at least 8.5 and at most 13.5, for example at least 9.0 and at most 13.0, for example at least 9.2 and at most 12.5, for example at least 9.4 and at most 12.0, for example at least 9.6 and at most 11.6. In order to achieve that, it is preferred that the aqueous dispersions of the invention have a pH of at least 7.5 and at most 14.0, preferably at least 8.0 and at most 14.0, for example at least 8.5 and at most 13.5, for example at least 9.0 and at most 13.0, for example at least 9.2 and at most 12.5, for example at least 9.4 and at most 12.0, for example at least 9.6 and at most 11.6, for example at least 10.5 and at most 11.5, and the aqueous dispersions of the polymers have a pH of at least 7.5 and at most 14.0, preferably at least 8.0 and at most 14.0, for example at least 8.5 and at most 13.5, for example at least 9.0 and at most 13.0, for example at least 9.2 and at most 12.5, for example at least 9.4 and at most 12.0, for example at least 9.6 and at most 11.6. Preferably, the polymers suitable for preparing the aqueous compositions of the invention are polymers which have an acid value determined according to the ASTM D1639-90(1996)e1 in the range from 5 to 300, preferably from 8 to 200, more preferably from 10 to 150 mg KOH/g and wherein the polymers may optionally comprise ionic functional groups; more preferably said polymers may be selected from the group consisting of polyesters, polyamides, polycarbonates, polyimides, alkyds, uralkyds, polyacrylics, polyurethanes, poly(urethane-acrylic)s, and mixtures thereof, preferably the polymer is selected from the group consisting of polyamides, polyacrylics, polyurethanes, poly(urethane-acrylic)s, and mixtures thereof, most preferably the polymer is selected from the group consisting of polyacrylics, polyurethanes, poly(urethane-acrylic)s, and mixtures thereof.

For example, an aqueous dispersion of a poly(acrylate-methacrylate) suitable for the preparation of an aqueous composition of the invention, may be prepared as follows: A 2-L four-necked flask equipped with a thermometer and overhead stirrer was charged with sodium lauryl sulphate (30% solids in water, 18.6 grams of solution) and demineralized water (711 grams). The reactor phase was placed under $N_2$ atmosphere and heated to 82° C. A mixture of: i) demineralized water (112 grams), ii) sodium lauryl sulphate (30% solids in water, 37.2 grams of solution), iii) methyl methacrylate (174.41 grams), iv) n-butyl acrylate (488.44 grams) and v) methacrylic acid (34.88 grams) was placed in a large feeding funnel and emulsified with an overhead stirrer (monomer feed). Ammonium persulphate (1.75 grams) was dissolved in demineralized water (89.61 grams) and placed in a small feeding funnel (initiator feed). Ammonium persulphate (1.75 grams) was dissolved in demineralized water (10.5 grams), and this solution was added to the reactor phase. Immediately afterwards, 5% by volume of the monomer feed was added to the reactor phase. The reaction mixture then exothermed to 85° C. and was kept at 85° C. for 5 minutes. Then, the residual monomer feed and the initiator feed were fed to the reaction mixture over 90 minutes, maintaining a temperature of 85° C. After completion of the feeds, the monomer feed funnel was rinsed with demineralized water (18.9 grams), and reaction temperature maintained at 85° C. for 45 minutes. Subsequently, the mixture was cooled to room temperature and brought to pH=7.5 with an ammonia solution (6.25 wt. % in demineralized water) and brought to 40% solids with the further addition of demineralized water.

The inventive aqueous compositions may be obtained by a process comprising the steps of:

a) mixing the AZ-component—as this is disclosed in the entire specification including the claims—, with an organic solvent to obtain a mixture A; and b) mixing either the AZ-component—as this is disclosed in the entire specification including the claims—, or the mixture A with a dispersant to obtain a mixture B; and c) mixing either water and a base, or basic aqueous medium with the mixture B to obtain a mixture C; and d) optionally, (though preferably), removing the organic solvent from the mixture C to obtain a mixture D, and optionally mixing either additional water or a basic aqueous medium into the mixture D, to obtain an aqueous dispersion of the AZ-component, and e) mixing the aqueous dispersion of the AZ-component with an aqueous dispersion of a polymer (wherein the polymer is as disclosed in this section and sub-section), to obtain the inventive aqueous composition.

The aqueous compositions of the invention may be cured at standard conditions for example 12-48 h (preferably 24-48 h), and/or by heat-curing at elevated temperatures and at atmospheric pressure for example 70-80° C. for 10-60 minutes (preferably 15-30 minutes, more preferably 20 minutes), and/or any combination of curing at room temperature and curing at elevated temperatures; annealing steps (e.g. 50° C. for 16 h) may also be included especially in between curing at elevated temperatures and at atmospheric pressure and curing at standard conditions, wherein the annealing step follows the curing at elevated temperatures and at atmospheric pressure. Such inventive aqueous compositions may preferably be cured at a temperature of at least 0 and at most 85, preferably at least 15 and at most 80, more preferably at least 23 and at most 70, most preferably at least 30 and at most 85, for example at least 15 and at most 30° C., for time periods that may vary and are preferably of at most 60, more preferably at most 30, even more preferably at most 15 minutes.

Obviously, curing at elevated temperatures and at atmospheric pressure requires shorter curing time; curing may also be effected by using pressure or by applying vacuum, or by irradiation, e.g. UV-radiation, or by any combination thereof.

The inventive aqueous compositions may optionally (further) comprise other components, such as pigments and/or waxes, and/or the usual (processing) additives, for example degassing agents—if the particles are used in powder coatings—, smoothness, appearance enhancing agents or (light) stabilizers. Suitable stabilizers include for example primary and/or secondary antioxidants and UV stabilizers, for example quinones, (sterically hindered) phenolic compounds, phosphonites, phosphites, thioethers and HALS (hindered amine light stabilizers). Examples of suitable degassing agents include cyclohexane dimethanol bisbenzoate, benzoin.

4. Other Aspects and Embodiments of the Invention

In yet another aspect, the invention provides for a kit-of-parts comprising parts A and B which are physically separated from each other, wherein:

i) the part A comprises an aqueous dispersion according to any one of A26 to A34 or any combination derived from the disclosure in sections 1 and 3 and as disclosed in the entire specification including the claims, and ii) the part B comprises a polymer which has an acid value determined according to the ASTM D1639-90(1996)e1 in the range from 5 to 300, preferably from 8 to 200, more preferably from 10 to 150 mg KOH/g and wherein the polymer may optionally comprise ionic functional groups, and wherein the polymer is preferably selected from the group consisting of polyesters, polyamides, polycarbonates, polyimides, alkyds, uralkyds, polyacrylics, polyurethanes, poly(urethane-acrylic)s, and mixtures thereof, more preferably the polymer is selected from the group consisting of polyamides, polyacrylics, polyurethanes, poly(urethane-acrylic)s, and mixtures thereof, most preferably the polymer is selected from the group consisting of polyacrylics, polyurethanes, poly(urethane-acrylic)s, and mixtures thereof, wherein the part A does not comprise the polymer of the part B, and the part B does not comprise the aqueous dispersion of the part A.

In yet another aspect, the invention provides for a cured form of particles according to A1a or to any one of A1 to A22 or any combination derived from the disclosure in sections 1 and 3 and as disclosed in the entire specification including the claims; preferably the cured form is a film.

In yet another aspect, the invention provides for a cured form of a mixture according to any one of A22 to A25 or any combination derived from the disclosure in sections 1 and 3 and as disclosed in the entire specification including the claims; preferably the cured form is a film.

In yet another aspect, the invention provides for a cured form of an aqueous dispersion according to any one of A26 to A34 or any combination derived from the disclosure in sections 1 and 3 and as disclosed in the entire specification including the claims; preferably the cured form is a film.

In yet another aspect, the invention provides for a cured form of particles according to any one of A35 to A36 or any combination derived from the disclosure in sections 1 and 3 and as disclosed in the entire specification including the claims; preferably the cured form is a film.

In yet another aspect, the invention provides for a cured form of an aqueous composition according to any one of A37 to A45 or any combination derived from the disclosure in sections 1 and 3 and as disclosed in the entire specification including the claims; preferably the cured form is a film.

In yet another aspect, the invention provides for an article comprising:

i) particles according to A1a or to any one of A1 to A21 or any combination derived from the disclosure in section 1 and as disclosed in the entire specification including the claims, and/or ii) a mixture according to any one of A22 to A25 or any combination derived from the disclosure in sections 1 and 3 and as disclosed in the entire specification including the claims, and/or iii) an aqueous dispersion according to any one of A26 to A34 or any combination derived from the disclosure in sections 1 and 3 and as disclosed in the entire specification including the claims, and/or iv) particles according to any one of A35 to A36 or any combination derived from the disclosure in sections 1 and 3 and as disclosed in the entire specification including the claims, and/or v) an aqueous composition according to any one of A37 to A45 or any combination derived from the disclosure in sections 1 and 3 and as disclosed in the entire specification including the claims, and/or vi) a cured form according to the any one of A46 to A51 or any combination derived from the disclosure in sections 1 and 3 and as disclosed in the entire specification including the claims; preferably the article is selected from the group consisting of textile, glass, metal, composite, plastic, wood, engineered wood, wood-like, leather, artificial leather, paper, fibers.

In yet another aspect, the invention provides for a use of any one or any combination of the following:

- i) particles according to A1a or to any one of A1 to A21 or any combination derived from the disclosure in section 1 and as disclosed in the entire specification including the claims;
- ii) a mixture according to any one of A22 to A25 or any combination derived from the disclosure in sections 1 and 3 and as disclosed in the entire specification including the claims;
- iii) an aqueous dispersion according to any one of A26 to A34 or any combination derived from the disclosure in sections 1 and 3 and as disclosed in the entire specification including the claims;
- iv) particles according to any one of A35 to A36 or any combination derived from the disclosure in sections 1 and 3 and as disclosed in the entire specification including the claims;
- v) an aqueous composition according to any one of A37 to A45 or any combination derived from the disclosure in sections 1 and 3 and as disclosed in the entire specification including the claims;

as a crosslinker.

In yet another aspect, the invention provides for a use of any one or any combination of the following:

- i) particles according to A1a or to any one of A1 to A21 or any combination derived from the disclosure in section 1 and as disclosed in the entire specification including the claims;
- ii) a mixture according to any one of A22 to A25 or any combination derived from the disclosure in sections 1 and 3 and as disclosed in the entire specification including the claims;
- iii) an aqueous dispersion according to any one of A26 to A34 or any combination derived from the disclosure in sections 1 and 3 and as disclosed in the entire specification including the claims;
- iv) particles according to any one of A35 to A36 or any combination derived from the disclosure in sections 1 and 3 and as disclosed in the entire specification including the claims;
- v) an aqueous composition according to any one of A37 to A45 or any combination derived from the disclosure in sections 1 and 3 and as disclosed in the entire specification including the claims;
- vi) a kit-of-parts according to A45 or any combination derived from the disclosure in sections 1 and 3 and as disclosed in the entire specification including the claims;
- vii) a cured form according to any one of A46 to A47 or any combination derived from the disclosure in sections 1 and 3 and as disclosed in the entire specification including the claims;
- viii) an article according to any one of A52 to A53 or any combination derived from the disclosure in sections 1 and 3 and as disclosed in the entire specification including the claims;

in coatings, paints, inks, varnishes, lubricants, adhesives, additive manufacturing, 3D-printing, textiles, waxes, fuels, photography, plastics, medical compositions, medical devices.

Yet, another aspect of the invention is any one of the particles shown in the Examples that is according to the invention (Examples 1, 2, 3, 4, 5 and 6).

Yet, another aspect of the invention is any one of the liquid compositions shown in the Examples that is according to the invention (Examples 1, 2, 3, 4, 5, and 6).

Yet, another aspect of the invention is any one of the aqueous dispersions shown in the Examples that is according to the invention (Examples 1, 2, 3, 4, 5 and 6).

Many other variations and embodiments of the invention will be apparent to those skilled in the art, and such variations are contemplated within the scope of the claims.

Any feature, element, component, embodiment, range and especially any preferred feature, preferred element, preferred embodiment, preferred range, preferred combination of ranges, preferment described in the entire specification including the claims can be combined with each other.

Further aspects of the invention and preferred features thereof are given in the claims in the specification.

The invention will now be described in detail with reference to the following non-limiting examples, which are by way of illustration only.

EXAMPLES

The invention is explained in more detail with reference to the following non-limiting examples.

All the Examples shown in this section were carried out in a controlled laboratory environment at standard conditions (as these are defined in the specification), a relative humidity of 50±1% and an airflow of 0.1 m/s, unless otherwise explicitly specified.

1.1 Chemicals, Raw Materials and Other Materials

Triethylamine (purity 99.7%) was supplied by ARKEMA. Propylene imine (purity 99.0%) was supplied by Menadiona. Anhydrous potassium carbonate ($K_2CO_3$; purity 99.0%) was supplied by Alfa Aesar. The trimethylolpropane tris(2-methyl-1-aziridinepropionate) (CAS No. 64265-57-2; see structure in Example 1C) was supplied by DSM (commercial product name 'crosslinker CX-100'). The NeoCryl® B-300 is a methacrylic copolymer of methyl methacrylate (MMA) and butyl-methacrylate (BMA) (acid value lower than 1 mg KOH/g, $T_g$: 45° C., theoretical molecular weight 16000 Da, density at 20° C.: 1.14 g/cm$^3$, viscosity at 25° C. (40 wt % in 1,6-hexanediol diacrylate (HDDA)): 0.8-1.0 Pa·s; form at 25° C.: white solid) supplied by DSM. The DESMODUR® N 3600 is a low viscosity aliphatic polyisocyanate (trimer) based on hexamethylene diisocyanate (HDI) (NCO content: 23.0±0.5% (M105-ISO 11909); viscosity at 23° C.: 1200±300 mPa·s (M014-1S03219/A.3); color value (Hazen): 40 (M017-EN 1557); monomeric HDI:

≤0.25% (M106-1S0 10283); equivalent weight: approx. 183; flash point: approx. 159° C. (DIN 53213/1); density at 20° C.: approx. 1.16 g/ml (DIN EN ISO 2811), supplied by Covestro. The DESMODUR® N 3900 is a low viscosity aliphatic polyisocyanate based on hexamethylene diisocyanate (HDI) (NCO content: 23.0±0.5% (M105-ISO 11909); viscosity at 23° C.: 730±100 mPa·s (M014-1S0 3219/A.3); color value (Hazen): 40 (M017-EN 1557); monomeric HDI: 0.25% (M106-1S0 10283); equivalent weight: approx. 179; flash point: approx. 203° C. (DIN 53213/1); density at 20° C.: approx. 1.15 g/ml (DIN EN ISO 2811), supplied by Covestro. The ERISYS® GE-36 is a triglycidyl ether of propoxylated glycerine (see Scheme 1) (EEW: 620-680 g/eq; viscosity: 200-320 cps at 25° C.; hydrolysable chloride: <0.10%; flash point: >93° C., residual epichlorohydrin: <20 ppm) was supplied by CVC Thermoset Specialties (now HUNTSMAN). The ERISYS® GA-240 (see Scheme 2) is glycidyl amine of m-xylelenediamine (CAS No. 63738-22-7) (epoxy equivalent weight (EEW): 95-110 g/eq; specific gravity at 25° C.: 1.14-1.16 g/ml; flash point: >215° C.; colour (Gardner): max. 5; viscosity at 25° C.: 1600-3000 cP) supplied by CVC Thermoset Specialties (now HUNSTMAN). The Cardolite® NC-514S is a di-functional glycidyl ether epoxy resin (see Scheme 3) [reddish brown liquid; color (Gardner): (ASTM D1544); viscosity at 25° C.: 1000-3000 cP (ASTM D2196); epoxy equivalent weight (EEW): 320-420 (ASTM D1652-97); hydrolysable chlorine (%): 0.5 (ASTM D1726-11); volatile loss (% wt): 0.5 (ASTM D2369-98); density at 25° C.: 1.026 Kg/L (ASTM D1475); flash point: >205° C. (ASTM D93)] was supplied by Cardolite Corporation. The EPPALOY® 9000 is tris hydroxyl phenyl ethane (CAS No. 87093-13-8) (see Scheme 4) [average epoxy functionality: 3.0; epoxy equivalent weight (EEW): 160-180 g/eq; viscosity at 72° C.: 5500-6500 cP; colour (Gardner): max. 2) supplied by CVC Thermoset Specialties (now HUNSTMAN]. The bisphenol A diglycidyl ether (CAS No. 1675-54-3) was supplied from Tokyo Chemical Industry Co., Ltd. The N,N-diglycidyl-4-glycidyloxyaniline (CAS No. 5026-74-4) was supplied by Sigma-Aldrich. The ATLAS™ G-5000 (non-ionic dispersant) is a polyalkylene glycol ether (colour: cream; solidification point: approx. 30 (DGF method III 46 (57); relative density at 25° C.: approx. 1.0; hydrophilic-lipophilic balance (HLB) value: 16.9; form at 25° C.: waxy solid; acid value: max. 0.3 mg KOH/g; hydroxyl value: 18-22 mg KOH/g) supplied by Croda. The ATLAS™ G-5002L-LQ (non-ionic dispersant) is a block copolymer of ethylene oxide and propylene oxide, terminated by a butoxy group (cloud point: 60.6; form at 25° C.: liquid; acid value: max. 0.3 mg KOH/g; hydroxyl value: 13-16 mg KOH/g; colour (Gardner) max. 4), supplied by Croda. Mehtylethylketone was supplied by Sigma-Aldrich. The polypropylene glycol with a calculated number average molecular weight ($M_e$) of 2000 Da and an OH-value of 56±2 mg KOH/g polypropylene glycol), and the polypropylene glycol with a calculated number average molecular weight ($M_n$) of 1000 Da and an OH-value of 112±2 mg KOH/g polypropylene glycol, were supplied by DOW. Any other chemical that is not explicitly mentioned in this paragraph and used in the Examples section (and unless otherwise stated in the specification) has been supplied by Sigma-Aldrich.

Scheme 1

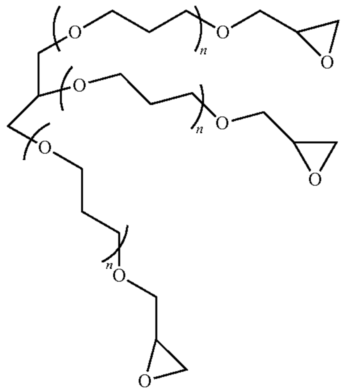

Scheme 2

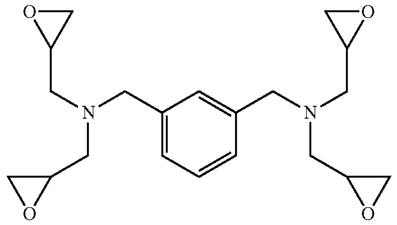

Scheme 3

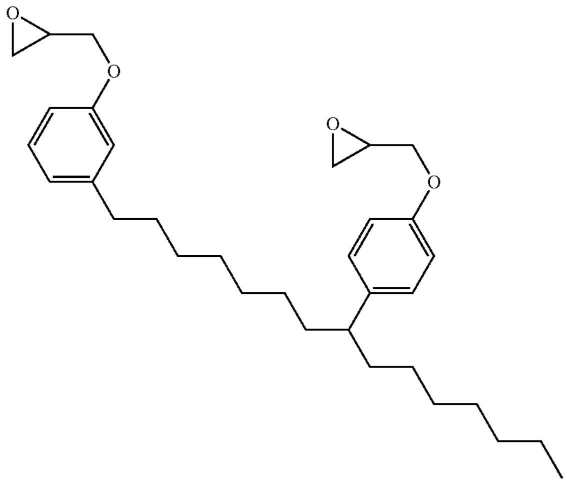

Scheme 4

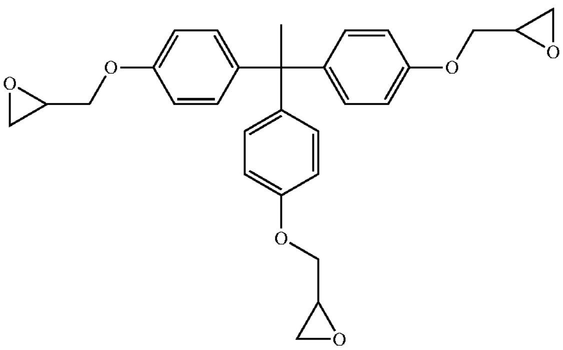

1.2 Preparation of the Polyurethane a and its Aqueous Dispersion (the Latter is Abbreviated as 'Polyurethane A-AQD')

A one-litre flask (equipped with a thermometer and an overhead stirrer), was charged with 29.9 grams of dimethylol propionic acid, 282.1 grams of polypropylene glycol with a calculated number average molecular weight (MO of 2000 Da and an OH-value of 56±2 mg KOH/g polypropylene glycol), 166.5 grams of polypropylene glycol with a calculated number average molecular weight ($M_n$) of 1000 Da and an OH-value of 112±2 mg KOH/g polypropylene glycol, and 262.8 grams of isophorone diisocyanate (the number average molecular weight of each of the polyols is calculated from its OH-value according to the equation: $M_n$=2*56100/[OH-value in mg KOH/g polypropylene glycol). The reaction mixture was placed under $N_2$ atmosphere, heated to 50° C. and subsequently, 0.07 g dibutyltin dilaurate were added to the reaction mixture. An exothermic reaction was observed; however, proper care was taken in order for the reaction temperature not to exceed 97° C. The reaction was maintained at 95° C. for an hour. The NCO content of the resultant polyurethane A was 7.00% on solids determined according to the ISO 14896 Method A (year 2009) (theoretically 7.44%), and the acid value of the polyurethane A was 16.1±1 mg KOH/g polyurethane A. The polyurethane A was cooled down to 60° C., and 18.7 grams of triethylamine were added, and the resulting mixture was stirred for 30 minutes. Subsequently, an aqueous dispersion of the polyurethane A (abbreviated as 'polyurethane A-AQD') was prepared as follows: the thus prepared mixture of the polyurethane A and triethylamine was fed—at room temperature over a time period of 60 minutes—to a mixture of 1100 grams of demineralized water, 19.5 grams of nonylphenol ethoxylate (9 ethoxylate groups), and 4.0 grams of triethylamine. After the feed was completed, the mixture was stirred for additional 5 minutes, and subsequently, 111.2 grams of hydrazine (16 wt % solution in water) were added to the mixture. The aqueous dispersion of the polyurethane A thus prepared was stirred for an additional 1 h.

1.3 Determination of the Molecular Weight of the AZ1- to AZ5-Compounds and of the Component T (Matrix-Assisted Laser Desorption/Ionization on a Time-of-Flight Mass Spectrometry; MALDI-TOF MS)

All MALDI-ToF-MS spectra were acquired using a Bruker UltrafleXtreme™ MALDI-ToF mass spectrometer. The instrument is equipped with a Nd:YAG laser emitting at 1064 nm and a collision cell (not used for these samples). Spectra were acquired in the positive-ion mode using the reflectron, using the highest resolution mode providing accurate masses (range 60-7000 m/z). Cesium Tri-iodide (range 0.3-3.5 kDa) was used for mass calibration (calibration method: IAV Molecular Characterization, code MC-MS-05). The laser energy was 20%. The samples were dissolved in THF at approx. 50 mg/mL. The matrix used was: DCTB (trans-2-[3-(4-tertbutylphenyl)-2-methyl-2-propenylidene]malononitrile), CAS Number 300364-84-5. The matrix solution was prepared by dissolving 20 mg in 1 mL of THF. Potassium trifluoroacetate (KTFA, CAS Number: 2923-16-2) or alternatively sodium iodide was used as salt (NaI, CAS Number 7681-82-5); 10 mg was dissolved in 1 ml THF with a drop of MeOH added. Ratio sample:matrix: salt=10:200:10 (μL), after mixing, 0.5 μL was spot on MALDI plate and 20 allowed to air-dry. Reported signals are the major peaks within 0.5 Da of the calculated mass of the multi-aziridine compounds which are theoretically present in the composition in the largest amounts. In all cases, the reported peaks are the sodium or potassium adducts of the measured ions. The MALDI-TOF MS signals reported correspond to the major peaks of the sodium or potassium adducts of the measured ions of the theoretical formula of a multi-aziridine compound (the sodium and potassium cations. The theoretical formula of a multi-aziridine compound may be determined via analytical techniques well-known to one skilled in the art of analytical chemistry, e.g. NMR spectroscopy and/or liquid chromatography-mass spectroscopy (LC-MS), and/or liquid chromatography-mass spectroscopy-mass spectroscopy (LCMS-MS), and/or theoretically from its method of preparation (if reactants and conditions are known); once the theoretical formula of a multi-aziridine compound is determined, then its theoretical molecular weight may also be determined.

The multi-aziridine compounds are identified by comparing the molecular weight which is defined just below (MW), with the exact molecular mass (i.e. the sum of the non-isotopically averaged atomic masses of its constituent atoms) of a theoretical structure, using a maximum deviation of 0.5 Da. In the context of this specification, the molecular weight (MW) attributed to a multi-aziridine compound is calculated from the following equation:

$$MW = Obs \cdot [M + M_{cation}] - [M_{cation}]$$

wherein the $M_{cation}$ is the exact molar mass of the sodium (22.99 Da), or potassium cation (38.96 Da) (depending on which cation was used in the MALDI-TOF MS method), and the Obs.+[$M_{cation}$] is the MALDI-TOF MS signal (peak) which corresponds to the theoretical formula of the multi-aziridine compound.

1.4 Determination of the Scatter Intensity-Based Average Hydrodynamic Diameter of the Particles (Dynamic Light Scattering-DLS')

The scatter intensity-based average hydrodynamic diameter ($D_H$) of the particles was determined using a method derived from the ISO 22412:2017 standard with a Malvern Zetasizer Nano S90 DLS instrument that was operated under the following settings. As material, a polystyrene latex was defined with a RI 1.590 and absorption of 0.10 with a continuous of a medium of demineralized water with a viscosity of 0.8812 cP and a RI of 1.332 at 25° C. Measurements were performed in DTS0012 disposable cuvettes, obtained from Malvern Instruments (Malvern, Worcestershire, United Kingdom). The measurements were performed under a 173° C. back-scatter angle as an average of 3 measurements after 120 seconds equilibration, consisting of 10-15 sub-runs optimized by the machine itself. The focus point of the laser was at a fixed position of 4.65 cm, and data were analyzed using a general-purpose data fitting process. Samples were prepared by diluting 0.05 g sample (aqueous dispersion) in approximately 5 mL of demineralized water. If the sample still looks hazy, it is further diluted with distilled water until it becomes almost transparent.

1.5 Assessment of the Chemical Resistance

The starting and end chemical resistance of a film (cured coating) was tested based on the DIN 68861-1:2011-01.

The film was prepared as follows: an amount of a sample of an aqueous dispersion and an amount of the polyurethane A-AQD were mixed together under continuous stirring; these amounts were calculated on the basis that the molar ratio of the mol of aziridine rings present in the organic compound (or a mixture of organic compounds) bearing aziridine ring(s), e.g. AZ-component to the mol of carboxylic acid functional groups present in the polyurethane A was equal to 0.9. Upon completion of the mixing, the resulting mixture was stirred for additional 30 minutes to thus produce an aqueous coating composition. This aqueous coating composition was filtered and subsequently applied onto Leneta test cards using a 100 μm wire rod applicator. The film was subsequently dried for 1 h at 25° C. and then annealed at 50° C. for 16 h.

Cotton wool pads (1×1 cm) were soaked in a solution of ethanol: demineralized water (1:1). They were then placed on the films and covered with Petri dishes for 1 h. Afterwards, the pads and the Petri dishes were removed; after 1 h the coatings were visually inspected for damages; the extent of damages was assessed according to the following rating scheme:

5: no visible changes
4: hardly noticeable changes in shine or colour
3: slight changes in shine or colour; the structure of the test surface has not changed
2: heavy changes noticeable; however, the structure of the test surface has remained more or less undamaged.
1: heavy changes noticeable; the structure of the test surface has changed.
0: the tested surface was heavily changed or destroyed.

In the context of this specification, the above integers 0-5 are mentioned as 'ranking points'.

The chemical resistance of a reference film (prepared from only polyurethane A-AQD) was poor (this applies for all examples inventive and comparatives shown in the Examples).

1.6 Assessment of the Storage Stability and Crosslinking Efficiency

The storage stability of organic compounds bearing aziridine ring(s) in aqueous compositions[or equally the storage stability of aqueous dispersions comprising organic compounds bearing aziridine ring(s)] was assessed by viscosity measurements (starting and end viscosities) and determination of the chemical resistance (starting and end chemical resistance) as both are explained in the specification.

The crosslinking efficiency of organic compounds bearing aziridine ring(s) in aqueous compositions [or equally the crosslinking efficiency of aqueous dispersions comprising organic compounds bearing aziridine ring(s)] was assessed by determining the end chemical resistance of films (cured coatings).

Step 1

An aqueous dispersion comprising organic compounds bearing aziridine ring(s) was prepared, and its starting viscosity was determined as described in the specification.

In addition, the starting chemical resistance of said aqueous dispersion was also determined as described in the specification.

Step 2

Afterwards, the aqueous dispersion was stored in an oven at 50° C. for 4 weeks. Upon the expiration of this time period, the aqueous dispersion was removed from the oven and left to cool down to room temperature.

Subsequently:

i) the end viscosity of the aqueous dispersion was determined as described in the specification, and
ii) the end chemical resistance of the aqueous dispersion was determined as described in the specification.

For obvious reasons, an entity that gels during storage for a prolonged time period and at elevated temperature is deemed not to have enhanced storage stability because it is deemed not to have a workable viscosity.

For obvious reasons, an entity that gels during storage for a prolonged time period and at elevated temperature is deemed to have poor crosslinking efficiency.

1.7 Determination of the Apparent Viscosity

The starting and end apparent viscosities (or equally the starting and end viscosities) were measured at room temperature at 60 rpm, according to ISO 2555-2018 on a Brookfield DVE-LV viscometer (single-cylinder geometry). The spindle was selected from the spindles S62, S63 or S64, using the lowest-numbered spindle (i.e. the largest spindle) that yields a reading between 10% and 100% torque.

1.8 Determination of the pH

The pH of a sample was determined according to the ISO 976:2013. Samples were measured at room temperature using a Metrohm 691 pH-meter equipped with a combined glass electrode and a PT-1000 temperature sensor. The pH-meter was calibrated using buffer solutions of pH 7.00 and 9.21 prior to use.

1.9 Determination of the Acid Value

The acid value of a polymer is determined according to the ASTM D1639-90(1996)e1. According to the procedure, the sample was dissolved in a good solvent, was titrated with alcoholic potassium hydroxide solution of a known concentration (KOH). The difference in titration volume between the sample and a blank is the measure of the acid value on solids, according to the following formula:

$$AV = [(V_{blank} - V_{sample}) * N_{KOH} * 56.1]/(W * S/100)$$

where

AV is the acid number on solids in mg KOH/g solid material, $V_{blank}$ is the volume of KOH solution used in the blank, $V_{sample}$ is the volume of KOH solution used in the sample, $N_{KOH}$ is the normality of the KOH solution, W is the sample weight in grams and S is the solids content of the sample in %. Measurements are performed in duplicate using a potentiometric endpoint on a Metrohm 702SM Titrino titrator (accepting the measurement if the difference between duplicates is <0.1 mg KOH/g solid material).

1.10 Determination of the NCO Content

The NCO content of a sample is determined based on the ASTM D2572-19. In the procedure, the sample is reacted with excess n-dibutylamine. The excess of n-dibutylamine is subsequently back-titrated with standard 1N hydrochloric acid (HCl). The difference in titration volume between the sample and a blank is the measure of the isocyanate content on solids, according to the following formula:

$$\% \ NCO_{solids} = [(V_b - V_m) * N * 4.2] / (A * s/100)$$

where $\% \ NCO_{solids}$ is the isocyanate content on solids, $V_b$ is the volume of HCl used in the blank, $V_m$ is the volume of HCl used in the sample, N is the normality of the HCl solution, A is the sample weight in grams and s is the solids content of the sample in %. Measurements are performed in duplicate using a potentiometric endpoint on a Metrohm 702SM Titrino titrator (accepting the measurement if the difference between duplicates is $<0.1\%_{NCO}$).

1.11 Determination of the Amount of Component T [Liquid Chromatography Coupled with Mass Spectroscopy (LC-MS)]

The amount of component T (as the latter is defined in the specification including the claims; wt % on the total weight of the AZ-compound) was determined via liquid chromatography coupled with mass spectroscopy (LC-MS). Initially, a 0.01 wt % solution of sample in methanol was prepared. Subsequently, 0.5 μL of this solution was injected into an Agilent 1290 Infinity II Ultra High Pressure Liquid Chromatography (UHPLC) system equipped with: a) a High Strength Silica (HSS) technology $C_{18}$ type T3 column supplied by Waters® [100×2.1 mm (length×diameter); 1.8 micron average particle size of the stationary phase] operating at 40° C., and b) an Agilent 6550 iFunnel QTOF detector [ElectroSpray Ionization-Time-of-Flight Mass Spectrometer (ESI-TOF-MS) detector]. Once the sample was injected, then a gradient of a mobile phase [from 80/20 v/v A/B to 1/99 v/v A/B, wherein A was 10 mM $CH_3COO^-NH_4^+$ (set to pH 9.0 with $NH_3$) and B was acetonitrile; A and B making up the mobile phase], at a flow rate of 0.5 mL/min, for 10 min, was used to separate the various ingredients of the sample. Subsequently, a gradient of a mobile phase [from 1/99 v/v A/B to 1/49/50 A/B/C, wherein A was 10 mM $CH_3COO^-NH_4^+$ (set to pH 9.0 with $NH_3$), B was acetonitrile and C was tetrahydrofuran (THF); A, B and C making up the mobile phase] at a flow rate of 0.5 mL/min, for 5 min was applied to purge the column. Assuming a linear MS response of all the ingredients of the sample over all response ranges and an equal ionization efficiency for all the ingredients of the sample, the signals of the:

total ion current, and extracted ion chromatograms of the component T, were integrated.

The data acquisition was carried out via the MassHunter Build 10.1.48 software supplied by Agilent, while the data processing was carried out via the Qualitative Analysis Build 10.0.10305.0 software, also supplied by Agilent.

The amount of component T (wt % on the total weight of the AZ-compound) was determined by dividing the integrals of the extracted ion chromatograms of the component T by the integrals of the total ion current, multiplied by 100.

1.12 Determination of the Amount of Chloride

The amount of chloride in an aqueous dispersion was determined according to the ASTM D1726-11(2019).

2. INVENTIVE EXAMPLES

Example 1

100 grams of ERISYS® GE-36, 26.5 grams of propylene imine and 5 grams of potassium carbonate were charged to a reaction flask equipped with a thermometer and a condenser connected to a cryostat (3° C.). The mixture was stirred with a mechanical upper stirrer under a nitrogen atmosphere. The mixture was then heated to 80° C. Samples were taken at regular intervals, and the reaction progress was monitored using a $^1$H-NMR until no signal (chemical shifts) correlated to the epoxide protons from the multifunctional epoxide was observed. The reaction mixture was diluted with toluene and filtered. The solvent and the excess of propylene imine were removed from the filtrate in vacuo to obtain from the filtrate was removed in vacuo to obtain a clear highly viscous liquid. The theoretical formula of the thus prepared (aziridinyl hydroxy)functional organic compound is shown below (wherein x+y+z=33), and the theoretical molecular weight was calculated to be 2346.68 Da.

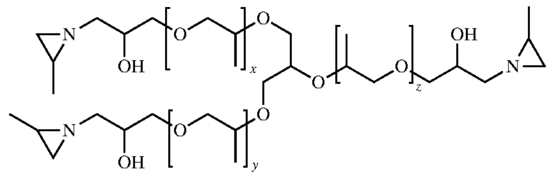

The molecular weight as defined and determined via MALDI-TOF MS—as this is defined and described in the specification—was 2346.50 Da (=Obs. $[M+M_{Na+}]$).

Subsequently, 15 grams of the (aziridinyl hydroxy)-functional organic compound obtained above was mixed with 3.2 grams of methylethylketone and incubated at 50° C. until a homogeneous solution was obtained. 0.03 grams of triethylamine (TEA) and 3 grams of molten ATLAS™ G-5000 (dispersant) were added to the solution. The resulting mixture was stirred for 5 minutes at room temperature using an IKA T25 Digital Ultra-Turrax® mixer with S 25 N-18G head at 2000 rpm. Then, stirring was increased to 10000 rpm and 15 grams of demineralized water and triethylamine, were added gradually to the mixture over 15 minutes in order to adjust the pH to 11. During this addition process, the mixer was moved around the reaction vessel continuously. After completion of the addition, the resulting dispersion was stirred at 5000 rpm for 10 more minutes, and the pH of the dispersion was again adjusted to 11 with triethylamine. The aqueous dispersion thus prepared contained the inventive particles (which were dispersed in the water).

The inventive particles had a scatter intensity-based average hydrodynamic diameter ($D_H$) of 275 nm.

Assessment of Storage Stability and Crosslinking Efficiency

Starting viscosity (spindle S62): 260 mPa·s

End viscosity (spindle S62): 320 mPa·s

The end viscosity was 1.23 times higher (end viscosity/starting viscosity=1.23) than the starting viscosity.

Thus, the aqueous dispersion had a workable viscosity.

The starting chemical resistance was very good.

The end chemical resistance was very good.

The end chemical resistance was equal to the starting chemical resistance.

The crosslinking efficiency was very good.

Given the above results, the inventive particles and/or the inventive aqueous dispersion comprising the inventive particles had surprisingly enhanced storage stability for a prolonged time period and at elevated temperature (4 weeks at 50° C.) because:

i) they had a workable viscosity, and ii) the end chemical resistance was equal to the starting chemical resistance, at the same time maintained very good crosslinking efficiency because the end chemical resistance was very good.

Example 2

30.0 grams of Cardolite® NC-514S, 19.2 grams of propylene imine, 30 grams of toluene and 3 grams of potassium carbonate were charged to a reaction flask equipped with a thermometer and a condenser connected to a cryostat (3° C.). The mixture was stirred with a mechanical stirrer under a nitrogen atmosphere. The mixture was then heated to 70° C. Samples were taken at regular intervals, and the reaction progress was monitored using a $^1$H-NMR until no signal (chemical shifts) correlated to the epoxide protons from the multifunctional epoxide was observed. After 20 hours of reaction, the mixture was diluted with toluene and filtered. The solvent and the excess of propylene imine were removed from the filtrate in vacuo to obtain a highly viscous brownish oil. The theoretical formula of the thus prepared (aziridinyl hydroxy)-functional organic compound is shown below, and the theoretical molecular weight was calculated to be 622.47 Da.

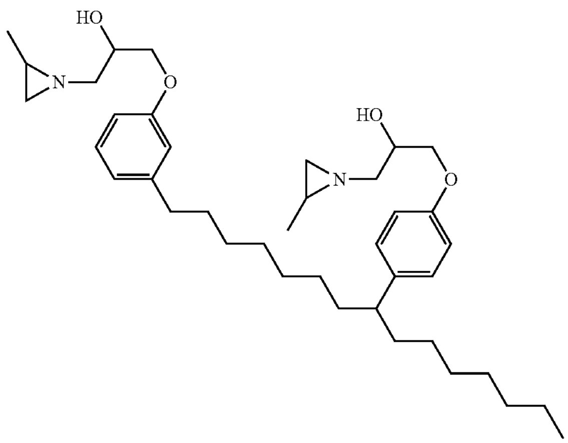 [SMILES: CCCCCCCC(CCCCCCCc1cccc(OCC(O)CN2CC2C)c1)c1ccc(OCC(O)CN2CC2C)cc1]

The molecular weight as defined and determined via MALDI-TOF MS—as this is defined and described in the specification—was 622.43 Da (=Obs. [M+$M_{Na+}$]−[$M_{Na+}$]).

Subsequently, 18.4 grams of the (aziridinyl hydroxy)-functional organic compound obtained above was mixed with 9.2 grams of methylethylketone and incubated at 50° C. until a homogeneous solution was obtained. 0.03 grams of triethylamine (TEA) and 3.7 grams of molten ATLAS™ G-5000 (dispersant) were added to the solution. The resulting mixture was stirred for 5 minutes at room temperature using an IKA T25 Digital Ultra-Turrax® mixer with S 25 N-18G head at 2000 rpm. Then, stirring was increased to 10000 rpm and 27.5 grams of demineralized water and triethylamine, were added gradually to the mixture over 15 minutes in order to adjust the pH to 11. During this addition process, the mixer was moved around the reaction vessel continuously. After completion of the addition, the resulting dispersion was stirred at 5000 rpm for 10 more minutes, and the pH of the dispersion was again adjusted to 11 with triethylamine. The aqueous dispersion thus prepared, contained the inventive particles (which were dispersed in the water).

The inventive particles had a scatter intensity-based average hydrodynamic diameter ($D_H$) of 181 nm.

Assessment of Storage Stability and Crosslinking Efficiency

Starting viscosity (spindle S62): 132 mPa·s

End viscosity (spindle S62): 138 mPa·s

The end viscosity was 1.05 times higher (end viscosity/starting viscosity=1.05) than the starting viscosity.

Thus, the aqueous dispersion had a workable viscosity.

The starting chemical resistance was good.

The end chemical resistance was good.

The end chemical resistance was equal to the starting chemical resistance.

The crosslinking efficiency was good.

Given the above results, the inventive particles and/or the inventive aqueous dispersion comprising the inventive particles had surprisingly enhanced storage stability for prolonged time period and at elevated temperature (4 weeks at 50° C.) because:

i) they had a workable viscosity, and ii) the end chemical resistance was equal to the starting chemical resistance, at the same time maintained good crosslinking efficiency because the end chemical resistance was good.

Example 3

30.0 grams of Cardolite® NC-514S, 19.2 grams of propylene imine, 30 grams of toluene and 3 grams of potassium carbonate were charged to a reaction flask equipped with a thermometer and a condenser connected to a cryostat (3° C.). The mixture was stirred with a mechanical stirrer under a nitrogen atmosphere. The mixture was then heated to 70° C. Samples were taken at regular intervals, and the reaction progress was monitored using a $^1$H-NMR until no signal (chemical shifts) correlated to the epoxide protons from the multifunctional epoxide was observed. After 20 hours of reaction, the mixture was diluted with toluene and filtered. The solvent and the excess of propylene imine were removed from the filtrate in vacuo to obtain a highly viscous brownish oil. The theoretical formula of the thus prepared (aziridinyl hydroxy)-functional organic compound is shown below, and the theoretical molecular weight was calculated to be 622.47 Da.

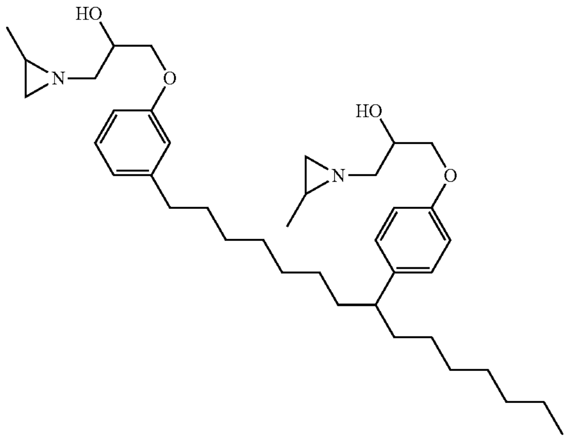 [SMILES: CCCCCCCC(CCCCCCCc1cccc(OCC(O)CN2CC2C)c1)c1ccc(OCC(O)CN2CC2C)cc1]

The molecular weight as defined and determined via MALDI-TOF MS—as this is defined and described in the specification—was 622.43 Da (=Obs. [M+$M_{Na+}$]−[$M_{Na+}$]).

Subsequently, 18.7 grams of the (aziridinyl hydroxy)-functional organic compound obtained above was mixed with 9.6 grams of acetone and incubated at 50° C. until a homogeneous solution was obtained. 0.03 grams of triethylamine (TEA) and 3.8 grams of Atlas™ G-5002L-LQ (dispersant) were added to the solution. The resulting mixture was stirred for 5 minutes at room temperature using an IKA T25 Digital Ultra-Turrax® mixer with S 25 N-18G head at 2000 rpm. Then, stirring was increased to 10000 rpm and 24.0 grams of demineralized water and triethylamine, were added gradually to the mixture over 15 minutes in order to adjust the pH to 11. During this addition process, the mixer was moved around the reaction vessel continuously. After completion of the addition, the resulting dispersion was stirred at 5000 rpm for 10 more minutes, and the pH of the dispersion was again adjusted to 11 with triethylamine. The aqueous dispersion thus prepared contained the inventive particles (which were dispersed in water).

The inventive particles had a scatter intensity-based average hydrodynamic diameter ($D_H$) of 153 nm.

Assessment of Storage Stability and Crosslinking Efficiency

Starting viscosity (spindle S62): 1178 mPa·s

End viscosity (spindle S62): 1212 mPa·s

The end viscosity was 1.03 times higher (end viscosity/starting viscosity=1.03) than the starting viscosity.

Thus, the aqueous dispersion had a workable viscosity.

The starting chemical resistance was good.

The end chemical resistance was good.

The end chemical resistance was equal to the starting chemical resistance.

The crosslinking efficiency was good.

Given the above results, the inventive particles and/or the inventive aqueous dispersion comprising the inventive particles had surprisingly enhanced storage stability for prolonged time period and at elevated temperature (4 weeks at 50° C.) because:

i) they had a workable viscosity, and ii) the end chemical resistance was equal to the starting chemical resistance, at the same time maintained good crosslinking efficiency because the end chemical resistance was good.

Example 4

30.0 grams of Cardolite® NC-514S, 19.2 grams of propylene imine, 30 grams of toluene and 3 grams of potassium carbonate were charged to a reaction flask equipped with a thermometer and a condenser connected to a cryostat (3° C.). The mixture was stirred with a mechanical stirrer under a nitrogen atmosphere. The mixture was then heated to 70° C. Samples were taken at regular intervals, and the reaction progress was monitored using a $^1$H-NMR until no signal (chemical shifts) correlated to the epoxide protons from the multifunctional epoxide was observed. After 20 hours of reaction, the mixture was diluted with toluene and filtered. The solvent and the excess of propylene imine were removed from the filtrate in vacuo to obtain a highly viscous brownish oil. The theoretical formula of the thus prepared (aziridinyl hydroxy)-functional organic compound is shown below, and the theoretical molecular weight was calculated to be 622.47 Da.

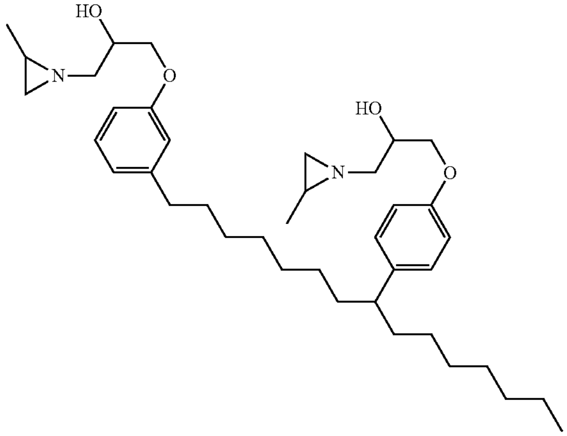 [SMILES: CCCCCCCC(CCCCCCCc1cccc(OCC(O)CN2CC2C)c1)c1ccc(OCC(O)CN2CC2C)cc1]

The molecular weight as defined and determined via MALDI-TOF MS—as this is defined and described in the specification—was 622.43 Da (=Obs. $[M+M+M_{Na+}]-[M_{Na+}]$).

Subsequently, 25.4 grams of the (aziridinyl hydroxy)-functional organic compound obtained above was mixed with 12.7 grams of methylethylketone and incubated at 50° C. until a homogeneous solution was obtained. 0.03 grams of triethylamine (TEA) and 5.1 grams of molten ATLAS™ G-5000 (dispersant) were added to the solution. The resulting mixture was stirred for 5 minutes at room temperature using an IKA T25 Digital Ultra-Turrax® mixer with S 25 N-18G head at 2000 rpm. Then, stirring was increased to 10000 rpm and 38.0 grams of demineralized water and triethylamine, were added gradually to the mixture over 15 minutes in order to adjust the pH to 11. During this addition process, the mixer was moved around the reaction vessel continuously. After completion of the addition, the resulting dispersion was stirred at 5000 rpm for 10 more minutes, and the pH of the dispersion was further adjusted to 12.5 with potassium hydroxide. The aqueous dispersion thus prepared contained the inventive particles (which were dispersed in water).

The inventive particles had a scatter intensity-based average hydrodynamic diameter ($D_H$) of 176 nm.

Assessment of Storage Stability and Crosslinking Efficiency

Starting viscosity (spindle S62): 182 mPa·s

End viscosity (spindle S62): 220 mPa·s

The end viscosity was 1.21 times higher (end viscosity/starting viscosity=1.21) than the starting viscosity.

Thus, the aqueous dispersion had a workable viscosity.

The starting chemical resistance was good.

The end chemical resistance was good.

The end chemical resistance was equal to the starting chemical resistance.

The crosslinking efficiency was good.

Given the above results, the inventive particles and/or the inventive aqueous dispersion comprising the inventive particles had surprisingly enhanced storage stability for prolonged time period and at elevated temperature (4 weeks at 50° C.) because:

i) they had a workable viscosity, and ii) the end chemical resistance was equal to the starting chemical resistance, at the same time maintained good crosslinking efficiency because the end chemical resistance was good.

Example 5

30.0 grams of Cardolite® NC-514S, 19.2 grams of propylene imine, 30 grams of toluene and 3 grams of potassium carbonate were charged to a reaction flask equipped with a thermometer and a condenser connected to a cryostat (3° C.). The mixture was stirred with a mechanical stirrer under a nitrogen atmosphere. The mixture was then heated to 70° C. Samples were taken at regular intervals, and the reaction progress was monitored using a $^1$H-NMR until no signal (chemical shifts) correlated to the epoxide protons from the multifunctional epoxide was observed. After 20 hours of reaction, the mixture was diluted with toluene and filtered. The solvent and the excess of propylene imine were removed from the filtrate in vacuo to obtain a highly viscous brownish oil. The theoretical formula of the thus prepared (aziridinyl hydroxy)-functional organic compound is shown below, and the theoretical molecular weight was calculated to be 622.47 Da.

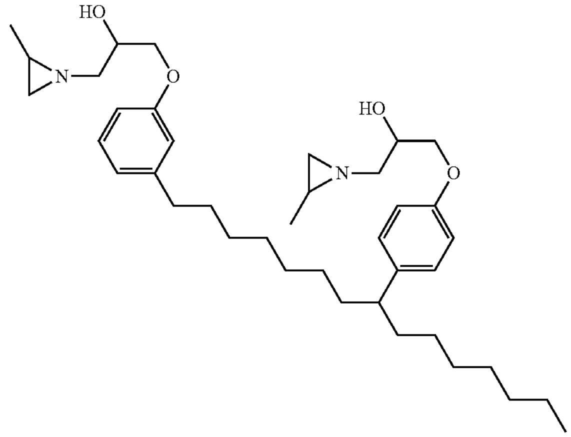 [SMILES: CCCCCCCC(CCCCCCCc1cccc(OCC(O)CN2CC2C)c1)c1ccc(OCC(O)CN2CC2C)cc1]

The molecular weight as defined and determined via MALDI-TOF MS—as this is defined and described in the specification—was 622.43 Da (=Obs. [M+$M_{Na+}$]-[$M_{Na+}$]).

In a separate reaction, 75 grams of EPALLOY® 9000 was dissolved in 75 mL of toluene and charged to a reaction flask equipped with a thermometer and a condenser connected to a cryostat (3° C.). Next, 55 grams of propylene imine and 5 grams of potassium carbonate were added to the flask. The mixture was stirred with a mechanical upper stirrer under a nitrogen atmosphere. The mixture was than heated to 80° C. Samples were taken at regular intervals and the reaction progress was monitored using a $^1$H-NMR until no signal (chemical shifts) correlated to the epoxide protons from the multifunctional epoxide was observed. After 22 hours of reaction, the mixture was filtered. The solvent and excess of propylene imine from the filtrate was removed in vacuo to obtain an off-white solid. The theoretical formula of the thus prepared (aziridinyl hydroxy)-functional organic compound is shown below and the theoretical molecular weight was calculated to be 645.38 Da.

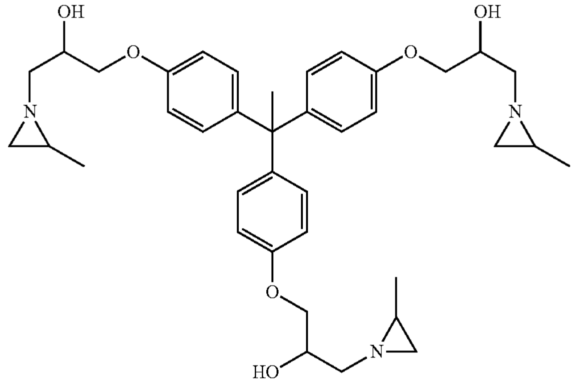 [SMILES: CC1CN1CC(O)COc1ccc(C(C)(c2ccc(OCC(O)CN3CC3C)cc2)c2ccc(OCC(O)CN3CC3C)cc2)cc1]

The molecular weight as defined and determined via MALDI-TOF MS—as this is defined and described in the specification—was 645.37 Da (=Obs. [M+$M_{Na+}$]-[$M_{Na+}$]).

Subsequently, 2.3 grams of the (aziridinyl hydroxy)-functional organic compound with theoretical molecular weight 645.38 Da obtained above, and 6.4 grams of the (aziridinyl hydroxy)-functional organic compound with theoretical molecular weight 622.47 Da obtained above, were mixed with 2.4 grams of toluene and 2.0 grams of methylethylketone and incubated at 50° C. until a homogeneous solution was obtained. 0.03 grams of triethylamine (TEA) and 1.8 grams of molten ATLAS™ G-5000 (dispersant) were added to the solution. The resulting mixture was stirred for 5 minutes at room temperature using an IKA T25 Digital Ultra-Turrax® mixer with S 25 N-18G head at 2000 rpm. Then, stirring was increased to 10000 rpm and 45.5 grams of demineralized water and triethylamine, were added gradually to the mixture over 15 minutes in order to adjust the pH to 11. During this addition process, the mixer was moved around the reaction vessel continuously. After completion of the addition, the resulting dispersion was stirred at 5000 rpm for 10 more minutes, and the pH of the dispersion was further adjusted to 11 with triethylamine. The aqueous dispersion thus prepared contained the inventive particles (which were dispersed in water).

The inventive particles had a scatter intensity-based average hydrodynamic diameter ($D_H$) of 397 nm.

Assessment of Storage Stability and Crosslinking Efficiency

Starting viscosity (spindle S62): 14 mPa·s

End viscosity (spindle S62): 41 mPa·s

The end viscosity was 2.93 times higher (end viscosity/starting viscosity=2.93) than the starting viscosity.

Thus, the aqueous dispersion had a workable viscosity.

The starting chemical resistance was good.

The end chemical resistance was good.

The end chemical resistance was equal to the starting chemical resistance.

The crosslinking efficiency was good.

Given the above results, the inventive particles and/or the inventive aqueous dispersion comprising the inventive particles had surprisingly enhanced storage stability for prolonged time period and at elevated temperature (4 weeks at 50° C.) because:

i) they had a workable viscosity, and ii) the end chemical resistance was equal to the starting chemical resistance, at the same time maintained good crosslinking efficiency because the end chemical resistance was good.

Example 6

180 grams of DESMODUR® N 3900 was dissolved in 150 grams of toluene, charged to a reaction flask equipped with a thermometer and heated to 50° C. Next, 0.05 grams of triethylamine was added to the flask and over the course of 150 minutes 74 grams of glycidol was slowly added to the reaction mixture, while making sure that the reaction temperature stayed constant between 55-58° C. After stirring for another 60 minutes at this temperature, the mixture was cooled down to room temperature and stirred for 18 hours at room temperature. The solvent was removed in vacuo and the resulting yellowish oil was transferred to a reaction flask equipped with a thermometer and a condenser connected to a cryostat (3° C.). Next, 250 grams of toluene, 175 grams of propylene imine and 10 grams of potassium carbonate were added to the flask. The mixture was stirred with a mechanical upper stirrer under a nitrogen atmosphere. The mixture was then heated to 60° C. Samples were taken at regular intervals, and the reaction progress was monitored using a $^{1}$H-NMR until no signal (chemical shifts) correlated to the epoxide protons from the multifunctional epoxide was observed. After 18 hours of reaction, the mixture was filtered. The solvent and the excess of propylene imine were removed from the filtrate in vacuo to obtain a high viscous liquid. The theoretical formula of the thus prepared (aziridinyl hydroxy)-functional organic compound is shown below and the theoretical molecular weight was calculated to be 897.55 Da.

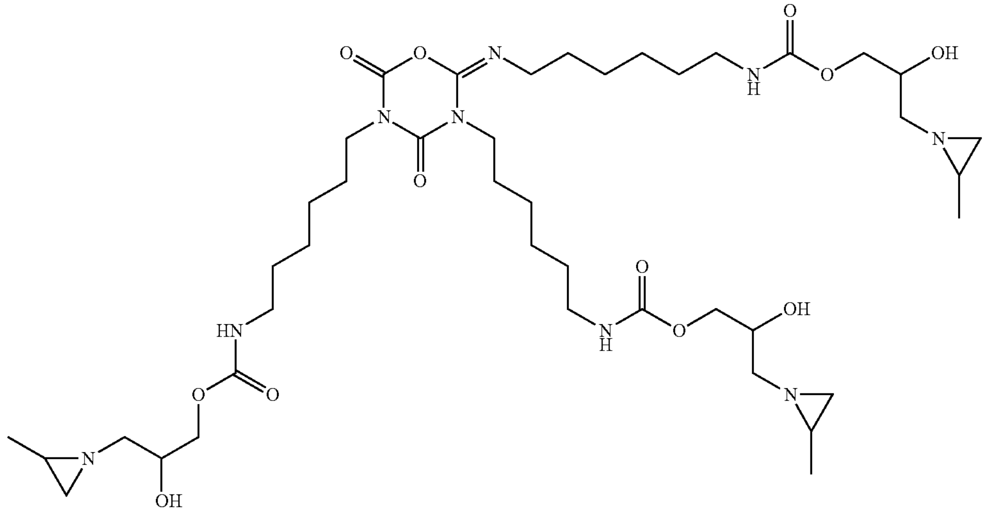 [SMILES: CC1CN1CC(O)COC(=O)NCCCCCC/N=c1/oc(=O)n(CCCCCCNC(=O)OCC(O)CN2CC2C)c(=O)n1CCCCCCNC(=O)OCC(O)CN1CC1C]

The molecular weight as defined and determined via MALDI-TOF MS—as this is defined and described in the specification—was 897.56 Da (=Obs. $[M+M_{Na+}]-[M_{Na+}]$).

Subsequently, 4.2 grams of NeoCryl® B-300 was dissolved in 4.2 grams of methylethylketone. In parallel, 4.2 grams of the (aziridinyl hydroxy)-functional organic compound obtained above was mixed with 2.1 grams of methylethylketone. Both solutions were mixed and incubated at 50° C. until a homogeneous mixture was obtained. 0.03 grams of triethylamine (TEA) and 2.5 grams of molten ATLAS™ G-5000 (dispersant) were added to the solution. The resulting mixture was stirred for 5 minutes at room temperature using an IKA T25 Digital Ultra-Turrax® mixer with S 25 N-18G head at 2000 rpm. Then, stirring was increased to 10000 rpm and 15.4 grams of demineralized water and triethylamine, were added gradually to the mixture over 15 minutes in order to adjust the pH to 11. During this addition process, the mixer was moved around the reaction vessel continuously. After completion of the addition, the resulting dispersion was stirred at 5000 rpm for 10 more minutes. Afterwards, the solvent was removed using a rotary evaporator, replenishing with an equal amount of demineralized water, and the pH of the dispersion was again adjusted to 11 with triethylamine. The aqueous dispersion thus prepared contained the inventive particles (which were dispersed in water).

The inventive particles had a scatter intensity-based average hydrodynamic diameter ($D_H$) of 100 nm.

Assessment of Storage Stability and Crosslinking Efficiency

Starting viscosity (spindle S62): 39 mPa·s

End viscosity (spindle S62): 40 mPa·s

The end viscosity was 1.03 time higher (end viscosity/starting viscosity=1.03) than the starting viscosity.

Thus, the aqueous dispersion had a workable viscosity.

The starting chemical resistance was good.

The end chemical resistance was good.

The end chemical resistance was equal to the starting chemical resistance.

The crosslinking efficiency was good.

Given the above results, the inventive particles and/or the inventive aqueous dispersion comprising the inventive particles had surprisingly enhanced storage stability for prolonged time period and at elevated temperature (4 weeks at 50° C.) because:

i) they had a workable viscosity, and ii) the end chemical resistance was equal to the starting chemical resistance, at the same time maintained good crosslinking efficiency because the end chemical resistance was good.

3. COMPARATIVE EXAMPLES

Example 1C

The trimethylolpropane tris(2-methyl-1-aziridinepropionate) (commercial product name 'crosslinker CX-100') has the following structure:

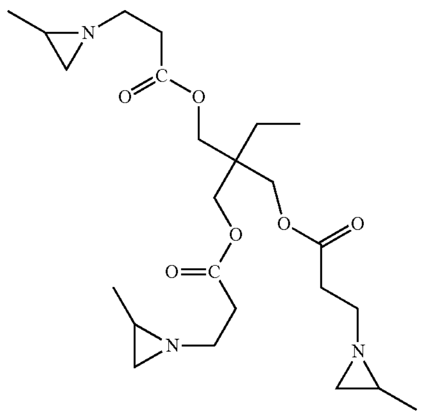

and the theoretical molecular weight was calculated to be 467.30 Da.

7.5 grams of trimethylolpropane tris(2-methyl-1-aziridinepropionate) were mixed with 3.75 grams of acetone and incubated at 50° C. until a homogeneous solution was obtained. Subsequently, 0.03 grams of triethylamine and 0.75 grams of molten Atlas™ G-5000 dispersant were added to the solution. The resulting mixture was stirred for 5 minutes at room temperature using an IKA T25 Digital Ultra-Turrax® mixer with S 25 N-18G head at 2000 rpm. Then, stirring was increased to 10000 rpm and 7.5 grams of demineralized water, an amount of triethylamine to adjust the pH to 10, were added gradually to the mixture over 15 minutes. During this addition process, the mixer was moved around the reaction vessel continuously. After completion of the addition, the mixture was stirred at 5000 rpm for additional 10 minutes, and the pH of the mixture was set to 10 by using triethylamine. This resulted in a homogenous solution which did not contain any particles.

Assessment of Storage Stability and Crosslinking Efficiency

Starting viscosity (spindle S62): 178 mPa·s

End viscosity (spindle S62): not possible to measure because the aqueous composition gelled during the 2$^{nd}$ week of storage Thus, the aqueous composition did not have a workable viscosity.

The starting chemical resistance was excellent.

The end chemical resistance was not possible to measure because the aqueous composition gelled during the 2$^{nd}$ week of storage.

Thus, the crosslinking efficiency was poor.

Given the above results, the trimethylolpropane tris(2-methyl-1-aziridinepropionate) and/or its solution failed to provide for enhanced storage stability for a prolonged time period and at elevated temperature (4 weeks at 50° C.) because they did not have a workable viscosity, and at the same time failed to maintain good crosslinking efficiency.

Example 2C 299 grams of bisphenol A diglycidyl ether, 250 grams of toluene, 255 grams of propylene imine and 10 grams of potassium carbonate were charged to a reaction flask equipped with a thermometer and a condenser connected to a cryostat (3° C.). The mixture was stirred with a mechanical upper stirrer under a nitrogen atmosphere. The mixture was than heated to 70° C. Samples were taken at regular intervals and the reaction progress was monitored using a $^1$H-NMR until no signal (chemical shifts) correlated to the epoxide protons from the multifunctional epoxide was observed. After 19 hours of reaction, the mixture was filtered. The solvent and excess of propylene imine from the filtrate was removed in vacuo to obtain a highly viscous liquid. The theoretical formula of the thus prepared multi-aziridine compound is shown below and the theoretical molecular weight was calculated to be 454.28 Da.

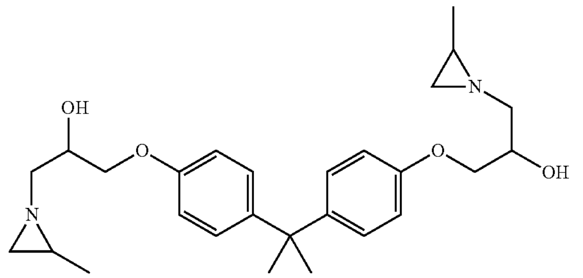 [SMILES: CC1CN1CC(O)COc1ccc(C(C)(C)c2ccc(OCC(O)CN3CC3C)cc2)cc1]

The molecular weight as defined and determined via MALDI-TOF MS—as this is defined and described in the specification—was 454.26 Da (=Obs. $[M+M_{Na+}]-[M_{Na+}]$).

6.95 grams of the multi-aziridine compound obtained above were mixed with 5.00 grams of methylethylketone (MEK) and incubated at 50° C. until a homogeneous solution was obtained. Subsequently, 0.03 grams of triethylamine and 1.20 grams of molten Atlas™ G-5000 dispersant were added to the solution. The resulting mixture was stirred for 5 minutes at room temperature using an IKA T25 Digital Ultra-Turrax® mixer with S 25 N-18G head at 2000 rpm. Then, stirring was increased to 10000 rpm and 7.5 grams of demineralized water were added gradually to the mixture over 15 minutes. During this addition process, the mixer was moved around the reaction vessel continuously. After completion of the addition, the resulting mixture was stirred at 5000 rpm for additional 10 minutes. The aqueous dispersion thus prepared contained particles (which were dispersed in water).

The particles had a scatter intensity-based average hydrodynamic diameter ($D_H$) of 517 nm.

Assessment of Storage Stability and Crosslinking Efficiency

Starting viscosity (spindle S62): 10 mPa·s

End viscosity (spindle S62): not possible to measure because the aqueous composition gelled during the 1st week of storage Thus, the aqueous composition did not have a workable viscosity.

The starting chemical resistance was good.

The end chemical resistance was not possible to measure because the aqueous composition gelled during the 1st week of storage.

Thus, the crosslinking efficiency was poor.

Given the above results, this multi-aziridine compound obtained above and/or its aqueous dispersion failed to provide for enhanced storage stability for prolonged time period and at elevated temperature (4 weeks at 50° C.) because they did not have a workable viscosity, and at the same time failed to maintain a good crosslinking efficiency.

Example 3C 24.0 grams of N,N-diglycidyl-4-glycidyloxyaniline, 42.0 grams of propylene imine, 30 grams of toluene and 3 grams of potassium carbonate were charged to a reaction flask equipped with a thermometer and a condenser connected to a cryostat (3° C.). The mixture was stirred with a mechanical stirrer under a nitrogen atmosphere. The mixture was than heated to 70° C. Samples were taken at regular intervals and the reaction progress was monitored using a $^1$H-NMR until no signal (chemical shifts) correlated to the epoxide protons from the multifunctional epoxide was observed. After 24 hours of reaction, the mixture was diluted with toluene and filtered. The solvent and excess of propylene imine from the filtrate was removed in vacuo to obtain a highly viscous yellow material. The theoretical formula of the thus prepared multi-aziridine compound is shown below and the theoretical molecular weight was calculated to be 448.30 Da.

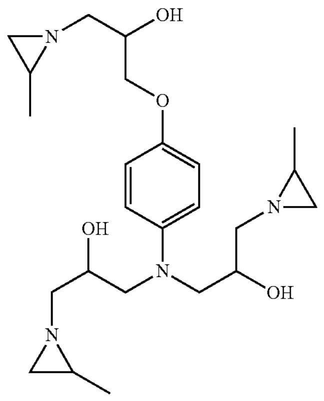 [SMILES: CC1CN1CC(O)COc1ccc(N(CC(O)CN2CC2C)CC(O)CN2CC2C)cc1]

The molecular weight as defined and determined via MALDI-TOF MS—as this is defined and described in the specification—was 448.29 Da (=Obs. [M+$M_{Na+}$]-[$M_{Na+}$]).

This compound was disclosed in U.S. Pat. No. 3,329,674 in cl. 2, II. 29-39.

9.80 grams of the multi-aziridine compound obtained above were mixed with 4.90 grams of acetone and incubated at 50° C. until a homogeneous solution was obtained. Subsequently, 0.03 grams of triethylamine and 1.03 grams of molten Atlas™ G-5000 dispersant were added to the solution. The resulting mixture was stirred for 5 minutes at room temperature using an IKA T25 Digital Ultra-Turrax® mixer with S 25 N-18G head at 2000 rpm. Then, stirring was increased to 10000 rpm and 9.90 grams of demineralized water were added gradually to the mixture over 15 minutes. During this addition process, the mixer was moved around the reaction vessel continuously. After completion of the addition, the mixture was stirred at 5000 rpm for additional 10 minutes, and the pH of the mixture was set to 10 by using triethylamine. This resulted in a homogenous solution which did not contain any particles.

Assessment of Storage Stability and Crosslinking Efficiency

Starting viscosity (spindle S62): 52 mPa·s

End viscosity (spindle S62): not possible to measure because the solution gelled during the 1st week of storage.

Thus, the solution did not have a workable viscosity.

The starting chemical resistance was very good.

The end chemical resistance was not possible to measure because the solution gelled during the 1st week of storage.

Thus, the crosslinking efficiency was poor.

Given the above results, the multi-aziridine compound obtained above and/or its solution failed to provide for enhanced storage stability for a prolonged time period and at elevated temperature (4 weeks at 50° C.) because they did not have a workable viscosity, and at the same time failed to maintain good crosslinking efficiency.

Example 4C 75 grams of ERISYS® GA-240, 80 grams of propylene imine and 5 grams of potassium carbonate were charged to a reaction flask equipped with a thermometer and a condenser connected to a cryostat (3° C.). The mixture was stirred with a mechanical upper stirrer under a nitrogen atmosphere. The mixture was than heated to 71° C. Samples were taken at regular intervals and the reaction progress was monitored using a $^1$H-NMR until no signal (chemical shifts) correlated to the epoxide protons from the multifunctional epoxide was observed. After 22 hours of reaction, the mixture was diluted with toluene and filtered. The solvent and excess of propylene imine from the filtrate was removed in vacuo to obtain a clear, transparent solid. The theoretical formula of the AZ-component is shown below and the theoretical molecular weight was calculated to be 588.44 Da.

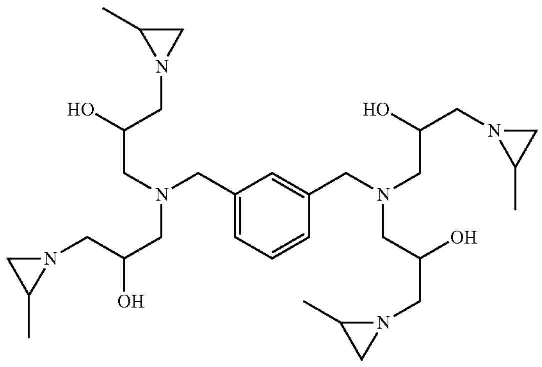 [SMILES: CC1CN1CC(O)CN(Cc1cccc(CN(CC(O)CN2CC2C)CC(O)CN2CC2C)c1)CC(O)CN1CC1C]

The molecular weight as defined and determined via MALDI-TOF MS—as this is defined and described in the specification—was 588.48 Da (=Obs. $[M+M_{Na+}]-[M_{Na+}]$).

9.68 grams of the transparent solid described above were mixed with 4.90 grams of acetone and incubated at 50° C. until a homogeneous solution was obtained. Subsequently, 0.03 grams of triethylamine and 0.96 grams of molten Atlas™ G-5000 dispersant were added to the solution. The resulting mixture was stirred for 5 minutes at room temperature using an IKA T25 Digital Ultra-Turrax® mixer with S 25 N-18G head at 2000 rpm. Then, stirring was increased to 10000 rpm and 9.65 grams of demineralized water were added gradually to the mixture over 15 minutes. During this addition process, the mixer was moved around the reaction vessel continuously. After completion of the addition, the mixture was stirred at 5000 rpm for additional 10 minutes, and the pH of the mixture was set to 10 by using triethylamine. This resulted in a homogenous solution which did not contain any particles.

Assessment of Storage Stability and Crosslinking Efficiency

Starting Viscosity (Spindle S62): 64 mPa·s

End viscosity (spindle S62): not possible to measure because the solution gelled during the $1_{st}$ week of storage.

Thus, the solution did not have a workable viscosity.

The starting chemical resistance was very good.

The end chemical resistance was not possible to measure because the solution gelled during the $1^{st}$ week of storage.

Thus, the crosslinking efficiency was poor.

Given the above results, the multi-aziridine compound obtained above and/or its solution failed to provide for enhanced storage stability for a prolonged time period and at elevated temperature (4 weeks at 50° C.) because they did not have a workable viscosity, and at the same time failed to maintain good crosslinking efficiency.

4. CONCLUSION

The U.S. Pat. No. 3,329,674 to Thiokol Chemical Corporation (prior art), as explained in detail in the specification, did neither disclose any particles—let alone any particles of compounds bearing aziridine group(s), let alone that these compounds had a molecular weight of at least 600 and at most 10000 Da—, nor any aqueous dispersions comprising particles which particles comprised an (aziridinyl hydroxy)-functional organic component. The U.S. Pat. No. 3,329,674 failed to provide for the combination of enhanced storage stability (at elevated temperature and for a prolonged time period; 4 weeks at 50° C.) of aqueous dispersions comprising organic compounds bearing aziridine ring(s), maintaining at least good crosslinking efficiency (the crosslinking efficiency was poor). Evidence for that is the Example 3C shown in the specification.

Upon comparing the results of the inventive Examples 1 to 6 and those of the comparative Examples 1C to 4C (that includes an example taken from the prior art and in particular from the U.S. Pat. No. 3,329,674 (Example 3C herein), it is evident that only the particles of the invention (and the aqueous dispersions of the invention) were able to provide for aqueous dispersions comprising organic compounds bearing aziridine ring(s) that had enhanced storage stability for a prolonged time period and at elevated temperature (4 weeks at 50° C.), and at the same time maintained at least good crosslinking efficiency.

The invention claimed is:

1. Particles comprising an (aziridinyl hydroxy)-functional organic component (AZ-component), wherein the particles have a scatter intensity-based average hydrodynamic diameter ($D_H$) determined via dynamic light scattering, of at least 2 and at most 3000 nm, and wherein the (aziridinyl hydroxy)-functional organic component (AZ-component) is selected from the group consisting of i) to vi): i) (aziridinyl hydroxy)-functional organic compound AZ1 of Formula A1 having only two aziridine rings (AZ1-compound), ii) (aziridinyl hydroxy)-functional organic compound AZ2 of Formula A2 having only three aziridine rings (AZ2-compound), iii) (aziridinyl hydroxy)-functional organic compound AZ3 of Formula A3 having only four aziridine rings (AZ3-compound), iv) (aziridinyl hydroxy)-functional organic compound AZ4 of Formula A4 having only five aziridine rings (AZ4-compound), v) (aziridinyl hydroxy)-functional organic compound AZ5 of Formula A5 having only six aziridine rings (AZ5-compound), and vi) mixtures thereof,

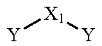

Formula A1

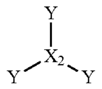

Formula A2

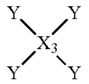

Formula A3

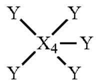

Formula A4

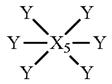

Formula A5 wherein $X_1$ is a bivalent aliphatic organic radical or a bivalent aromatic organic radical;

$X_2$ is a trivalent aliphatic organic radical or a trivalent aromatic organic radical;

$X_3$ is a quadrivalent aliphatic organic radical or a quadrivalent aromatic organic radical;

$X_4$ is a pentavalent aliphatic organic radical or a pentavalent aromatic organic radical;

$X_5$ is a hexavalent aliphatic organic radical or a hexavalent aromatic organic radical;

and wherein each of the $X_1$ to $X_5$ consists of a collection of atoms covalently connected in a configuration that comprises linear and/or branched and/or ring structures, which collection of atoms is selected from the group consisting of i) to x): i) carbon and hydrogen atoms, ii) carbon, hydrogen and oxygen atoms, iii) carbon, hydrogen and nitrogen atoms, iv) carbon, hydrogen and sulphur atoms, v) carbon, hydrogen, oxygen and nitrogen atoms, vi) carbon, hydrogen, nitrogen and sulphur atoms, vii) carbon, hydrogen, oxygen and sulphur atoms, viii) carbon, hydrogen, oxygen, nitrogen and sulphur atoms, ix) carbon, hydrogen and silicon atoms, and x) carbon, hydrogen, oxygen and silicon atoms and xi) any combination of ix) and/or x) with any one or all of the iii) to viii), and wherein each of the $X_1$ to $X_5$ has carbon atoms and hydrogen atoms, and wherein each of the $X_1$ to $X_5$ has optionally oxygen atoms and/or nitrogen atoms and/or sulphur atoms and/or silicon atoms, and wherein the $X_1$, and/or the $X_2$ and/or the $X_3$ and/or the $X_4$ and/or the $X_5$ may optionally comprise an ionic functional group, and wherein Y is a monovalent organic radical selected from the group consisting of: i) monovalent (aziridinyl hydroxyisopropyl) organic radical of Formula B1, ii) monovalent (aziridinyl hydroxycyclohexane) organic radical of Formula B2, and iii) monovalent (aziridinyl hydroxycyclohexane) organic radical of Formula B3, Formula B1

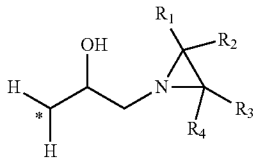

Formula B2

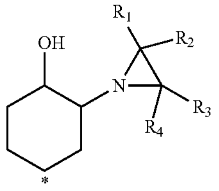

Formula B3

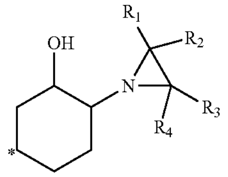

and wherein $R_1$ is selected from the group consisting of hydrogen and methyl; and $R_2$ is selected from the group consisting of hydrogen, methyl, and $C_2$-$C_5$ alkyl; and $R_3$ is selected from the group consisting of methyl, and $C_2$-$C_4$ alkyl; and $R_4$ is selected from the group consisting of hydrogen, methyl, and $C_2$-$C_4$ alkyl; and wherein the Y in each of the compounds A1 to A5 may be the same or different to each other, and wherein each of the single covalent bonds between the Y and each one of the $X_1$ to $X_5$ is selected from the group consisting of carbon-carbon single bond, carbon-oxygen single bond and carbon-nitrogen single bond, and wherein each of the AZ1- to AZ5-compound has a molecular weight determined via MALDI-TOF MS, of at least 600 and at most 10000 Da.

2. The particles according to the claim 1, wherein the $X_1$ is a bivalent aliphatic organic radical or a bivalent aromatic organic radical other than a bivalent radical of bisphenol A.

3. The particles according to claim 1, wherein the $X_1$, and/or the $X_2$ and/or the $X_3$ and/or the $X_4$ and/or the $X_5$ comprises at least one structural unit or a combination of structural units selected from the group consisting of unit 1, unit 2, unit 3, unit 4, unit 5, unit 6, unit 7, unit 8, unit 9, unit 10, and unit 11, as the units 1 to 11 are depicted below:

unit 1

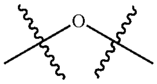

unit 2

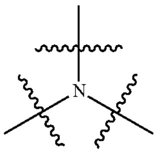

unit 3

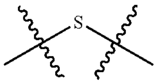

unit 4

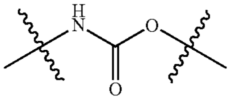

unit 5

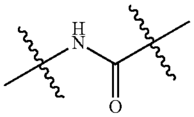

unit 6

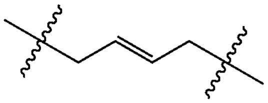

unit 7

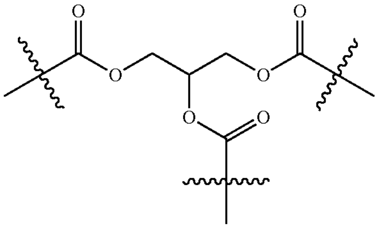

unit 8

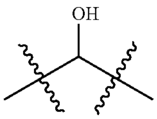

unit 9

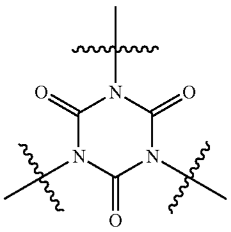

unit 10

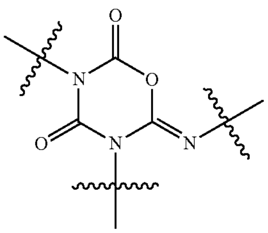

-continued unit 11

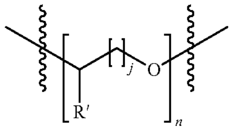

wherein

R' is selected from the group consisting of hydrogen and methyl; and j is an integer ranging from 1 to 5; and n is an integer ranging from and including 2 up to and including 50.

4. The particles according to claim 1, wherein the aggregate number of carbon atoms in $R_1$, and $R_2$ and $R_3$ and $R_4$ is at most 9.

5. The particles according to claim 1, wherein the $X_1$ and/or the $X_2$ and/or the $X_3$ and/or the $X_4$ and/or the $X_5$ does not contain one or any combination of the following structural units BP1, BP2, BP3, and BS unit BP1

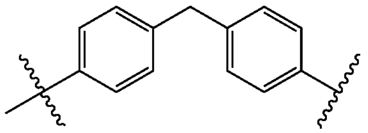

unit BP2

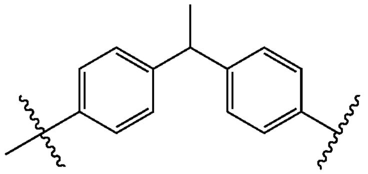

unit BP3

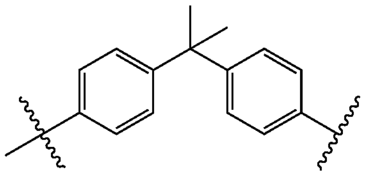

-continued unit BS

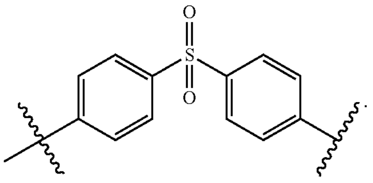

6. The particles according to claim 1, wherein the $X_1$ is the bivalent aliphatic organic radical of Formula Ala'

Formula A1a

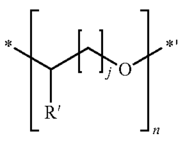

wherein

R' is selected from the group consisting of hydrogen and methyl; and j is an integer ranging from 1 to 5; and n is an integer ranging from and including 2 up to and including 50.

7. The particles according to claim 1, wherein the AZ-component is selected from the group consisting of i) to v):

i) (aziridinyl hydroxy)-functional organic compound AZ1 of Formula A1 (AZ1-compound), ii) (aziridinyl hydroxy)-functional organic compound AZ2 of Formula A2 (AZ2-compound), iii) (aziridinyl hydroxy)-functional organic compound AZ3 of Formula A3 (AZ3-compound), iv) (aziridinyl hydroxy)-functional organic compound AZ5 of Formula A5 (AZ5-compound), and v) mixtures thereof, and wherein the AZ1-compound is selected from the group consisting of compounds having the Formula A1a, compounds having the Formula Alb, compounds having the Formula A1c, and compounds having the Formula A1d, as each of these Formulae A1a-A1d is described below Formula A1a

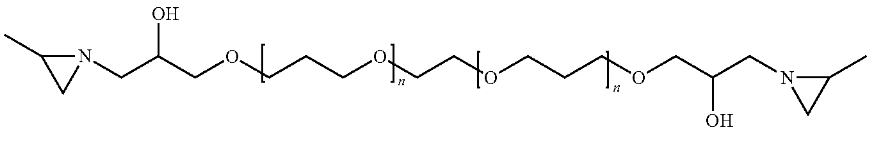

wherein each of the n in Formula Ala is independently selected, and each of the n in Formula A1a is an integer ranging from and including 2 up to and including 20; and Formula A1b

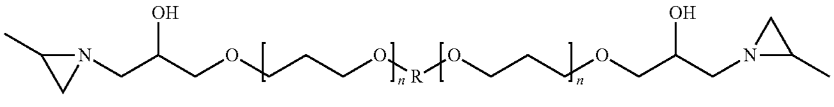

wherein the R in Formula Alb is a $C_3$-$C_{10}$ saturated hydrocarbylene, and wherein each of the n in Formula Alb is independently selected and each of the n in Formula A1b is an integer ranging from and including 2 up to and including 20; and Fromula A1c

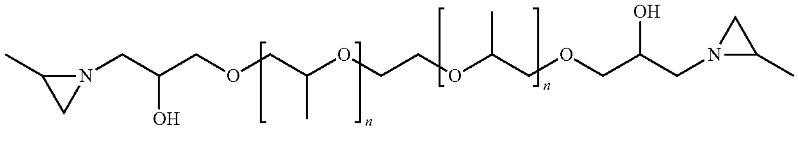

wherein each of the n in Formula A1c is independently selected, and each of the n in Formula A1c is an integer ranging from and including 2 up to and including 20; and Formula A1d

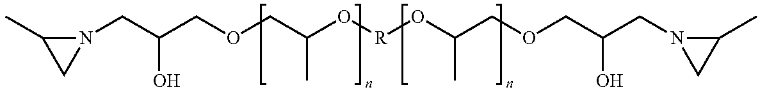

wherein the R in Formula A1d is a $C_3$-$C_{10}$ saturated hydrocarbylene, and wherein each of the n in Formula A1d is independently selected, and each of the n in Formula A1d is an integer ranging from and including 2 up to and including 20; and wherein the AZ2-compound is selected from the group consisting of compounds having the Formula A2a, compounds having the Formula A2b, compounds having the Formula A2c, compounds having the Formula A2d, compounds having the Formula A2e, as each of these Formulae A2a-A2e is described below Formula A2a

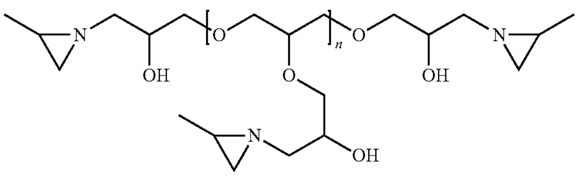

wherein the n in Formula A2a is an integer ranging from and including 2 up to and including 20; and Formula A2b

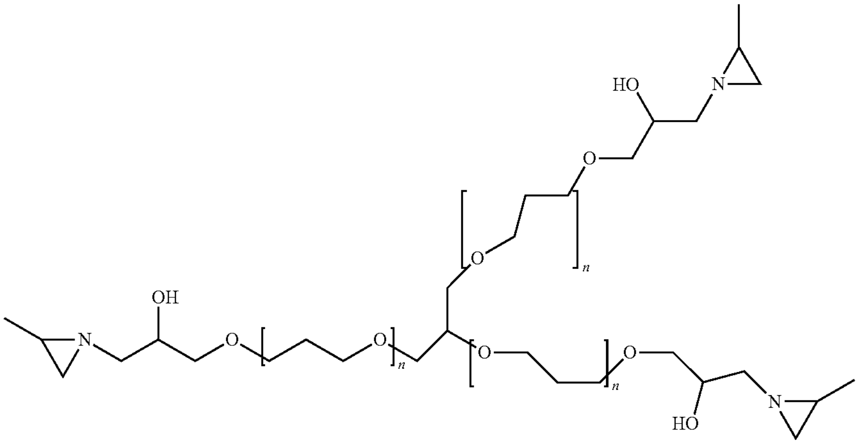

wherein each of the n in Formula A2b is independently selected, and each of the n in Formula A2b is an integer ranging from and including 2 up to and including 20; and
Formula A2c
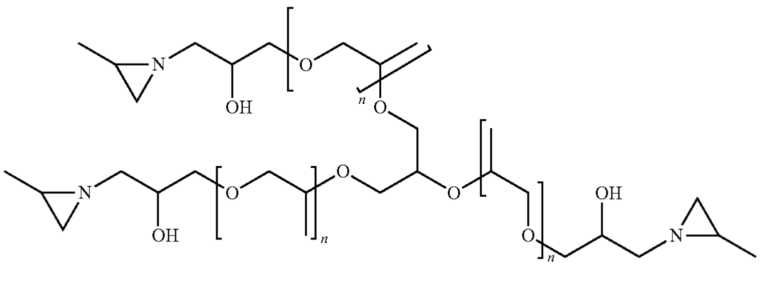
wherein each of the n in Formula A2c is independently selected, and each of the n in Formula A2c is an integer ranging from and including 2 up to and including 20; and
Formula A2d
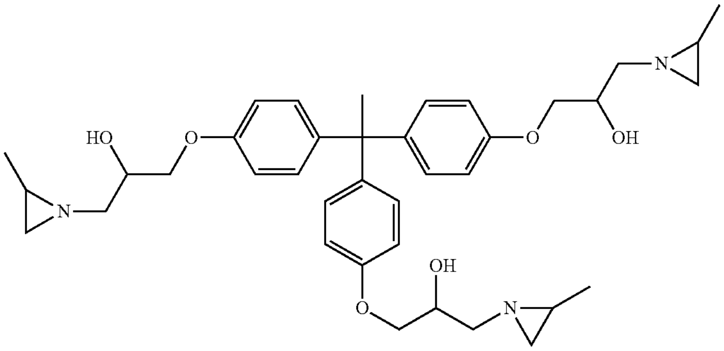
and
Formula A2e
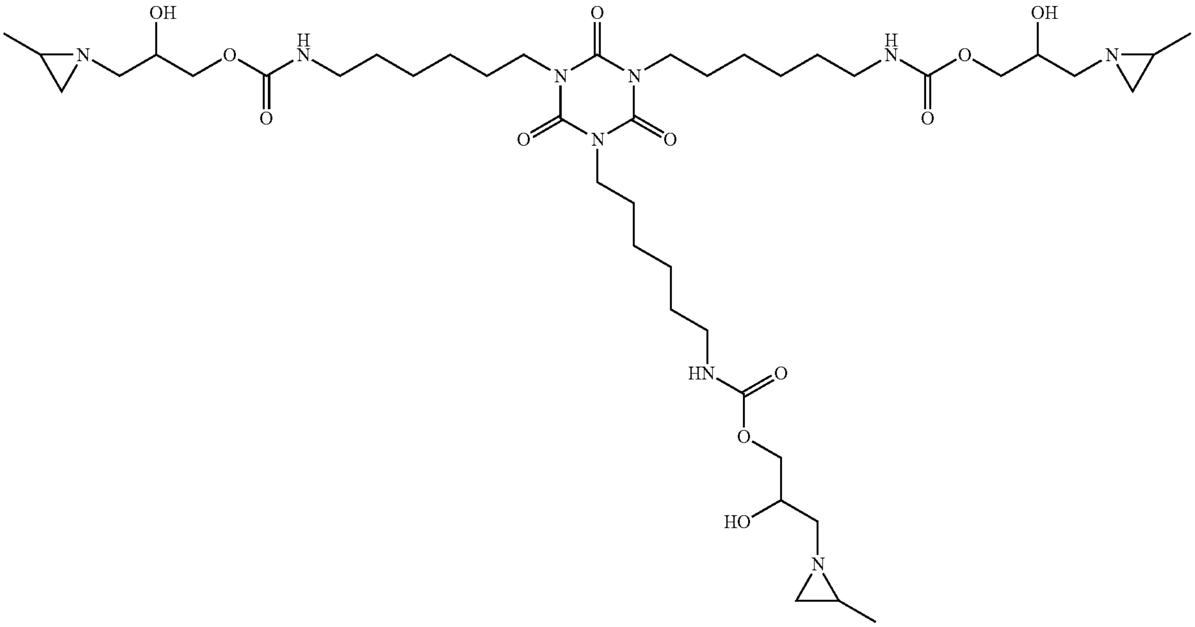

and wherein the AZ3-compound is selected from the group consisting of compounds having the Formula A3a Formula A3a

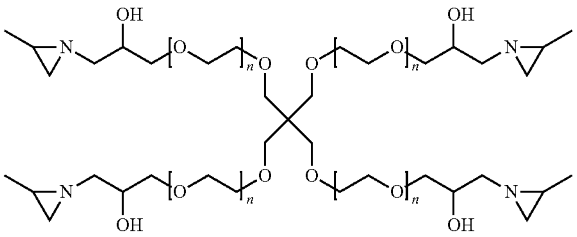

wherein each of the n in Formula A3a is independently selected, and each of the n in Formula A3a is an integer ranging from and including 2 up to and including 20; and wherein the AZ5-compound is selected from the group consisting of compounds having the Formula A5a Formula A5a

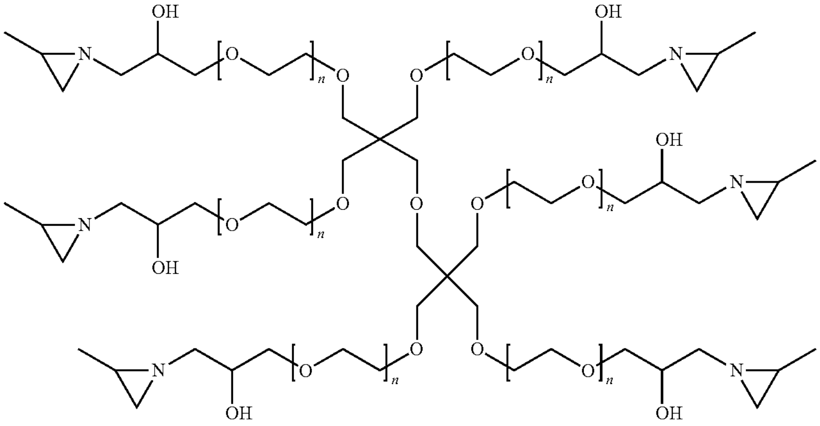

wherein each of the n in Formula A5a is independently selected, and each of the n in Formula A5a is an integer ranging from and including 2 up to and including 40.

8. The particles according to claim 1, wherein the AZ-component is selected from the group consisting of AZ1-compound and wherein the AZ1-compound is the compound of the following formula,

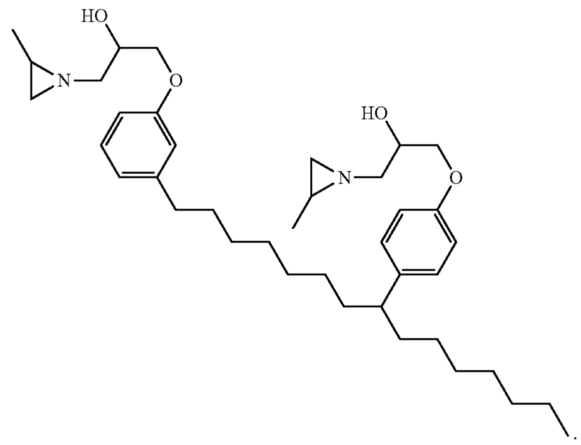 [SMILES: CCCCCCCC(CCCCCCCc1cccc(OCC(O)CN2CC2C)c1)c1ccc(OCC(O)CN2CC2C)cc1]

9. The particles according to claim 1, wherein the AZ-component is selected from the group consisting of AZ2-compound and wherein the AZ2-compound is the compound of the following formula,

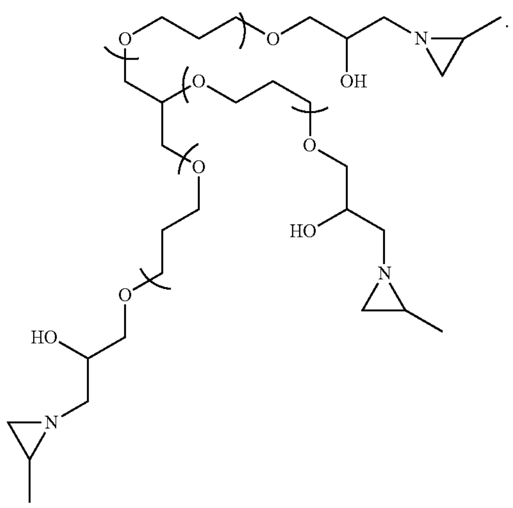

10. The particles according to claim 1, wherein the AZ-component is selected from the group consisting of AZ2-compound and wherein the AZ2-compound is the compound of the following formula,

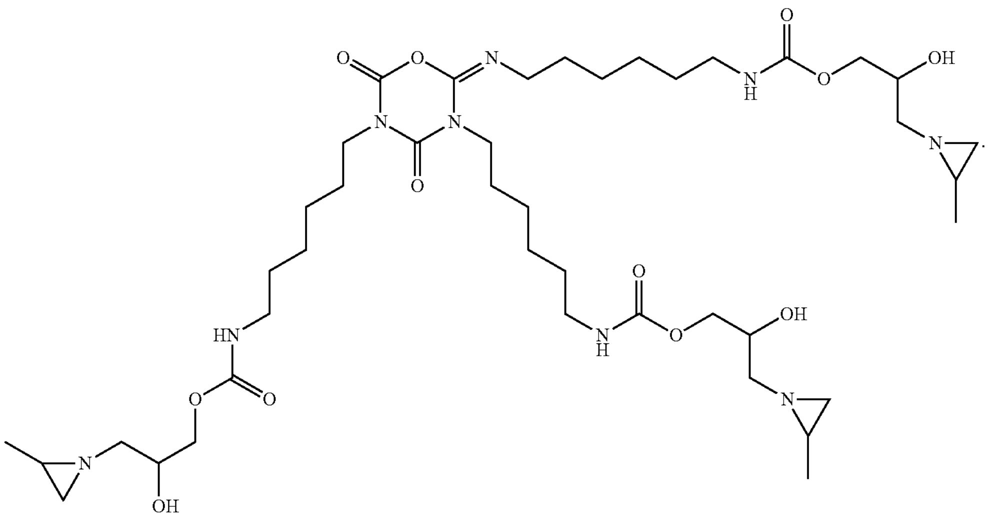 [SMILES: CC1CN1CC(O)COC(=O)NCCCCCC/N=c1/oc(=O)n(CCCCCCNC(=O)OCC(O)CN2CC2C)c(=O)n1CCCCCCNC(=O)OCC(O)CN1CC1C]

11. The particles according to claim 1, wherein the AZ-component is selected from the group consisting of AZ2-compound and wherein the AZ2-compound is the compound of the following formula,

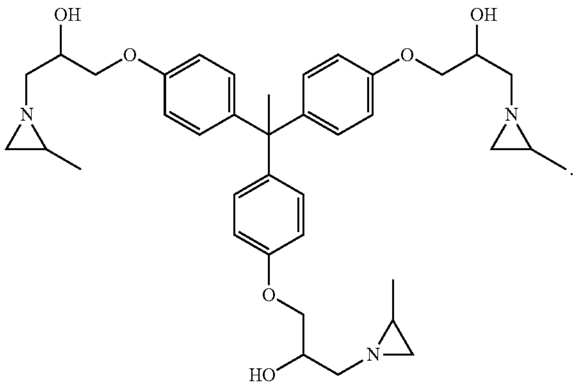 [SMILES: CC1CN1CC(O)COc1ccc(C(C)(c2ccc(OCC(O)CN3CC3C)cc2)c2ccc(OCC(O)CN3CC3C)cc2)cc1]

12. The particles according to claim 1, wherein the AZ-component is selected from the group consisting of AZ1-compound, AZ2-compound and mixtures thereof, and wherein the AZ1-compound is the compound of the following formula,

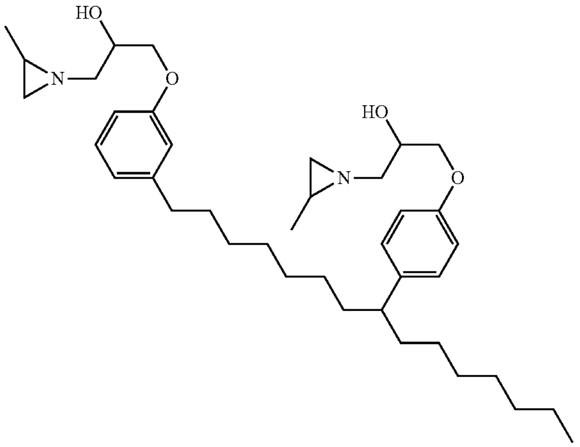 [SMILES: CCCCCCCC(CCCCCCCc1cccc(OCC(O)CN2CC2C)c1)c1ccc(OCC(O)CN2CC2C)cc1]

and wherein the AZ2-compound is selected from the group consisting of compounds of the following formulae,

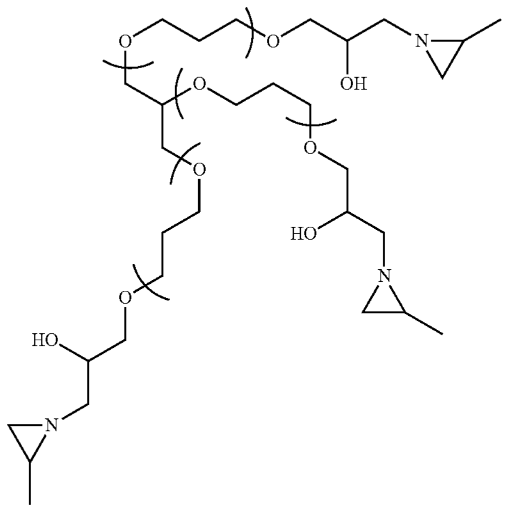

-continued

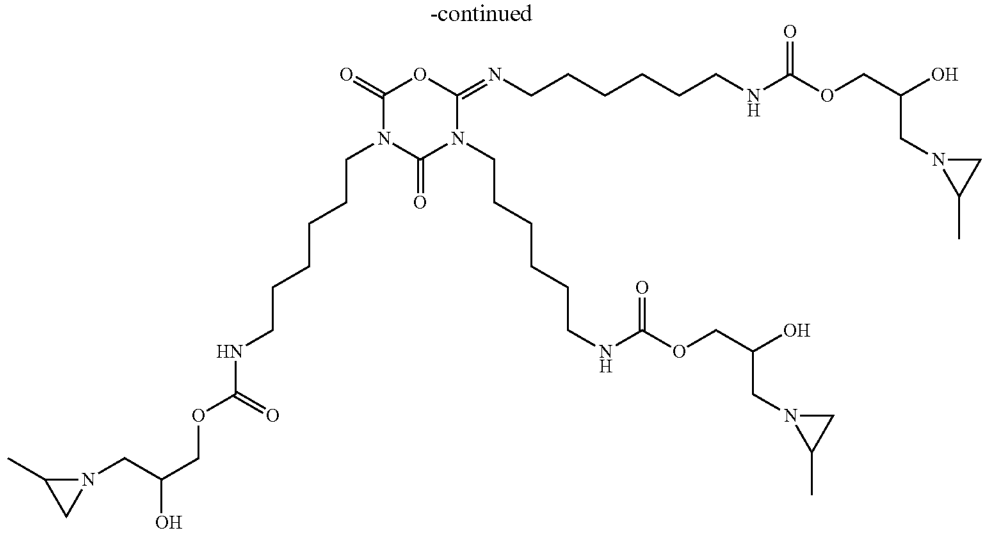

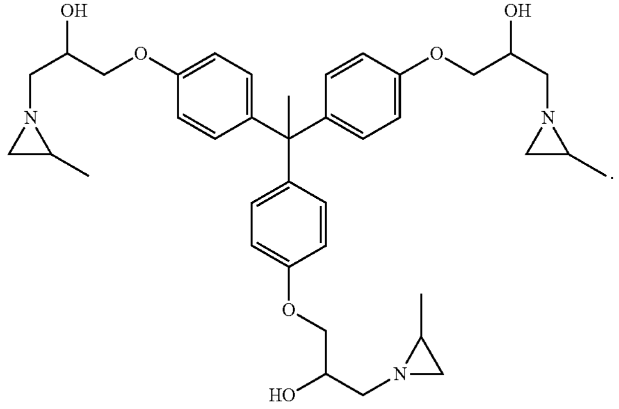

13. An aqueous dispersion having a pH determined according to the ISO 976:2013 of at least 7.5 and at most 14.0, and wherein the aqueous dispersion comprises:
i) water, and
ii) the particles according to claim 1 dispersed in the water.

14. The particles of claim 1, wherein the particles are obtained by a process comprising the steps of:
i) providing an aqueous dispersion having a pH determined according to the ISO 976:2013 of at least 7.5 and at most 14.0, and wherein the aqueous dispersion comprises:
a) water, and
b) the particles dispersed in the water; and
ii) removing the water—and any organic solvent if present—from the aqueous dispersion in order to obtain the particles;
iii) collecting the particles, and
iv) optionally further drying the particles.

15. An aqueous composition comprising:
i) the aqueous dispersion according to the claim 13, and
ii) a polymer which has an acid value determined according to the ASTM D1639-90 (1996)el in the range from 5 to 300 mg KOH/g and wherein the polymer may optionally comprise ionic functional groups.

16. A kit-of-parts comprising parts A and B which are physically separated from each other, wherein:
i) the part A comprises the aqueous dispersion according to claim 13, and
ii) the part B comprises a polymer which has an acid value determined according to the ASTM D1639-90 (1996)el in the range from 5 to 300 mg KOH/g, and wherein the polymer may optionally comprise ionic functional groups, and wherein the part A does not comprise the polymer of the part B, and the part B does not comprise the aqueous dispersion of the part A.

17. An article comprising the particles according to claim 1.

18. Coatings, paints, inks, varnishes, lubricants, adhesives, additively manufactured objects, 3D printed objects, textiles, waxes, fuels, photographic media, plastics, medical compositions, or medical devices comprising the particles according to claim 1.

19. The aqueous dispersion according to claim 13, wherein the pH is at least 9.0 and at most 13.0.

20. A method for curing particles comprising:
providing the particles of claim 1; and
curing the particles.

21. A method for curing an aqueous dispersion comprising:
providing the aqueous dispersion of claim 13; and
curing the particles.

22. A method for curing an aqueous composition comprising:
providing the aqueous composition of claim 15; and
curing the aqueous composition by reacting the particles with the polymer.

23. A method for forming an article comprising:
providing the aqueous composition of claim 15; and
curing the aqueous composition by reacting the particles with the polymer to form the article.

* * * * *